(12) United States Patent
Becker et al.

(10) Patent No.: US 9,345,750 B2
(45) Date of Patent: May 24, 2016

(54) LONG-ACTING FORMULATIONS OF INSULIN

(71) Applicant: SANOFI, Paris (FR)

(72) Inventors: Reinhard Becker, Frankfurt am Main (DE); Annke Hahn, Frankfurt am Main (DE); Peter Boderke, Schwalbach (DE); Christiane Fuerst, Frankfurt am Main (DE); Werner Mueller, Frankfurt am Main (DE); Ulrich Werner, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/220,562

(22) Filed: Mar. 20, 2014

(65) Prior Publication Data
US 2014/0206611 A1 Jul. 24, 2014

Related U.S. Application Data

(63) Continuation of application No. 13/110,568, filed on May 18, 2011, now abandoned.

(60) Provisional application No. 61/411,608, filed on Nov. 9, 2010, provisional application No. 61/429,936, filed on Jan. 5, 2011.

(30) Foreign Application Priority Data

| May 19, 2010 | (EP) | 10305532 |
| Jul. 13, 2010 | (EP) | 10305780 |
| Feb. 10, 2011 | (EP) | 11305140 |

(51) Int. Cl.

| A61K 38/28 | (2006.01) |
| A61K 9/00 | (2006.01) |
| A61K 9/08 | (2006.01) |
| A61K 38/26 | (2006.01) |
| A61K 38/22 | (2006.01) |
| A61K 47/02 | (2006.01) |
| A61K 47/10 | (2006.01) |
| A61K 47/26 | (2006.01) |

(52) U.S. Cl.
CPC ............... *A61K 38/28* (2013.01); *A61K 9/0019* (2013.01); *A61K 9/08* (2013.01); *A61K 38/2278* (2013.01); *A61K 38/26* (2013.01); *A61K 47/02* (2013.01); *A61K 47/10* (2013.01); *A61K 47/26* (2013.01)

(58) Field of Classification Search
None
See application file for complete search history.

(56) References Cited

U.S. PATENT DOCUMENTS

| 4,960,702 A | 10/1990 | Rice et al. |
| 5,070,186 A | 12/1991 | Joergensen |
| 5,370,629 A * | 12/1994 | Michel et al. ................. 604/207 |
| 5,509,905 A * | 4/1996 | Michel ........................... 604/207 |
| 5,656,722 A * | 8/1997 | Dorschug ..................... 530/303 |
| 5,952,297 A | 9/1999 | De Felippis et al. |
| 6,034,054 A | 3/2000 | DeFelippis |
| 6,100,376 A * | 8/2000 | Dorschug ..................... 530/303 |
| 6,268,335 B1 | 7/2001 | Brader |
| 6,528,486 B1 | 3/2003 | Larsen et al. |
| 6,852,694 B2 | 2/2005 | Van Antwerp et al. |
| 7,022,674 B2 | 4/2006 | DeFelippis |
| 7,115,563 B2 | 10/2006 | Younis |
| 7,119,086 B2 | 10/2006 | Di Malta et al. |
| 7,192,919 B2 | 3/2007 | Tzannis et al. |
| 7,238,663 B2 | 7/2007 | DeFelippis et al. |
| 7,405,196 B2 | 7/2008 | Rosskamp et al. |
| 7,476,652 B2 * | 1/2009 | Brunner-Schwarz et al. . 514/1.1 |
| 7,544,656 B2 | 6/2009 | Sabetsky |
| 7,713,930 B2 * | 5/2010 | Brunner-Schwarz et al. . 514/1.1 |
| 7,803,763 B2 | 9/2010 | Thurow et al. |
| 7,807,242 B2 * | 10/2010 | Soerensen et al. ........... 428/35.7 |
| 7,918,833 B2 * | 4/2011 | Veasey et al. ................. 604/209 |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 2003/0026872 A1 | 2/2003 | Dake et al. |
| 2004/0048783 A1 | 3/2004 | Brunner-Schwarz et al. |
| 2004/0235710 A1 | 11/2004 | DeFelippis et al. |
| 2005/0106147 A1 | 5/2005 | Jordan et al. |
| 2005/0171009 A1 | 8/2005 | Brunner-Schwarz et al. |
| 2007/0128193 A1 | 6/2007 | O'Neil et al. |
| 2007/0135338 A1 | 6/2007 | O'Neil et al. |
| 2007/0237827 A1 | 10/2007 | Sung et al. |
| 2008/0248999 A1 | 10/2008 | Steiner |
| 2009/0088369 A1 | 4/2009 | Steiness |
| 2009/0099064 A1 | 4/2009 | Lougheed |
| 2009/0175840 A1 | 7/2009 | Kashyap et al. |
| 2009/0176692 A1 | 7/2009 | Habermann et al. |
| 2009/0214657 A1 | 8/2009 | Qazi |
| 2009/0312236 A1 | 12/2009 | Beals et al. |
| 2010/0029558 A1 | 2/2010 | Bristow |
| 2010/0055049 A1 | 3/2010 | Kuo et al. |

(Continued)

FOREIGN PATENT DOCUMENTS

| CN | 101454019 A | 6/2009 |
| DE | 102008053048 A1 | 4/2010 |

(Continued)

OTHER PUBLICATIONS

Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).*

(Continued)

*Primary Examiner* — Maury Audet
(74) *Attorney, Agent, or Firm* — McDonnell Boehnen Hulbert & Berghoff LLP

(57) ABSTRACT

The application relates to an aqueous pharmaceutical formulation comprising 200-1000 U/mL [equimolar to 200-1000 IU human insulin] of insulin glargine.

59 Claims, 12 Drawing Sheets

(56) References Cited

U.S. PATENT DOCUMENTS

| | | |
|---|---|---|
| 2010/0057194 A1 | 3/2010 | Ryan |
| 2010/0069292 A1 | 3/2010 | Pohl et al. |
| 2010/0069293 A1 | 3/2010 | Bolotin et al. |
| 2011/0020294 A1 | 1/2011 | Hammerman |
| 2011/0021423 A1 | 1/2011 | Olsen et al. |
| 2011/0118178 A1 | 5/2011 | Silvestre et al. |
| 2011/0118180 A1 | 5/2011 | Silvestre et al. |
| 2011/0152185 A1 | 6/2011 | Plum et al. |
| 2011/0230402 A1 | 9/2011 | Johansen et al. |
| 2011/0236925 A1 | 9/2011 | Hazra et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0012433 A1 | 1/2013 | Rosskamp et al. |
| 2013/0096059 A1 | 4/2013 | Stechl et al. |
| 2014/0206611 A1 | 7/2014 | Sanofi |

FOREIGN PATENT DOCUMENTS

| | | |
|---|---|---|
| EA | 006019 B1 | 8/2005 |
| EP | 2 389 945 A1 | 11/2011 |
| EP | 2 329 848 B1 | 10/2012 |
| EP | 2 387 989 B1 | 7/2014 |
| JP | 2005-508895 A | 4/2005 |
| JP | 2005-532365 A | 10/2005 |
| RU | 2008116057 A1 | 10/2009 |
| WO | WO 95/24183 | 9/1995 |
| WO | WO00072582 | 11/2000 |
| WO | 01/04156 A1 | 1/2001 |
| WO | WO 02/24214 A2 | 3/2002 |
| WO | WO03/105888 | 12/2003 |
| WO | WO2004064862 | 8/2004 |
| WO | WO 2007/050656 A1 | 5/2007 |
| WO | WO2008/013938 | 1/2008 |
| WO | WO 2008/124522 A2 | 10/2008 |
| WO | WO2009063072 | 5/2009 |
| WO | WO2009/089181 A1 | 7/2009 |
| WO | 2004/078196 A1 | 9/2009 |
| WO | 2004/078197 A1 | 9/2009 |
| WO | 2004/078198 A1 | 9/2009 |
| WO | WO2009/143014 A1 | 11/2009 |
| WO | WO2010/092163 | 8/2010 |
| WO | WO2011012719 | 3/2011 |
| WO | WO2011058082 | 5/2011 |
| WO | WO2011058083 | 5/2011 |
| WO | WO 2011/103575 A1 | 8/2011 |
| WO | WO 2011/122921 A2 | 10/2011 |
| WO | WO 2011/128374 A1 | 10/2011 |
| WO | WO 2011/144673 A2 | 11/2011 |
| WO | WO 2011/144674 A2 | 11/2011 |
| WO | WO 2011/157402 A1 | 12/2011 |
| WO | WO 2011/160066 A1 | 12/2011 |
| WO | WO2011147980 | 12/2011 |
| WO | WO2012028172 | 3/2012 |
| WO | WO 2012/055967 A2 | 5/2012 |
| WO | WO 2012/065996 A1 | 5/2012 |
| WO | WO 2012/066086 A1 | 5/2012 |
| WO | WO2012104342 | 8/2012 |
| WO | WO 2012/125569 A2 | 9/2012 |

OTHER PUBLICATIONS

European Public Assessment Report (EPAR) Optisulin EPAR summary for the public. Last updated in Feb. 2009 (Filed by Applicant as Exhibit A on Mar. 10, 2016).*

Written Opinion issued in Japanese Application 2013-97274, dated Oct. 30, 2014, pp. 1-9 (only English translation submitted).

Office Action issued in European Application No. 11 720 115.2, dated Dec. 22, 2014, pp. 1-6.

Substantive Examination issued in Kenyan Application No. KE/P/2012/001703, dated Dec. 10, 2014, one page.

Chatterjee, et al., Expert Opin Pharmacother (2006) 7(10): pp. 1357-1371.

Werner U., et al. "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).

Office Action for Canadian Patent Application No. 2,792,669 of Oct. 27, 2014, pp. 1-4.

First Office Action for Chinese Patent Application No. 201110225117.6 of Aug. 18, 2014, pp. 1-5 (in Chinese, submitted with English-language correspondence describing the rejections contained in the First Office Action prepared Sep. 17, 2014, pp. 1-3).

Canadian Office Action dated Feb. 18, 2014 in Canadian Patent Appln. No. 2,792.669.

Shubert-Zsilavecz, et al., "Insulin glargin—ein langwirksames Insulinanalogon", Nr. 2, 30, Jahrgang 2001, Pharmzie in unserer Zeit, pp. 125-130 with English language abstract.

Treyce S. Knee, MD, et al, "A Novel Use of U-500 Iunsulin for Continuous Subcutaneous Insulin Infusion in Patients With Insulin Resistance: A Case Series", Endocrine Practice, vol. 9, No. 3 May/Jun. 2003, pp. 181-186.

18th World Health Congress (Helsinki), WMA Declaration of Helsinki—Ethical Principles for Medical Research Involving Human Subjects; WMA; Jun. 1964.

Organization for Economic Co-Ooperation and Development; OECD Principles of Good Laboratory Practice and Compliance Monitoring (as revised in 1997); ENV/MC/CHEM (98) 17; Jan. 21, 1998; pp. 1-41.

Fieller E.G., Symposium on Interval Estimation; Some Problems with Interval Estimation; No. 2; 1954; pp. 175-185.

American Diabetes Association; Report of the Expert Committee on the Diagnosis and Classifcation of Diabetes Mellitus; Diabetes Care, vol. 21, Supplement 1, Jan. 1998; pp. S5-S19.

Sampson, H.A., et al.; Second Symposium on the definition and management of anaphylaxis: Summary report—Second National Institute of Allergy and Infectious Disease/Food Allergy and Anaphylaxis network symposium; J. Allergy Clin Immunol; Feb. 2006; pp. 391-397.

Gough, K., et al.; Assessment of Dose Proportionality: Report from the Statisticians in the Pharmaceutical Industry/Pharmacokinetics UK Joint Working Party; Drug Information Journal, vol. 29, 1995, pp. 1039-1048.

Ex Parte Herrmann, Appeal No. 2009-001777 U.S. Appl. No. 10/616,457 (B.P.A.I. Nov. 13, 2009).

U.S. Appl. No. 13/310,118, filed Dec. 2, 2011.

Office Action in corresponding Korean Patent Appl. No. 10-2012-7026802, dated Jun. 26, 2014 with English language translation.

Office Action in Algerian Application 120783, of Apr. 2, 2014, one page (in French, English translation submitted).

Office Action in Columbia Application 12 201607, of Jun. 25, 2014, pp. 1-5 (English summary submitted).

First Examination Report in New Zealand Application 602541, of May 28, 2013, pp. 1-2.

Office Action in Peru Application 002170-2012/DIN, of Dec. 16, 2013 pp. 1-2 (English summary submitted).

Extended EPO Search Report from EP Application EP 14 16 6877.2, of Aug. 18, 2014, pp. 1-6.

EPO Communication in EP Application EP 11 72 0115.2, Jan. 4, 2013, pp. 1-2.

First Office Action in Chinese Application 201110 225117.6, of Dec. 4, 2013, pp. 1-5 (English summary submitted).

JPO First Office Action in Japanese Application 2013-97274, of dated Jul. 1, 2014, pp. 1-4 (English translation submitted).

TIPO First Office Action in Taiwanese Application 1 00 117 134, of Dec. 24, 2013, pp. 1-8 (English summary submitted).

TIPO Further Office Action in Taiwanese Application 1 00 117 134, of May 8, 2014, pp. 1-3 (English summary submitted).

Canadian Office Action dated Dec. 7, 2012 issued in Application No. 2,792,669.

(56) References Cited

OTHER PUBLICATIONS

European Office Action dated Nov. 30, 2012 issued in Application No. 11 166 415.7.
Garg, R. et al., "U-500 insulin: why, when and how to use in clinical practice", Diabetes/Metabolism Research and Reviews, (2007), vol. 23, pp. 265-268.
International Search Report dated Mar. 22, 2012 issued in International Application No. PCT/EP2011/058079.
Jorgensen, K.H. et al., "Five fold increase of insulin concentration delays the absorption of subcutaneously injected human insulin suspension in pigs", Diabetes Research and Clinical Practice, (2000), vol. 50, pp. 161-167.
Notice of Reason(s) for Rejection dated Dec. 11, 2012 issued in Japanese Patent Application No. 2011-110037, together with English-language translation.
Panamanian Office Action dated May 24, 2012 issued in Application No. 89284-01 (English translation).
Pakistani Office Action dated Jan. 28, 2013 issued in Pakistan Patent Application No. 350/2011 (English translation).
U.S. Appl. No. 13/633,496, filed Oct. 2, 2012.
Wafa, W.S. et al., "Use of U-500 Regular Insulin in Type 2 Diabetes", Diabetes Care, (2006), vol. 29, No. 9, pp. 2175-2176.
Pakistani Office Action dated Apr. 22, 2013 issued in Pakistani Patent Application No. 350/2011.
Canadian Office Action dated Jul. 26, 2013 issued in Canadian Patent Application No. 2,792,669.
Australian Office Action dated Apr. 23, 2013 issued in Australian Patent Appln. No. 2012216648.
Venezuelan Office Action dated Sep. 25, 2013 issued in Venezuelan Patent Appln. No. 2011-000648.
Peruvian Office Action dated Sep. 13, 2013 issued in Peruvian Patent Appln. No. 002170-2012/DIN.
Christensen, M., Lixisenatide, A Novel GLP-1 Receptor Agonist for the Treatment of Type 2 Diabetes Millitus, IDrugs, (Aug. 2009), vol. 12, No. 8, pp. 503-513.
Costa Rican Opposition to Costa Rican Patent Appln. No. 2012-0578; La Gaceta Publication of Mar. 6, 2013.
Colombian Opposition to Patent Appln. No. 12 201 607; Aug. 7, 2013.
Ecuadorian Opposition to Ecuadorian Patent Appln. No. SP 2012-12298; Nov. 16, 2012.
Ecuadorian Opposition to Ecuadorian Patent Appln. No. SP 2012-12298; Jun. 17, 2013.
Lando, H., "The New Designer Insulins", Clinical Diabetes, (2000), vol. 4, (http://journal.diabetes.org/clinical diabetes/V18N42000/pg154.htm).
Tews, D. et al., "Enhanced Protection against Cytokine- and Fatty Acid induced Apoptasis in Pancreatic Beta Cells by Combined Treatment with Glucagon-like Peptide-1 Receptor Agonists and Insulin Analogues", Hormone and Metabolic Research, vol. 40, pp. 172-180, 2008.
Colino, E. et al., "Therapy with insulin glargine (Lantus) in toddlers, children and adolescents with type 1 diabetes," Diabetes Research and Clinical Practice (2005), vol. 70, pp. 1-7.
Arnolds, Sabine et al., "Insulin Glargine (GLAR) plus Metformin (MET): An Efficacious and Safe Regimen That Can Be Combined with Exenatide (EXE) or Sitagliptin (SITA)," Diabetes, American Diabetes Association (2009), vol. 58, p. A141.
Yki-Jarvinen, H. et al., "Insulin glargine or NPH combined with metformin in type 2 diabetes: the LANMET study," (2006), vol. 49, No. 3, pp. 442-451.
European Search Report dated Nov. 16, 2010 issued in EP10305780.
Cochran, Elaine et al., "The Use of U-500 in Patients with Extreme Insulin Resistance", Diabetes Care, vol. 28, No. 5, May 2005.
De Le Pena, Amparo, "Pharmacokinetics and Pharmadynamics of High-Dose Human Regular U-500 Insulin Versus Human Regular U-100 Insulin in Healthy Obese Subjects", Diabetes Care, vol. 34, Dec. 2011.
Australian Office Action issued in Australian Patent Appln. No. 2011202239 dated Sep. 22, 2011.

http://diabetes.emedtv.com/lantus/generic-lantus.html.
Secnik Boye, Kristina et al., "Patient-reported outcomes in a trial of exenatide and insulin glargine for the treatment of type 2 diabetes," Health and Quality of Life Outcomes (2006), vol. 4, No. 80, pp. 1-8.
HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.
European Search Report dated Mar. 12, 2012 issued in EP11166415.
Sanofi's Lantus Draft Prescribing Information/Package Insert; (around the time of U.S. FDA approval); NDA 21-081 Draft package insert (Sponsor revision #5) Date of submission: Apr. 20, 2000; sehttp://www.drugbank.ca/system/fda_labels/DB00047.pdf; see entire poster, esp. "Background" section.
Johnson et al. When is a unit of insulin not a unit of insulin? Detemir dosing in type 2 diabetes. 2008. http://professional.diabetes.org/Content/Posters/2008/p8-LB.pdf; see entire poster, esp. "Background" section.
Sanofi's Lantus Draft Prescribing Information/Package Insert: (around the lime of U.S. FDA approval): NDA 21-081 Draft package insert (Sponsor revision #5) Date of submission: Apr. 20, 2000; see http://www.drugbank.ca/system/fds_labels/DB00047.pdf 1265922812, pp. 1-14.
Ecuadorian Opposition filed by PROCAPS to Ecuadorian Patent Application No. SP 2012-12298; dated Jun. 17, 2013, pp. 1-8 (English translation submitted).
Ecuadorian Opposition filed by ALAFAR to Ecuadorian Patent Application No. SP 2012-12298; dated Jun. 17, 2013, pp. 1-16 (English translation submitted).
Request for "Type C" Meeting letter, sent by Michael Lutz, addressed to Mary Parks, dated Apr. 21, 2006, pp. 1-10.
Sanofi Press Release entitled "FDA Accepts Sanofi's New Drug Application for Basal Insulin Toujeo®," dated Jul. 8, 2014, pp. 1-2.
Sanofi Press Release entitled "Sanofi Receives FDA Approval of Once-Daily Basal Insulin Toujeo®," dated Feb. 26, 2015, pp. 1-4.
Goykhman et al., "Insulin Glargine: a review 8 years after its introduction." Expert Opin. Pharmacother. 10(4):705-18 (2009).
English translation of Search Report for Chinese Patent Application No. 20140220537.9; dated Feb. 13, 2015, pp. 1-2.
Final Rejection issued in U.S. Appl. No. 13/110,568; mailed Feb. 21, 2013, pp. 1-20.
Non-Final Rejection issued in U.S. Appl. No. 13/110,568; mailed Mar. 19, 2012, pp. 1-18.
Non-Final Rejection issued in U.S. Appl. No. 13/310,118, mailed Mar. 25, 2015, pp. 1-15.
Non-Final Rejection issued in U.S. Appl. No. 13/310,118, mailed Mar. 29, 2013, pp. 1-21.
Final Rejection issued in U.S. Appl. No. 13/310,118; mailed Aug. 2, 2012, pp. 1-20.
Non-Final Rejection issued in U.S. Appl. No. 13/310,118; mailed Mar. 19, 2012, pp. 1-19.
Non-Final Rejection issued in U.S. Appl. No. 14/624,575; mailed Mar. 26, 2015, pp. 1-14.
U.S. Appl. No. 13/310,118, filed Dec. 2, 2011 to Becker et al.
U.S. Appl. No. 14/624,575, filed Feb. 17, 2015 to Becker et al.
Written Opinion of the International Searching Authority for International Application No. PCT/EP2011/058079, mailed Mar. 22, 2012, pp. 1-8.
Substantive Examination Report for Application No. Invention 1/2012/501895 in the Philippines, mailed Feb. 20, 2015, one page.
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Buse et al., "Use of twice-daily exenatide in Basal insulin-treated patients with type 2 diabetes: a randomized, controlled trial." Annals of Internal Medicine 154(2):103-12 (Jan. 2011).
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.

(56) References Cited

OTHER PUBLICATIONS

Mikhail, "Is liraglutide a useful addition to diabetes therapy?" Endocr Practice 16(6):1028-37 (Nov.-Dec. 2010).

NCT01195454, NIH Clinical Trials, "Euglycemic clamp dose-response study comparing insulin glargine U300 with Lantus U100" last updated Dec. 13, 2010, pp. 1-4.

Werner et al., "Pharmacological profile of lixisenatide: A new GLP-1 receptor agonist for the treatment of type 2 diabetes." Regulatory Peptides 164(2-3):58-64 (Epub Jun. 2, 2010).

Kielgast et al., "Treatment of type 1 diabetic patients with glucagon-like peptide-1 (GLP-1) and GLP-1R agonists." Curr Diabetes Rev. 5(4):266-75 (Nov. 2009).

Starkova, ed., "Clinical Endocrinology", Guide for physicians, Moscow, "Medicine", 1991, p. 231-252.

ADA Workgroup Report, "Defining and Reporting Hypoglycemia in Diabetes, A report from the American Diabetes Associate Workgroup on Hypoglycemia" Diabetes Care 28(2):1245-49 (May 2005).

European Medicines Agency—Science Medicines Health, "Guideline on clinical investigation of medicinal products in the treatment of diabetes mellitus" Committee for Medicinal Products for Human Use, Jan. 20, 2010, pp. 1-19.

International Search Report and Written Opinion of the International Searching Authority in International Application No. PCT/EP2014/056498; mailed Jun. 25, 2014, pp. 1-10.

Extended European Search Report from Application No. EP 13 30 5432.0; mailed Sep. 13, 2013, pp. 1-5.

EMA—Science Medicines Health "Toujeo" EPAR Summary for the Public, first published Nov. 5, 2009, pp. 1-3.

European Medicines Agency, "Toujeo (previously Optisulin) insulin glargine," <http://www.ema.europa.eu/ema/index.jsp?curl=pages/medicines/human/medicines/000309/human_med_000955.jsp&mid=WC0b01ac058001d124>, last updated Jan. 25, 2016, visited Feb. 3, 2016, pp. 1-6—screenshot of "About" tab of webpage and printouts of "About" tab of webpage with listed items collapsed and expanded.

\* cited by examiner

LONG-ACTING FORMULATIONS OF INSULIN

This application is a continuation application of U.S. Ser. No. 13/110,568, filed May 18, 2011, which claims benefit to U.S. Provisional Appln. No. 61/411,608, filed Nov. 9, 2010 and 61/429,936, filed Jan. 5, 2011.

The application relates to an aqueous pharmaceutical formulation comprising 200-1000 U/mL [equimolar to 200-1000 IU human insulin] of insulin glargine, and its use.

Insulin glargine is $31^B$-$32^B$-Di-Arg human insulin, an analogue of human insulin, with further substitution of asparagine in position A21 by glycine.

Lantus® is an insulin product containing insulin glargine providing 24 hour basal insulin supply after single dose subcutaneous injection.

The glucodynamic effect of Lantus® is distinguished from other currently marketed insulin products by virtue of a delayed and predictable absorption of insulin glargine from the subcutaneous injection site resulting in a smooth, 24 hour time-concentration and action profile without a definite peak. Lantus® was developed to meet the medical need for a long-acting insulin product that can be administered as a single daily injection to yield normal or near-normal blood glucose control with a basal insulin profile that is as smooth as possible over a 24-hour period. Such a preparation provides good control of blood glucose all day, while minimizing the tendency to produce hypoglycemia seen with other insulin preparations with a more definite "peak" effect.

A considerable number of patients, in particular those with increased insulin resistance due to obesity, use large doses to control blood glucose. For example, a dose of 100 U requires injection of 1 mL Lantus® U100, which may confer some discomfort; each mL Lantus® U100 contains 100 U (3.6378 mg) insulin glargine. To reduce the volume of injection, a formulation containing 300 U insulin glargine per mL has been developed. Although the invention is not limited to an insulin glargine U 300 formulation, the clinical studies described herein were performed with an insulin glargine U 300 formulation; each mL insulin glargine U300 contains 300 U (10.9134 mg) insulin glargine. This formulation would allow patients to inject the same number of units of insulin glargine at one third the volume of injection.

Both insulin glargine formulations, U100 and U300, were expected to provide the same insulin exposure and the same effectiveness, i.e. time profiles.

FIGURES

The figures below effectively show the surprising and unexpected differences in exposure (PK) and activity (PD) between Lantus U100 und Lantus U300 formulations (insulin glargine U100 und insulin glargine U300 formulations) after the same s.c. dose given to healthy subjects, at the same time as blood glucose (PD) was constant.

BRIEF DESCRIPTION OF THE DRAWINGS

FIG. 6A: insulin glargine concentration (mU/L), FIG. 6B: blood glucose (BG, mg/dL), FIG. 6C: glucose infusion rate (GIR, mg·kg$^{-1}$·min$^{-1}$). The curves display LOWESS smoothed averages of all data points of all subjects (population averages); LOWESS is a data analysis technique for producing a "smooth" set of values from a time series which has been contaminated with noise, or from a scatter plot with a "noisy" relationship between the 2 variables.

FIG. 7: Legend: Profiles 1 to 3 (from top to bottom).

Results of a randomized, double-blind, parallel group dose response study of 0.4, 0.6 and 1.2 U/kg Lantus® U100 (insulin glargine U100) in patients with diabetes mellitus type 1 using the euglycemic clamp technique.

Figure 1:
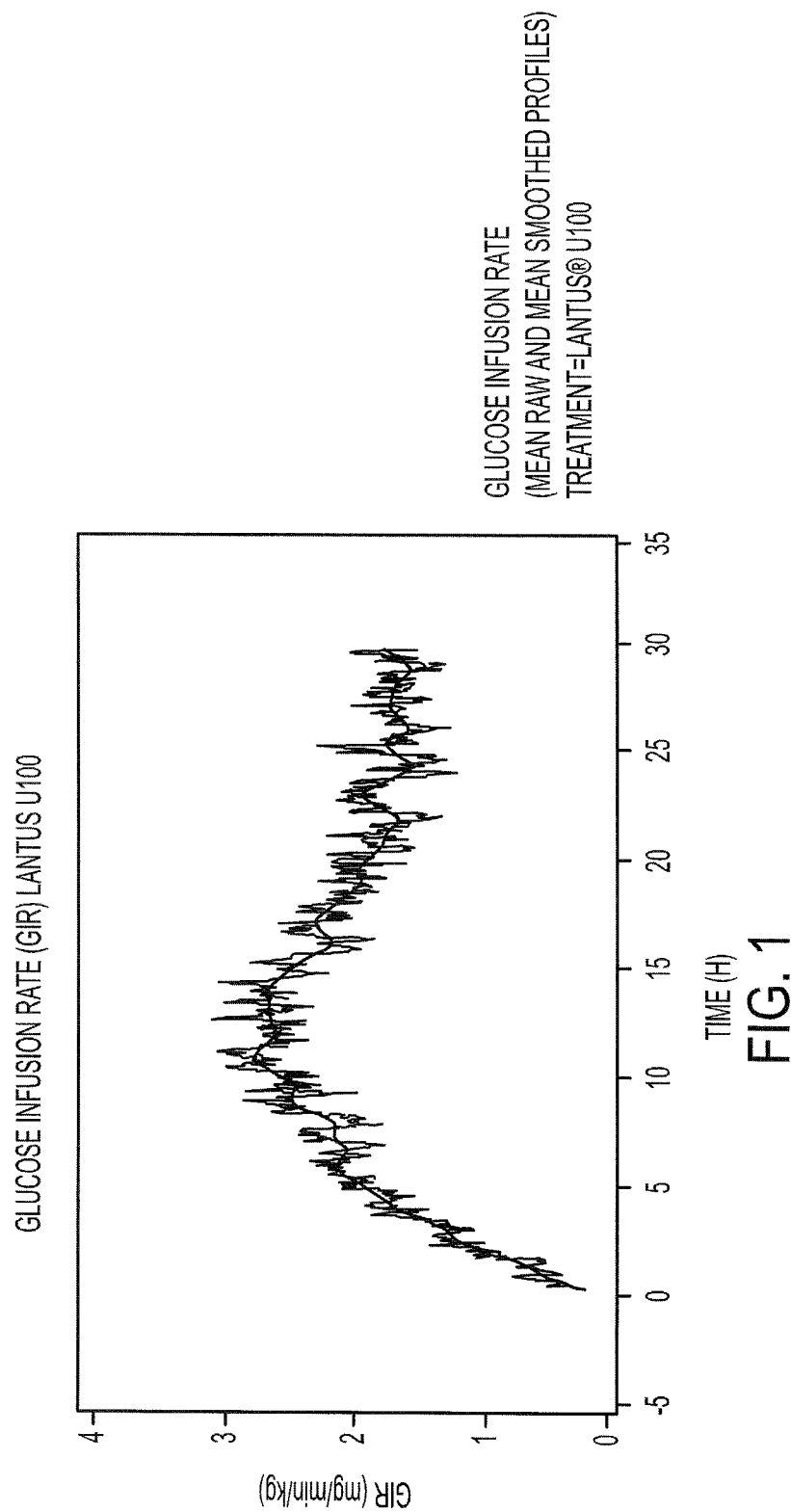
FIG. 1: Glucose Infusion Rate (GIR) Lantus U100.
Figure 2:
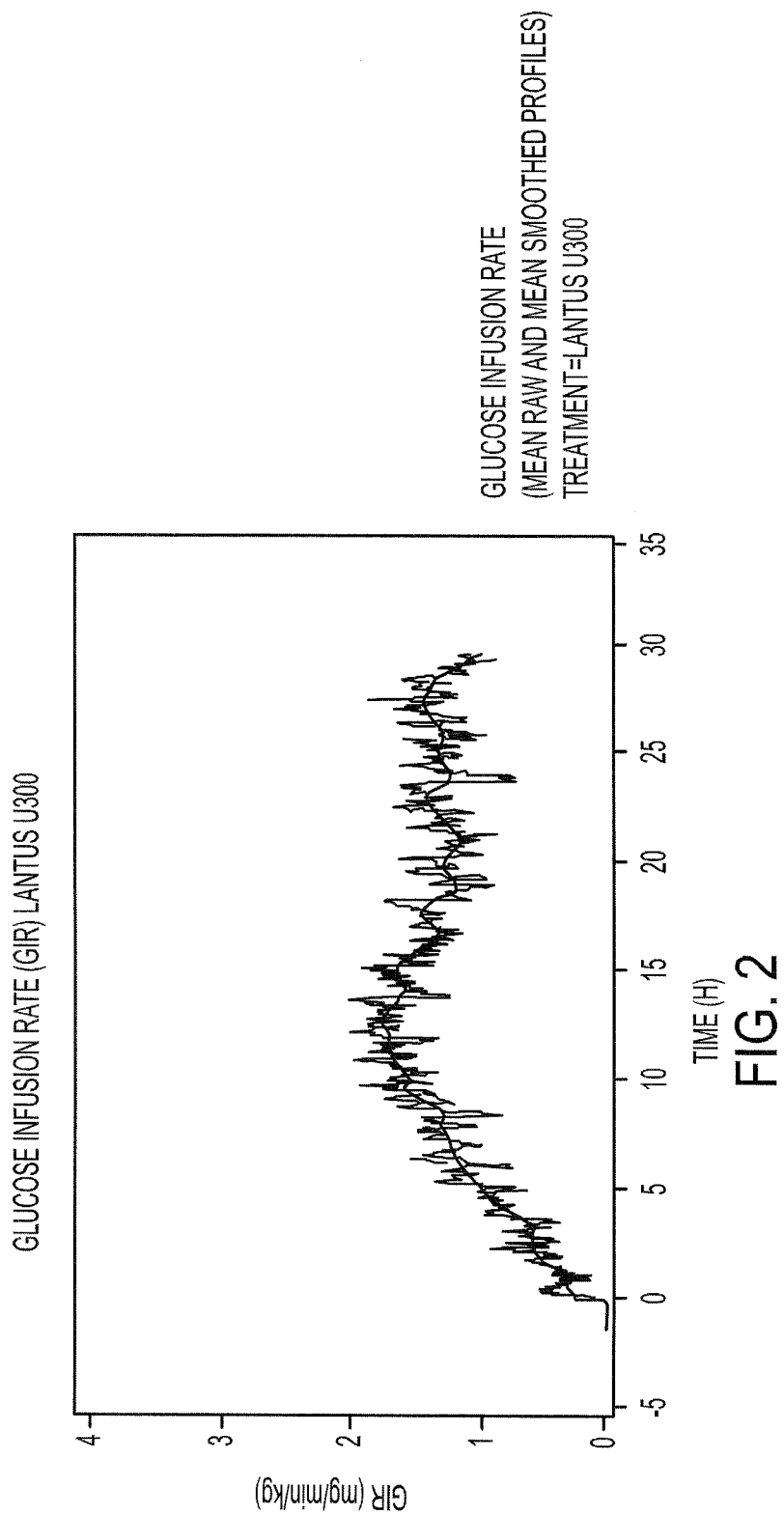
FIG. 2: Glucose Infusion Rate (GIR) Lantus U300.
Figure 3A:
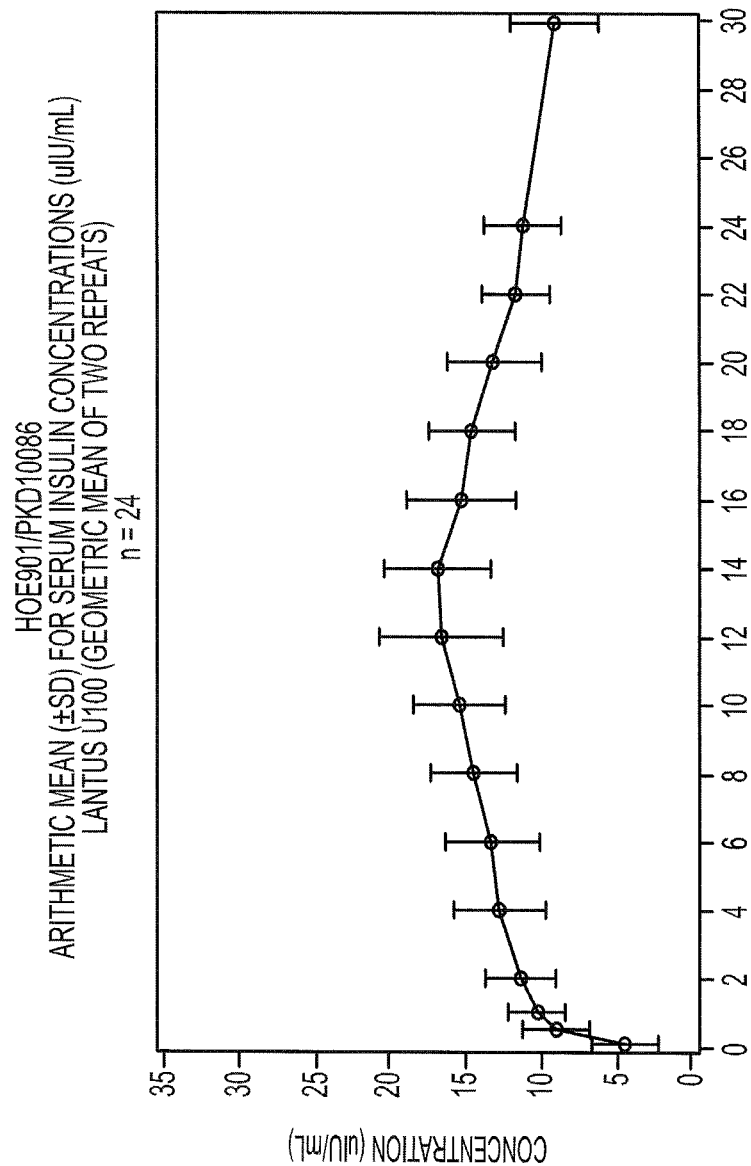
FIGS. 3A and 3B: Serum Insulin Concentrations; Lantus U100 (3A) and U300 (3B).
Figure 3B:
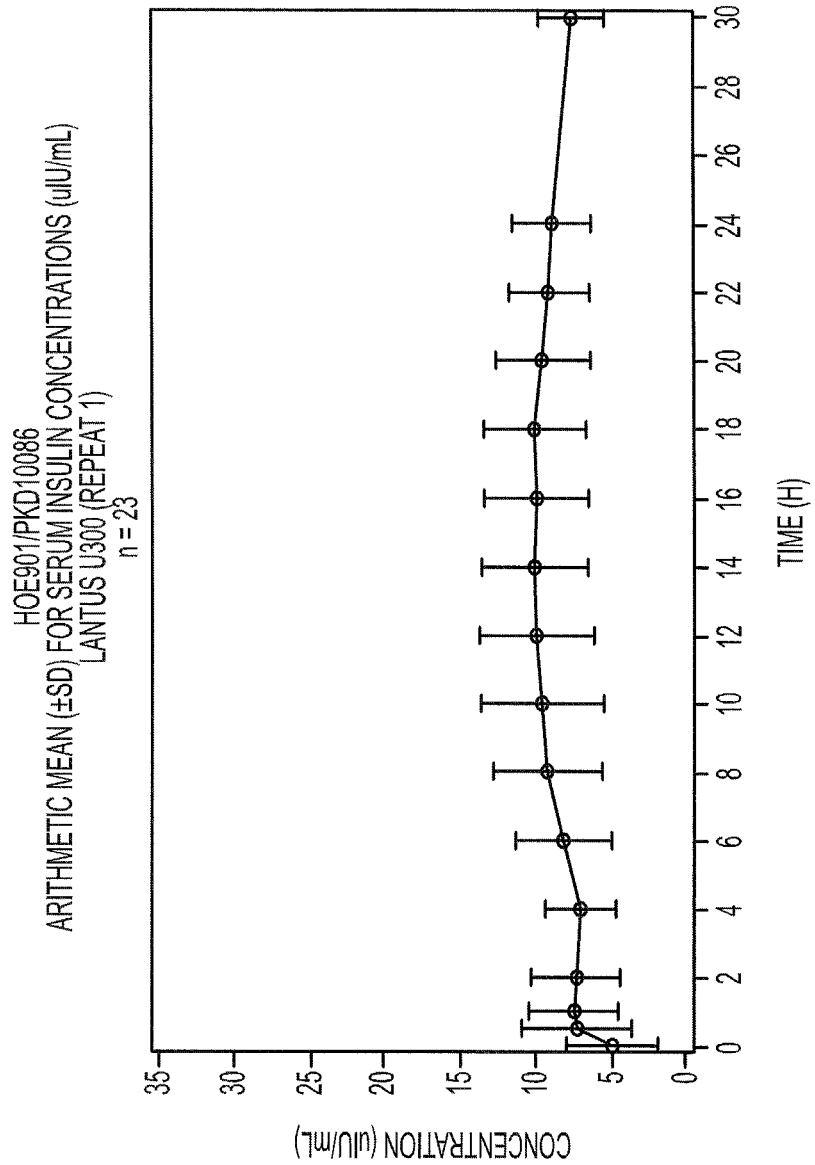
Figure 4A:
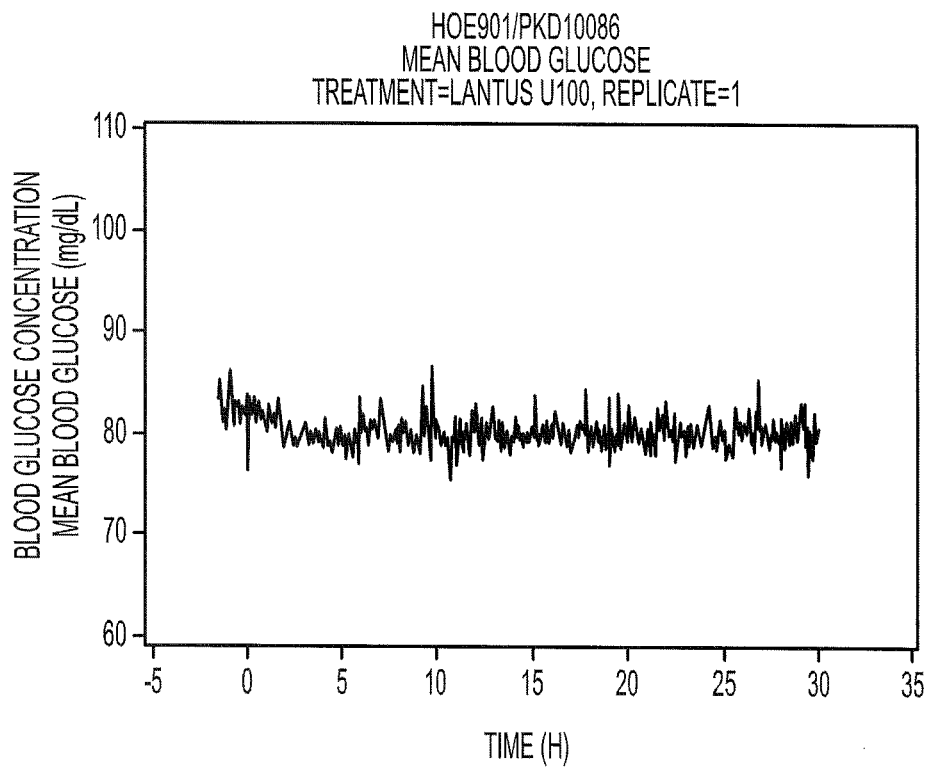
FIGS. 4A and 4B: Blood Glucose U100; (4A) replicates=1, (4B) replicates=2.
Figure 4B:
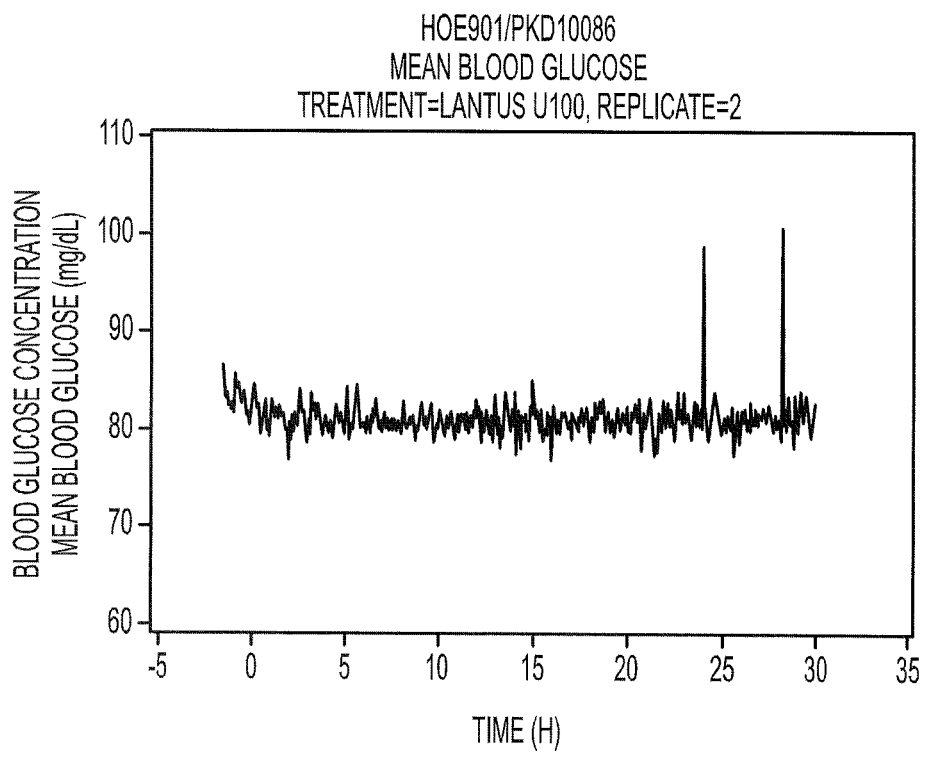
Figure 5A:
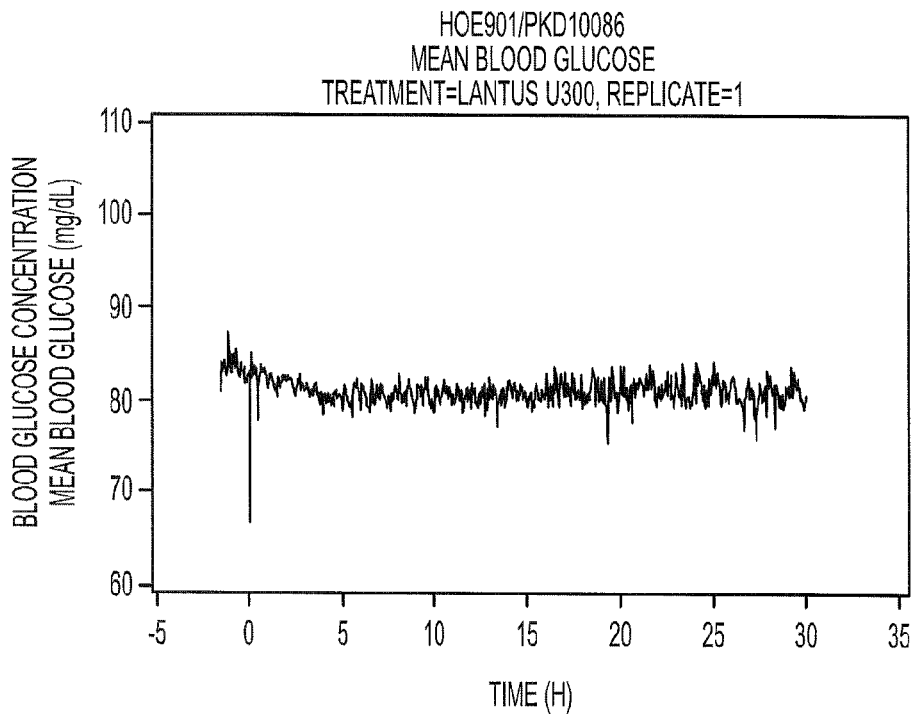
FIGS. 5A and 5B: Blood Glucose U300; (5A) replicates=1, (5B) replicates=2.
Figure 5B:
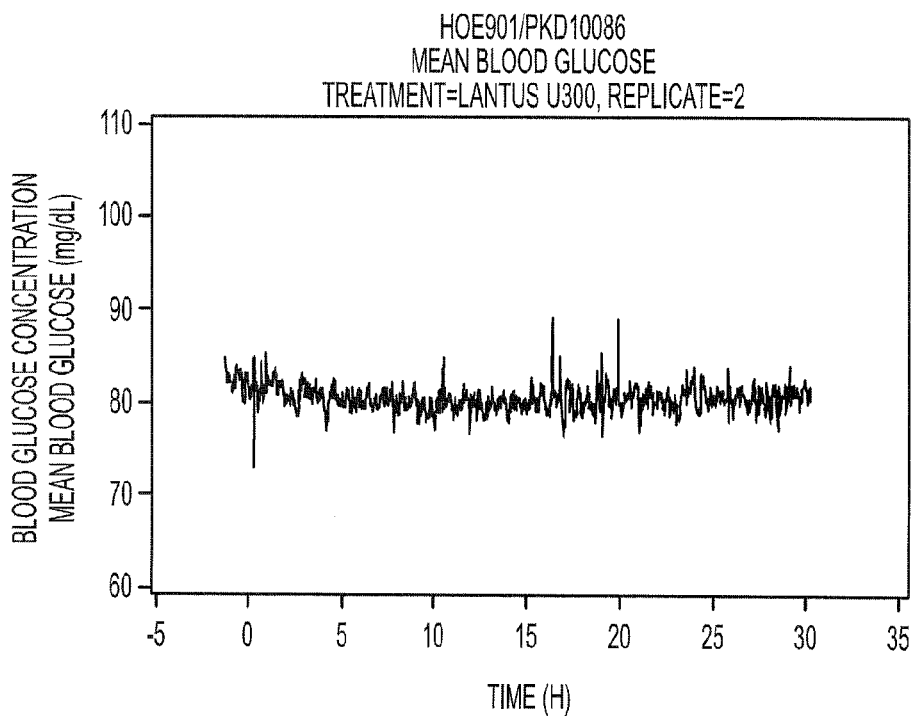
Figure 6A:
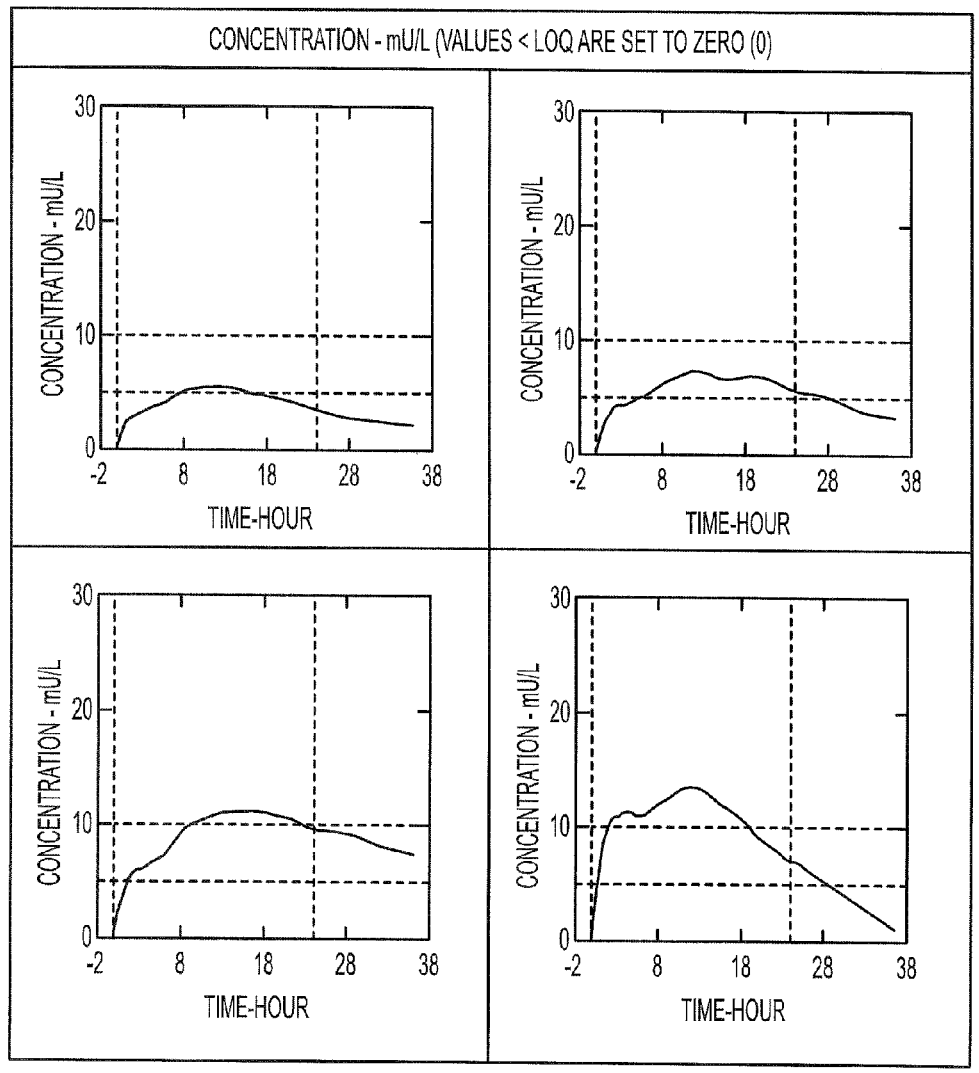
FIGS. 6A, 6B and 6C: Results of a randomized, 4-sequence, cross-over, double-blind, dose response study of 0.4, 0.6 and 0.9 U/kg HOE-901-U300 (insulin glargine U300) compared to 0.4 U/kg Lantus® U100 (insulin glargine U100) in patients with diabetes mellitus type 1 using the euglycemic clamp technique.
Figure 6B:
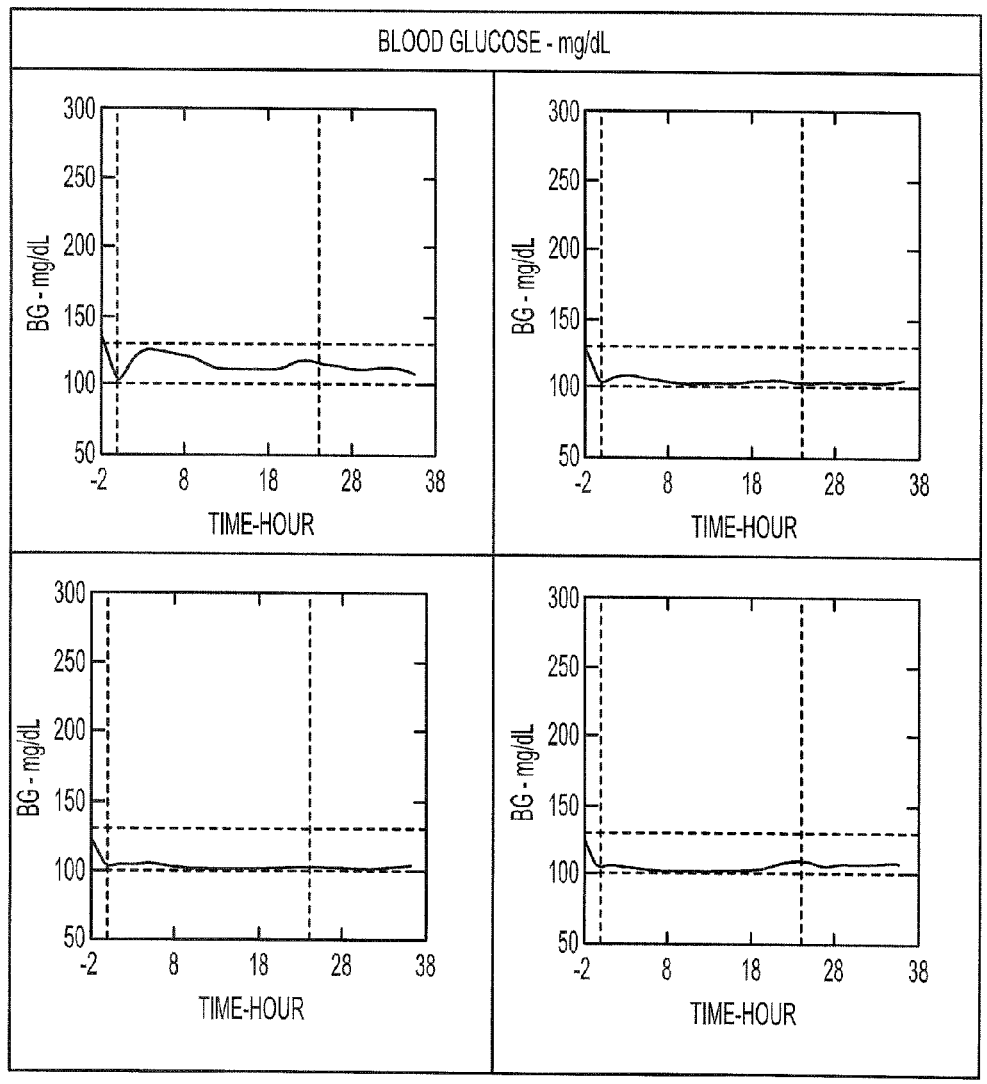
Figure 6C:
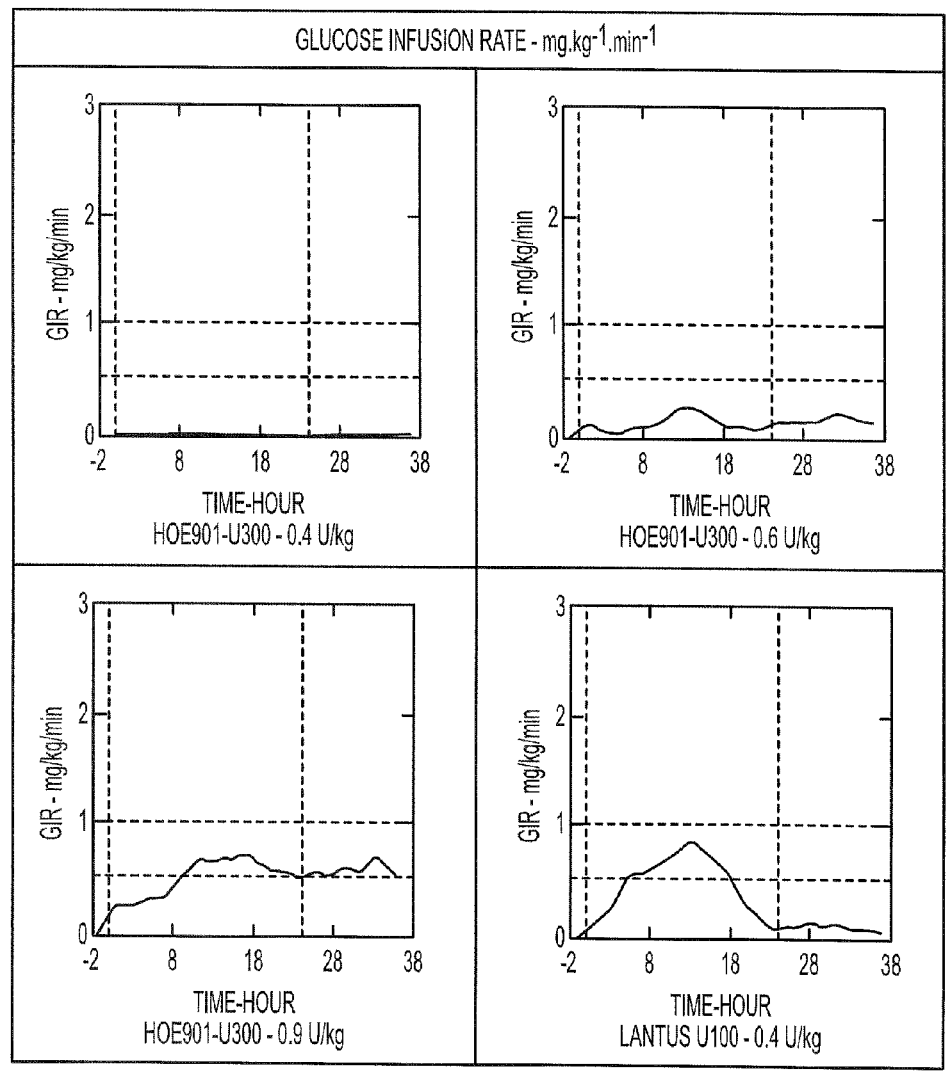
Figure 7:
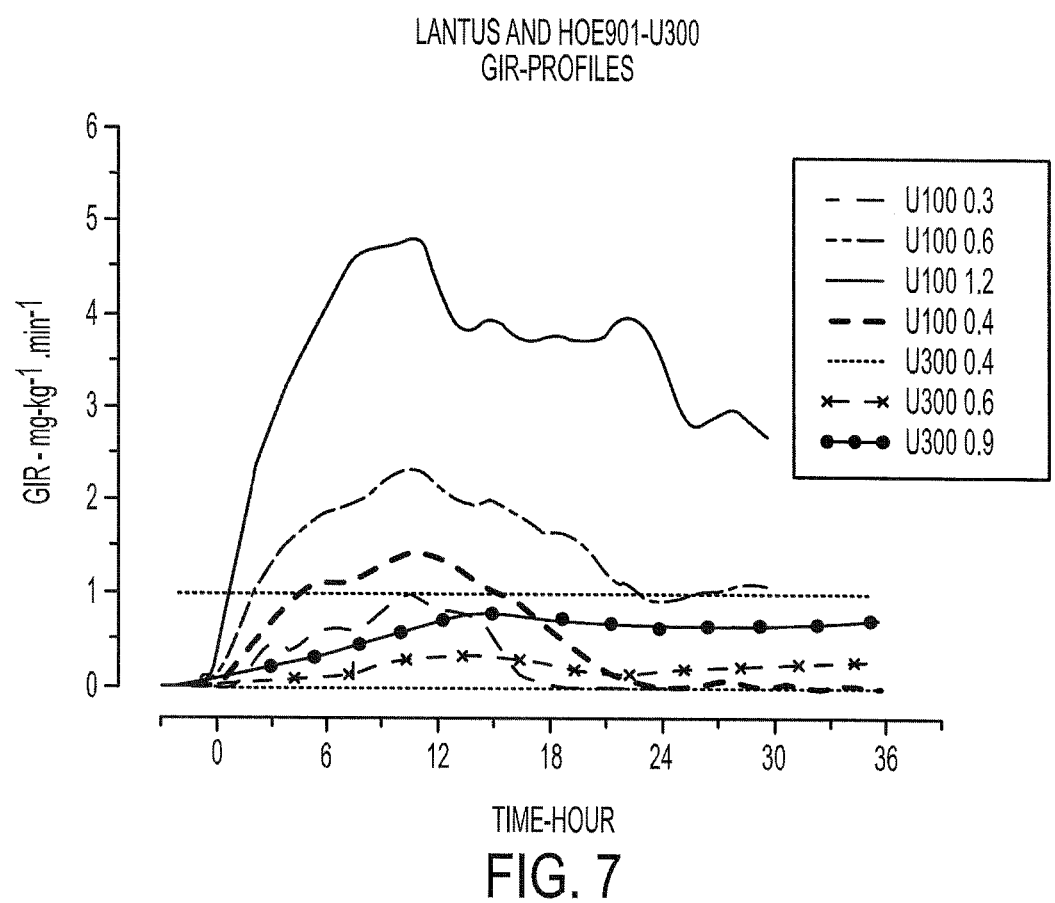
FIG. 7: Glucose infusion rate (GIR, mg·kg$^{-1}$·min$^{-1}$). The curves display LOWESS smoothed averages of all data points of all subjects (population averages); LOWESS is a data analysis technique for producing a "smooth" set of values from a time series which has been contaminated with noise, or from a scatter plot with a "noisy" relationship between the 2 variables.

FIG. 7: Legend: Profiles 4 to 7 (from top to bottom).

Results of a randomized, 4-sequence, cross-over, double-blind, dose response study of 0.4, 0.6 and 0.9 U/kg HOE-901-U300 (insulin glargine U300) compared to 0.4 U/kg Lantus® U100 (insulin glargine U100) in patients with diabetes mellitus type 1 using the euglycemic clamp technique.

Figure 8A:
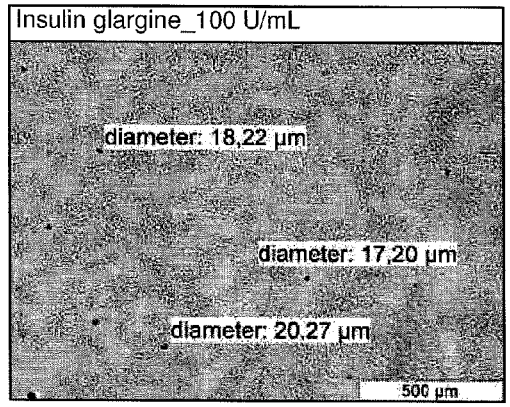
Figure 8B:
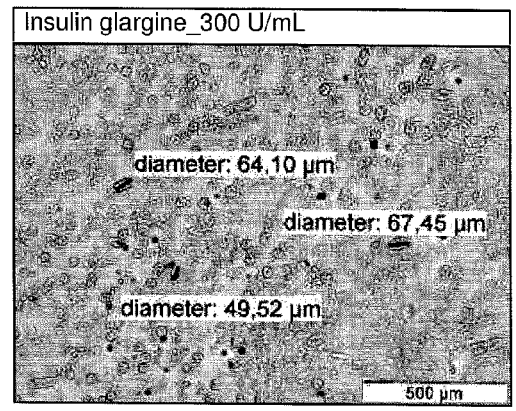
Figure 8C:
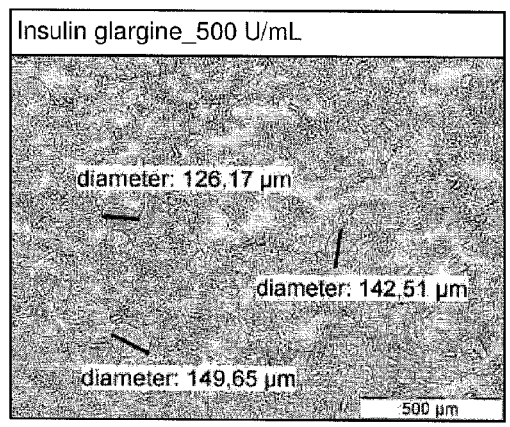
Figure 8D:
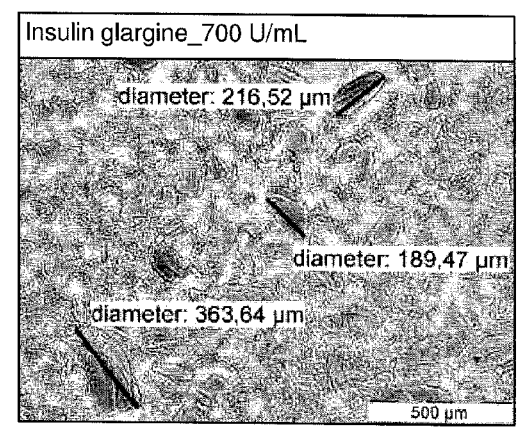
Figure 8E:
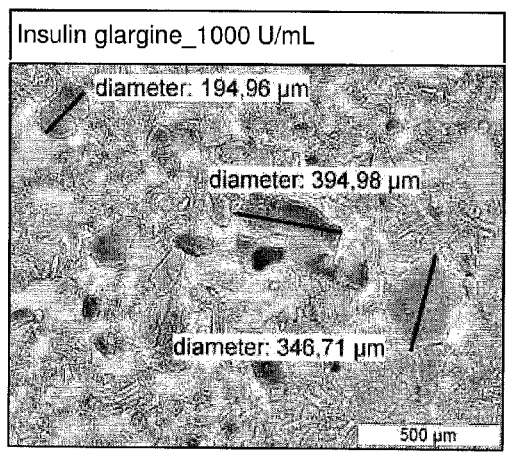

FIGS. 8A, 8B, 8C, 8D and 8E: Optical microscope pictures of precipitates of insulin glargine formulations with increasing concentrations:

FIG. 8A: 100 U/mL, FIG. 8B: 300 U/mL, FIG. 8C: 500 U/mL, FIG. 8D: 700 U/mL and FIG. 8E: 1000 U/mL, with the magnitude of 100× and including the maximum diameters.

All precipitations are performed with 60 U of insulin glargine.

Figure 9:
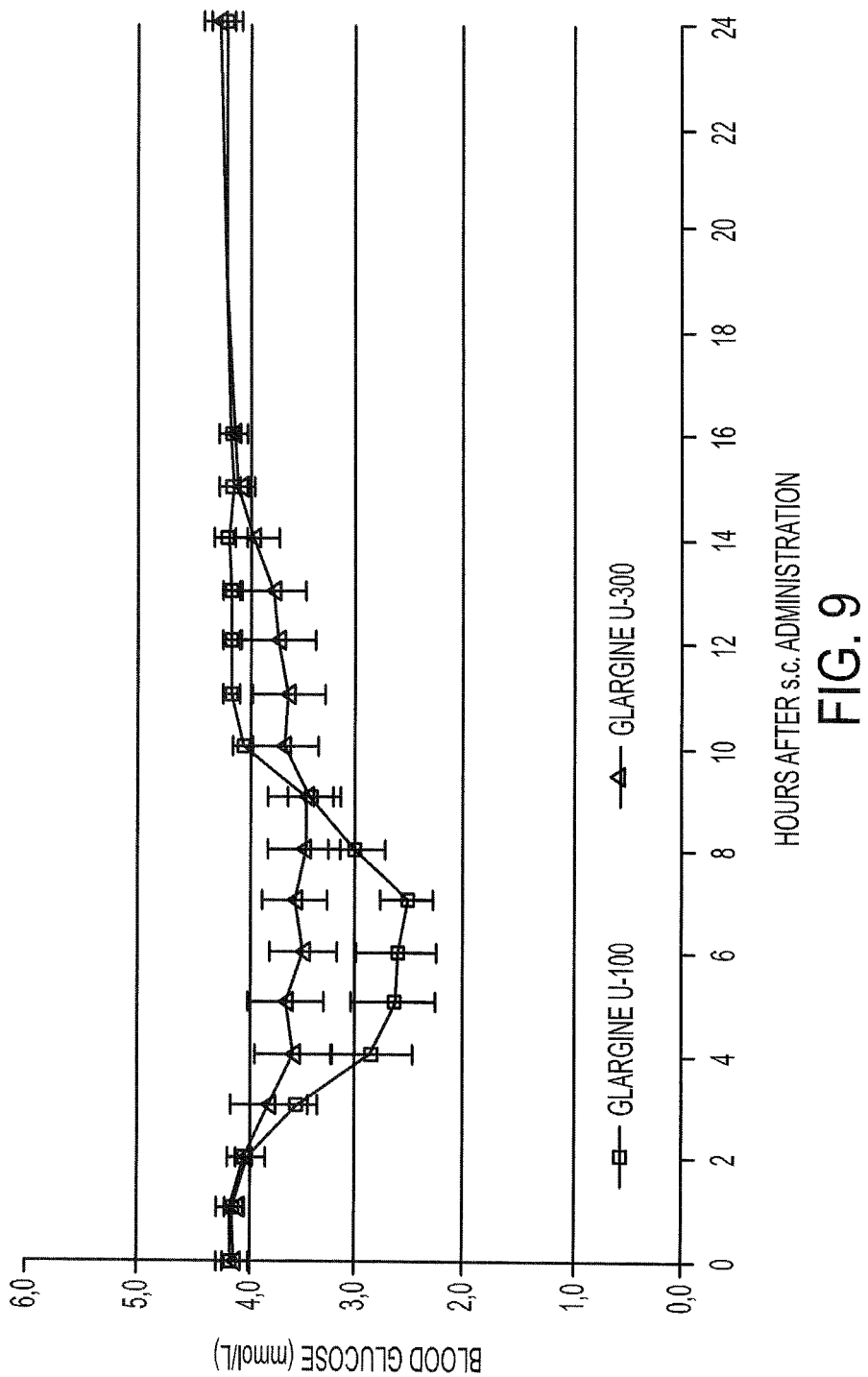

FIG. 9: Time-action profile of insulin glargine U-100 vs. U-300 in normoglycemic dogs.

DETAILED DESCRIPTION

Exposure and activity of insulin glargine U300, the test (T) medication, was tested in non-diabetic healthy subjects in euglycemic clamps for equivalence in exposure and activity to Lantus U100, the approved reference (R) product. To account for the long duration of action of insulin glargine after subcutaneous administration 30 hours were selected. Exposure was assessed from insulin glargine concentration time profiles after subcutaneous administration while activity was simultaneously assessed as glucose utilization per unit insulin.

A replicate design allowed limiting the number of subjects for assessing bioequivalence and variability as recommended by the FDA guideline "Guidance for Industry, Statistical Approaches to Establishing Bioequivalence".

The respective clinical study was expected to establish equivalence in exposure and activity.

A dose of 0.4 U/kg was selected for this study; it corresponds to the average basal insulin dose in patients. In non-diabetic healthy subjects this dose produces a sizeable elevation in plasma insulin concentration and a lasting glucose lowering effect that can be quantified in euglycemic clamp settings.

The replicate design favored by guidelines requires two replicate single dose injections of either IP (R: Lantus® U100, T: insulin glargine U300) in predefined four way crossover sequences (RTTR or TRRT) as allotted by the randomization plan. This was executed in Periods (P) 1-4 at four different days. As a result, each subject received two replicate single subcutaneous doses of 0.4 U/kg Lantus® U100 (R) and insulin glargine U300 (T), alternating between two opposite sites of the periumbilical area.

A washout period of 4 to 18 days separated each dosing day. The length of the wash-out period varied individually allowing both the participant and the Investigator to adjust to their needs. By experience, 4 days comprise a minimum period for recovery, enabling 1 clamp per week for a participant, while 18 days represent a break of 3 weeks between clamp days, allowing subjects more freedom to fulfill non-study related obligations.

Prior to the euglycemic clamp visits, at SCR (screening visit), subjects have been screened for eligibility, and in EOS (end-of-study) visit subjects have come in for a final examination to ensure normal health status. Screening and P1 have not be separated by more than 21 days, while the EOS visits occurred no earlier than the same week day as Day 1 of P4 the following week, i.e. after an additional 4 days, and no later than a fortnight after Day 2 of P4, i.e. after an additional 14 days.

This has been a single dose study with in total 4 replicate administrations. The effect of the IPs was to last about 24 hours, which is why the subjects have been confined to the institute for 2 days. Subjects have been exposed to treatment 4 times.

The primary objective of the study was to assess the average bioequivalence (ABE) of Lantus® U100 (commercial formulation) and insulin glargine U300 in bioavailability (exposure) and bioefficacy (activity) using the euglycemic clamp technique.

The secondary objective of the study was to assess safety and tolerability of insulin glargine U300.

As mentioned above, both insulin glargine formulations, U100 and U300, were expected to provide the same insulin exposure and the same effectiveness. However, surprisingly insulin exposure and effectiveness were shown to be not the same. Insulin glargine U 100 and insulin glargine U 300 are not equivalent in bio-availability (exposure) and bio-efficacy (activity). Exposure and activity after administration of insulin glargine U300 were less by about 40% as compared to exposure and activity after administration of the same amount (0.4 U/kg) from insulin glargine U100.

Insulin glargine U300 did, however, show an even flatter PK (exposure) and PD (activity) profile than insulin glargine U100, as would be desired for a basal insulin. These surprising and unexpected differences in exposure and activity between insulin glargine U100 and insulin glargine U300 formulations after the same s.c. dose to healthy subjects are effectively shown in the figures below. Of note, at the same time blood glucose was constant.

The blood glucose lowering effect of insulin glargine was additionally evaluated in healthy, normoglycemic Beagle dogs. With increasing insulin glargine concentration the mean time of action increased from 6.8 h (U100) to 7.69 h (U300), respectively.

By increasing the glargine concentration from 100 to 300 U/mL the blood glucose decreasing time-action profile was changed towards a flatter and prolonged activity in the dog. The current data in dogs is consistent with data in humans showing that higher drug concentrations of insulin glargine are positively correlated with profile and longer duration of action.

Additionally, the precipitates of insulin glargine formulations having concentrations of 100 U/mL, 300 U/mL, 500 U/mL 700 U/mL and 1000 U/mL have been investigated by microscopy. These investigations revealed differences in the precipitations characteristics, leading to remarkable bigger particles with increasing concentrations.

Furthermore, the influence of the higher concentrations of insulin glargine formulations with regard to dissolution properties are investigated by using an in-vitro test system. To do so, precipitation studies were performed using a phosphate buffer with a pH of 7.4, simulating the in-vivo conditions.

The supernatant of the precipitated insulin was investigated using HPLC technique to determine the insulin glargine content.

The present invention is not limited to an insulin glargine U 300 formulation and is effective with other higher concentrated formulations of insulin glargine as outlined in detail in the specification, the clinical studies described herein were performed with an insulin glargine U 300 formulation.

Specifically, the insulin glargine formulations of the present invention exhibit a flatter PK (exposure) and flatter PD (activity) profile than insulin glargine U100 and surprisingly act as improved basal insulins compared to U100 glargine insulin and therefore impart extended duration of exposure and reduce the incidence of hypoglycemia in the treatment of Type I and Type II diabetes, for example.

1 mL of insulin glargine U 300 formulation contains 10.913 mg $21^A$-Gly-$30^B$a-L-Arg-$30^B$b-L-Arg human insulin [equimolar to 300 IU human insulin], 90 μg zinc, 2.7 mg m-cresol, 20 mg glycerol 85%, HCl and NaOH ad pH 4.0; specific gravity 1.006 g/mL However, variations with regard to the kind of excipients and their concentrations are possible.

The pharmaceutical formulation of the present invention contains 200-1000 U/mL of insulin glargine [equimolar to 200-1000 IU human insulin], preferably 250-500 U/mL of insulin glargine [equimolar to 250-500 IU human insulin], more preferred 270-330 U/mL of insulin glargine [equimolar to 270-330 IU human insulin], and even more preferred 300 U/mL of insulin glargine [equimolar to 300 IU human insulin].

In one embodiment, the present invention is directed to an aqueous pharmaceutical formulation comprising insulin glargine in the range of 200-1000 U/mL [equimolar to 200-1000 IU human insulin], preferably 200 U/ml to 650 U/mL, still preferably 700 U/mL to 1000 U/ml, more preferably 270-330 U/mL and most preferably in a concentration of 300 U/mL.

In one embodiment, the present invention is directed to an aqueous formulation comprising 200-1000 U/mL [equimolar to 200 to 1000/U human insulin] of insulin glargine, with the proviso that the concentration of insulin in said formulation is not 684 U/ml of insulin glargine.

In another embodiment, the pharmaceutical formulation of the present invention contains 200 U/mL of insulin glargine (equimolar to 200 IU human insulin] or 300 U/mL of insulin glargine [equimolar to 300 IU human insulin] or 400 U/mL of insulin glargine [equimolar to 400 IU human insulin] or 500 U/mL of insulin glargine [equimolar to 500 IU human insulin] or 600 U/mL of insulin glargine [equimolar to 600 IU human insulin] or 700 U/mL of insulin glargine [equimolar to 700 μl human insulin] or 800 U/mL of insulin glargine [equimolar to 800 IU human insulin] or 900 U/mL of insulin glargine [equimolar to 900 IU human insulin] or 1000 U/mL of insulin glargine [equimolar to 1000 IU human insulin].

Surfactants can be added to pharmaceutical formulation, for example, inter alia, non-ionic surfactants. In particular, pharmaceutically customary surfactants are preferred, such as, for example:
partial and fatty acid esters and ethers of polyhydric alcohols such as of glycerol, sorbitol and the like (Span®, Tween®, in particular Tween® 20 and Tween® 80, Myrj®, Brij®), Cremophor® or poloxamers. The surfactants are present in the pharmaceutical composition in a concentration of 5-200 µg/ml, preferably of 5-120 µg/ml and particularly preferably of 20-75 µg/ml.

The formulation of the present invention can additionally contain preservatives (e.g. phenol, m-cresol, p-cresol, parabens), isotonic agents (e.g. mannitol, sorbitol, lactose, dextrose, trehalose, sodium chloride, glycerol), buffer substances, salts, acids and alkalis and also further excipients. These substances can in each case be present individually or alternatively as mixtures.

Glycerol, dextrose, lactose, sorbitol and mannitol can be present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, preferably 10-100 mM. Further excipients can be, inter alia, salts or arginine.

The zinc concentration of the formulation of the present invention is in the range of the concentration which is reached by the presence of 0-1000 µg/mL, preferably 20-400 µg/mL zinc, most preferably 90 µg/mL. However, the zinc may be present in form of zinc chloride, but the salt is not limited to be zinc chloride.

In the pharmaceutical formulation glycerol and/or mannitol can be present in a concentration of 100-250 mmol/L, and/or NaCl is preferably present in a concentration of up to 150 mmol/L.

In the pharmaceutical formulation a buffer substance can be present in a concentration of 5-250 mmol/L.

A further subject of the invention is a pharmaceutical insulin formulation which contains further additives such as, for example, salts which delay the release of insulin. Mixtures of such delayed-release insulins with formulations described above are included therein.

For producing the formulations of the present invention the ingredients are dissolved in water and the pH is adjusted by using HCl and/or NaOH; and likewise by methods known in the art. Likewise, a further subject of the invention is directed to the use of such formulations for the treatment of diabetes mellitus.

A further subject of the invention is directed to the use or the addition of surfactants as stabilizers during the process for the production of insulin, insulin analogs or insulin derivatives or their preparations.

The invention further relates to a formulation as described above which additionally comprises also a glucagon-like peptide-1 (GLP1) or an analogue or derivative thereof, or exendin-3 or -4 or an analogue or derivative thereof, preferably exendin-4.

The invention further relates to a formulation as described above in which an analogue of exendin-4 is selected from a group comprising
H-desPro$^{36}$-exendin-4-Lys$_6$-NH$_2$,
H-des(Pro$^{36,37}$)-exendin-4-Lys$_4$-NH$_2$ and
H-des(Pro$^{36,37}$)-exendin-4-Lys$_5$-NH$_2$,
or a pharmacologically tolerable salt thereof.

The invention further relates to a formulation as described above in which an analogue of exendin-4 is selected from a group comprising
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{28}$]exendin-4 (1-39),
desPro$^{36}$ [Trp(O$_2$)$^{25}$, Asp$^{28}$]exendin-2 (1-39),
desPro$^{36}$ [Trp(O$_2$)$^{25}$, IsoAsp$^{28}$]exendin-2 (1-39),
desPro$^{36}$ [Met(O)$^{14}$Trp(O$_2$)$^{25}$, Asp$^{28}$]exendin-4 (1-39) and
desPro$^{36}$ [Met(O)$^{14}$Trp(O$_2$)$^{25}$, IsoAsp$^{28}$]exendin-4 (1-39),
or a pharmacologically tolerable salt thereof.

The invention further relates to a formulation as described in the preceding paragraph, in which the peptide -Lys$_6$-NH$_2$ is attached to the C termini of the analogues of exendin-4.

The invention further relates to a formulation as described above in which an analogue of exendin-4 is selected from a group comprising
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)-NH$_2$,
H-(Lys)$_6$-des Pro$^{36}$, Pro$^{37}$, Pro$^{38}$ [Asp$^{28}$]exendin-4(1-39)-NH$_2$,
H-Asn-(Glu)$_5$ des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$]exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4(1-39)-Lys$_6$-NH$_2$,
des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$'Pro$^{37}$, Pro$^{38}$ [Met(O)$^{14}$, Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$, des Pro$^{36}$, Pro$^{37}$, Pro$^{38}$ [Met(O)$^{14}$, Trp(O$_2$)$_{25}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$,
or a pharmacologically tolerable salt thereof.

The invention further relates to a formulation as described above which additionally comprises Arg$^{34}$, Lys$^{26}$ (N$^\epsilon$(γ-glutamyl(N$^\alpha$-hexadecanoyl))) GLP-1 (7-37) [liraglutide] or a pharmacologically tolerable salt thereof.

Additionally, the formulation of the present invention can also comprise an analogue of exendin-4, such, for example, lixisentatide, exenatide and liraglutide. These exendin-4 analogues are present in the formulation in the range of 0.1 µg to 10 µg per U insulin glargine, preferably 0.2 to 1 µg per U insulin glargine, and more preferably 0.25 µg to 0.7 µg per U insulin glargine. Lixisenatide is preferred.

Additionally, the aqueous pharmaceutical formulation can comprise one or more excipients selected from a group comprising zinc, m-cresol, glycerol, polysorbate 20 and sodium. Specifically, the aqueous pharmaceutical formulation can comprise 90 µg/mL zinc, 2.7 mg/mL m-cresol and 20 mg/ml glycerol 85%. Optionally, the aqueous pharmaceutical formulation can comprise 20 µg/mL polysorbate 20.

The pH of the aqueous pharmaceutical formulation is between 3.4 and 4.6, preferably 4 or 4.5.

The present invention is directed to a method of treating Type I and Type II Diabetes Mellitus comprising administering to said patient the aqueous pharmaceutical composition of the present invention to a diabetic patient. Preferred among the various disclosed concentration ranges is a concentration of 300 U/mL and the preferred insulin analogue is insulin glargine. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine.

The insulin is administered preferably once daily but can be administered twice daily as needed. Dosage requirements are a function of the needs of the individual patient determined by the achievement of normal or acceptable blood glucose levels.

The present invention is also directed to a method of extending the duration of exposure of insulin glargine in the treatment of Type I and Type II Diabetes Mellitus in a patient comprising administering to said patient the aqueous pharmaceutical formulation of the present invention. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention.

In a preferred embodiment the aqueous pharmaceutical formulation also comprises 0.1 µg to 10 µg lixisenatide per U insulin glargine.

The present invention is also directed to a method of reducing the incidence of hypoglycaemia in the treatment of Type I and Type II Diabetes Mellitus in a patient with insulin glargine comprising administering to said patient the aqueous pharmaceutical formulation of the present invention. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine.

The present invention is also directed to a method of providing a peakless long acting basal insulin in the treatment of Type I and Type II Diabetes Mellitus in a patient with comprising administering to said patient the aqueous pharmaceutical formulation of the present invention. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine.

Use of an aqueous formulation according to any of the foregoing items in the treatment of Type 1 Diabetes Mellitus and Type 2 Diabetes Mellitus.

The application is described below with the aid of some examples, which are in no way intended to act restrictively.

EXAMPLE 1

Description of the Protocol

This study was a single center, randomized, controlled, single-blind, four-period, 2-treatment, 2-sequence crossover study in healthy subjects with six visits:
Visit 1: Screening (SCR)
Visit 2 to 5, Period (P) 1-4: Treatment, euglycemic clamp period
Visit 6: End-of-study (EOS)

Subjects received single subcutaneous doses of 0.4 U/kg insulin glargine U100 and insulin glargine U300 alternatingly injected into two opposite sites of the periumbilical area (left, right, left, right) at four different days. The study medication was administered with a replicate of treatment R and T in 2 sequences, RTTR or TRRT at P1 to P4. A washout period of 4 to 18 days was separated each dosing day.
R: 0.4 U/kg body weight insulin glargine U100 (commercial formulation; Reference)
T: 0.4 U/kg body weight insulin glargine U300 (Test)
P1 must take place no more than 3 to 21 days after SCR. EOS visit must take place between 4 to 14 days after P4.

During P1 to P4, subjects have been connected to a Biostator for measurement of blood glucose and adjustment of glucose infusion rate. Blood glucose levels and glucose infusion rate (GIR) have been monitored for 90 minutes (baseline period) before subcutaneous injection of the study medication and for 30 hours after study medication administration. Infusion of 20% glucose solution commenced to maintain blood glucose levels at 5% below the individual fasting blood glucose level, determined as the mean of the 3 fasting blood glucose values measured 60, 30 and 5 minutes before study medication administration. Profiles of GIR have been obtained. Blood samples have been taken at predetermined times during the euglycemic clamp period for determination of serum insulin glargine concentrations. With the exception of tap water, subjects have been fasting during the glucose clamp period.

The duration of this study for an individual was expected to be up to 13 weeks between SCR and EOS visit.

The protocol was submitted to independent ethics committees and/or institutional review boards for review and written approval. The protocol complied with recommendations of the 18th World Health Congress (Helsinki, 1964) and all applicable amendments. The protocol also complied with the laws and regulations, as well as any applicable guidelines, of Germany, where the study was conducted. Informed consent was obtained prior to the conduct of any study-related procedures.

EXAMPLE 2

Selection of subjects

Twenty four (24) healthy subjects were planned to be treated in order to have 20 completers.

Subjects meeting all of the following criteria have been considered for enrollment into the study:

Demography
  Subjects of either gender between 18 and 50 years of age;
  Body weight between 50 kg and 110 kg and Body Mass Index between 18 and 28 kg/m$^2$;
Health Status
  Certified as healthy following a comprehensive clinical assessment (detailed medical history and complete physical examination);
  Non-smoker for at least 3 months;
  12-lead electrocardiogram, and vital signs unless the Investigator considers an abnormality to be clinically irrelevant
    Normal vital signs after 5 minutes resting in supine position:
    95 mmHg≤systolic blood pressure≤140 mmHg;
    45 mmHg≤diastolic blood pressure≤90 mmHg;
    40 bpm≤heart rate≤100 bpm;
    Normal 12-lead ECG; 120 ms<PR<220 ms, QRS<120 ms, QTc≤430 ms (for female: QTc≤450 ms);
  Laboratory parameters within the normal range unless the Investigator considers an abnormality to be clinically irrelevant for healthy subjects; however serum creatinine and hepatic enzymes (AST, ALT) should be strictly below the upper laboratory norm;
  Normal metabolic control defined as fasting serum glucose (≤100 mg/dL) and glycosylated hemoglobin (HbA1c≤6.1%);
  Subjects must be off regular use of prescription drug therapy, for at least four (4) weeks prior to participation in the study;
Obligations for Female Subjects
  Female subjects of childbearing potential (defined as pre-menopausal and not surgically sterilized or post-menopausal for less than 2 years) and sexually active must practice adequate birth control. Adequate birth control is defined as a highly effective method of contraception (Pearl index<1%) such as implants, injectables, combined oral contraceptives or hormonal IUDs (intrauterine devices). Post-menopausal for the purposes of this clinical trial include: amenorrhea for 2 or more years or surgically sterile;
  Female subjects must have a negative urine beta-human chorionic gonadotropin (beta-HCG) pregnancy test during the pre-study screening, and prior to the first clamp;
Regulations
  Having given written informed consent prior to any procedure related to the study;
  Covered by Health Insurance System and/or in compliance with the recommendations of National Law in force relating to biomedical research;
  Not under any administrative or legal supervision.

Subjects presenting with any of the following have not been included in the study:

Medical History and Clinical Status
  Any history or presence of clinically relevant cardiovascular, pulmonary, gastro-intestinal, hepatic, renal, metabolic, hematological, neurologic, psychiatric, systemic, ocular or infectious disease; any acute infectious disease or signs of acute illness;
  Presence or history of drug allergy, or allergic disease diagnosed and treated by a physician;
  Excessive consumption of beverages with xanthine bases (>4 cups or glasses/day);
  Contraindications from (according to normal ranges—if the value is outside of the normal range the subject can be included if the Investigator sees this abnormal value as clinically irrelevant):
    the medical/surgical history and physical examination
    laboratory tests (hematology, clinical chemistry, and urinalysis by dipstick)
    standard 12-lead electrocardiogram
    blood pressure and heart rate
  Any ongoing treatment with prescribed drugs or any regular treatment with prescribed drugs in the 4 weeks prior to participation in the study
  Symptoms of a clinically significant illness in the 3 months before the study, or of any major internal medical disease in the 4 weeks before the study which, according to the Investigator's opinion, could interfere with the purposes of the study.
  Presence or sequelae of a disease or other conditions known to interfere with the absorption, distribution, metabolism, or excretion of drugs
  History of drug or alcohol abuse
  History of hypersensitivity to the study medication or to drugs with similar chemical structures
  Progressive fatal disease
  Pre-planned surgery during the study
  Blood donation of more than 500 mL during the previous 3 months No subject has been allowed to enroll in this study more than once.

General Conditions
  Subject who, in the judgment of the Investigator, is likely to be non-compliant during the study, or unable to cooperate because of a language problem or poor mental development or due to a mental condition rendering the subject unable to understand the nature, scope and possible consequences of the study
  Subject in exclusion period of a previous study according to applicable regulations;
  Subject is the Investigator or any Sub-Investigator, Research Assistant, Pharmacist, Study Coordinator, other Staff thereof, directly involved in the conduct of the protocol;
  Receipt of an experimental drug within the previous 30 days before SCR.
Biological Status
  Positive reaction to any of the following tests: HBs antigen, anti-HCV antibodies, anti-HIV 1 antibodies, anti-HIV2 antibodies;
  Positive results on urine drug screen at SCR (amphetamines/metamphetamines, barbiturates, benzodiazepines, cannabinoids, cocaine, opiates);
  Positive alcohol breath test

EXAMPLE 3

Treatments

Details of Study Treatments

| Drug code: HOE901 (Lantus ® U100 commercial formulation) INN: Insulin glargine (recombinant human insulin analogue) Formulation: Cartridges for 3 mL solution U100 (1 mL contains 3.637 mg $21^A$-Gly-$30^B$a-L-Arg-$30^B$b-L-Arg human insulin [equimolar to 100 IU human insulin], 30 µg zinc, 2.7 mg m-cresol, 20 mg glycerol 85%, HCl and NaOH ad pH 4.0; specific gravity 1.004 g/mL) Dose/route of administration 0.4 U/kg body weight; single s.c. injection into the periumbilical abdomen after an overnight fast Manufacturer: Sanofi-Aventis Deutschland GmbH | (Insulin glargine U300 formulation) Insulin glargine (recombinant human insulin analogue) Cartridges for 3 mL solution U300 (1 mL contains 10.913 mg $21^A$-Gly-$30^B$a-L-Arg-$30^B$b-L-Arg human insulin [equimolar to 300 IU human insulin], 90 µg zinc, 2.7 mg m-cresol, 20 mg glycerol 85%, HCl and NaOH ad pH 4.0; specific gravity 1.006 g/mL) 0.4 U/kg body weight; single s.c. injection into the periumbilical abdomen after an overnight fast Manufacturer: Sanofi-Aventis Deutschland GmbH |
|---|---|

Calculation of the Dose for Lantus®/Insulin Glargine Formulation

To calculate the amount of insulin glargine given for each subject (0.4 U/kg), the body weight (in kg) has been determined to one decimal place and the amount of insulin calculated has been rounded up or down to integer numbers as shown in the following examples: a subject with a body weight of 75.3 kg has received 30 U insulin (75.3×0.4=30.12 which is rounded down to 30); a subject with a body weight of 74.4 kg has received 30 U insulin (74.4×0.4=29.76, which is rounded up to 30). The body weight recorded during Period 1 Day 1 has been used for calculation of study medication dose for Periods 2, 3 and 4, unless the body weight changed by more than 2 kg compared to Period 1.

The amount in Units has been the same for both insulin glargine U100 and insulin glargine U300. This specific gravity is the same for both drug products. However, given the three times higher concentration of insulin glargine in insulin glargine U300 as compared to insulin glargine U100, the to be injected volume and hence the weight has been ⅓ for insulin glargine U300. The syringes providing the individual dose have been prepared by weight. The net weight has been documented only in the source-documentation of the Investigator.

Calculation and Preparation of the Dose for Infusions

TABLE 1

Preparation of infusion

| Drug Code | INN | Formulation | Manufacturer | Dose/Route of administration |
|---|---|---|---|---|
| Glucose | Glucose | 20% solution for infusion | Certified, selected by PROFIL | iv infusion |
| Intramed Heparin Sodium | Heparin | Vial containing 5 mL solution (5000 IU/mL) | Certified, selected by PROFIL | iv infusion |
| 0.9% Sodium Chloride | Sodium Chloride | Solution | Certified, selected by PROFIL | iv infusion |

Glucose solution: 20% glucose solution has been infused with the Biostator to keep subjects individual blood glucose at the determined target level. A second infusion pump (part of the Biostator) has delivered 0.9% sodium chloride solution to keep the line patent. In case the amount of 20% glucose solution needed exceeds the infusion capacity of the Biostator, a second glucose infusion pump has been engaged.

Heparin: 10000 IU heparin in 100 mL 0.9% sodium chloride solution have been infused into the double lumen catheter at a rate of approximately 2 mL/h to keep it patent for blood glucose measurement by the Biostator.

Description of Blinding Methods:

This was a single-blind study. The different volumes of injection preclude blinding of the medication. Injection has been done by an authorized medical person otherwise not involved in the study. The Investigator has access to the randomization code.

Method of Assigning Subjects to Treatment Group

The study medication has been administered only to subjects included in this study following the procedures set out in the clinical study protocol.

A randomization schedule has been generated, which has linked the randomization numbers, stratified by gender, to the treatment sequences of the two Lantus® formulations to be injected at P1 to P4.

In the morning of Day 1 of Period 1, as soon as the Investigator has confirmed that subjects fulfill the criteria specified in the protocol, the eligible subjects were randomized by the site. The randomization number was allocated to the subject number subsequently in the order in which subjects' eligibility has been confirmed before P1. The first subject for a gender stratum qualifying after SCR received the first randomization number for the appropriate gender stratum. The next subject who qualifies within a stratum received the next randomization number within the stratum.

The randomization number has been used as the treatment kit number to allocate the treatment kit to the subject. Each subject were given the study medication carrying the treatment kit number to which he has been allocated to. The treatment kit containing the IP carried general information, treatment kit number, period number, a field to write the subject number on the container-box, and additional statements as required by local regulations.

Subjects who permanently discontinue from the study retained subject number and randomization number, if already given.

Packaging and Labelling

The study medication has been packed by Sanofi-Aventis Deutschland GmbH, Frankfurt am Main, Germany according to the randomization plan. The cartridges containing the study medication and the cartons they were packed in have been labeled with the study number, the randomization number, batch number, storage conditions, Sponsor and the P number.

Supplies of study medication have been received in one shipment. All containers had labels of identical format. Additionally, 1 set of labels for syringes has been supplied. Study medication and back-up medication were stored in different refrigerators.

Before study medication administration, the Pharmacist or the person designated by him has prepared the syringes with the appropriate study medication and has labeled the syringe with the subject number, the randomization number and the appropriate period according to the study medication containers.

The content of the labeling was in accordance with the local regulatory specifications and requirements.

Storage Conditions

The study medication was stored protected from light at a temperature of +2° C. to +8° C. The study medication was prevented from freezing. During preparation it was not necessary to have the medication protected from light.

Reserve samples (300 cartridges Lantus® U100 and 300 cartridges insulin glargine U 300) were stored in the same secure conditions at the study site level.

EXAMPLE 4

Assessment of Investigational Product

Activity or Pharmacodynamics

Stimulation of insulin receptors by insulin glargine is the mode of action. Subsequent peripheral glucose uptake and suppression of endogenous glucose production comprise the glucodynamic effects producing a reduction in blood glucose concentration. The resulting glucose utilization is best characterized by the gauge of glucose required to keep the blood glucose concentration constant.

The euglycemic clamp technique has been employed to assess the amount of glucose needed to keep blood glucose concentrations at 5% below baseline level after injection of insulin glargine.

Clinical Assessment Methods

Online blood glucose determination has been done by the Biostator (Life Sciences instruments, Elkhart, 1N, USA) employing the glucose oxidase method.

Offsite blood glucose has been determined with a Super GL glucose analyzer also using the glucose oxidase method.

Pharmacodynamic Variables/Endpoints

The amount of glucose utilized per unit (dose) of subcutaneously injected insulin is a measure of the glucodynamic effect.

The continuously recorded glucose infusion rate (GIR) is a reflection of the time action profile of the injected insulin Primary Variable/Endpoint The primary pharmacodynamic variable is the area under the glucose infusion rate time curve within 24 hours [GIR-$AUC_{0-24h}$ ($mg \cdot kg^{-1}$)].

Secondary Variable/Endpoint

The secondary pharmacodynamic variable is the time to 50% GIR-$AUC_{0-24h}$ [$T_{50}\%$–GIR-$AUC_{(0-24h)}$ (h)].

Pharmacokinetics

Sampling Times

Blood samples for assessment of serum insulin glargine and C-peptide concentrations have been taken 1 hour, 30 min and immediately prior to subcutaneous injection of study medication, thereafter 30 min, 1 hour, 2 hours and then bi-hourly up to 24 hours, and 30 hours after injection.

The numbering of insulin glargine samples was P00, P01, P02, P03, P04, etc., the numbering of C-peptide samples was C00, C01, C02, C03, C04, etc (see also study flow chart).

Number of Pharmacokinetic Sampling

A minimum of 18 samples have been taken per clamp visit (P1 to P4). In total 72 samples have been taken per subject.

PK Handling Procedure

The exact time of sample collection must be recorded on the CRF. Special procedures for storage and shipping of pharmacokinetic samples (insulin glargine, C-peptide) have been used.

Bioanalytical Method

Bioanalysis have been performed using as a basis the Good Laboratory Practice (GLP) requirements applicable to this type of study identified in the OECD Principles of Good Laboratory Practice (as revised in 1997), ENV/MC/CHEM (98)17 and the GLP regulations applicable to the local country.

As no back-up samples are available priority is given to determination of insulin glargine.

Insulin Glargine

Serum insulin glargine concentrations have been determined using a radioimmunoassay (RIA) for human insulin (Insulin RIA kit, ADALTIS, Italy) calibrated for insulin glargine. Kit REF 10624.

The lower limit of quantification (LLOQ) for this assay was 4.92 µU/mL.

C-Peptide

Serum C-peptide concentrations have been determined using a radioimmunoassay (RIA) for C-peptide (C-peptide RIA kit, ADALTIS, Italy). Kit REF C-peptide 10282.

The lower limit of quantification (LLOQ) was 0.090 nmol/L.

Summary of Bioanalytical Method

| | |
|---|---|
| Analyte | insulin, C-peptide |
| Matrix | serum |
| Analytical Technique | RIA |
| Lower limit of quantification | 4.92 µU/mL insulin; 0.090 nmol/L C-peptide |
| Assay volume | 100 µL for insulin; 100 µL for C-peptide |
| Method Reference | Adaltis S.p.A. Italy; Kit REF 10624 Insulin (Method No. 435VAL02) and Kit REF C-peptide 10282 (Method No. DMPK/FRA/2003-0002) |

Pharmacokinetic Variables/Endpoints

The insulin glargine concentration time curve was a measure of the systemic insulin exposure of subcutaneously injected IP.

Primary Variable/Endpoint

The primary pharmacokinetic variable was the area under the serum insulin glargine concentration time curve [INS-$AUC_{0-24h}$ ($\mu U \cdot h \cdot mL^{-1}$)].

Secondary Variable/Endpoint

The secondary pharmacokinetic variable was the time to 50% INS-$AUC_{0-24h}$ [$T_{50}\%$–INS-$AUC_{(0-24h)}$ (h)].

Sampled Blood Volume

| Sampled blood volume | |
| --- | --- |
| Archival Blood/Genotyping | 0 mL |
| Hematology/Clinical chemistry/Serology (20 + 12 mL) | 32 mL |
| RBC, Hb, Hct (2 × 2 mL) optional | 4 mL |
| Blood glucose (2 mL/h × 32 × 4) | 256 mL |
| Blood glucose (0.3 mL × 4 × 34) | 41 mL |
| PK insulin glargine (3.5 mL × 18 × 4) | 252 mL |
| Total | 585 mL |

Measures to Protect Blinding of the Trial

This has been a single-blind study. Bioanalytical determinations have been performed after clinical completion. The treatment code has been known for reporting of any Serious Adverse Event (SAE) unexpected and reasonably associated with the use of the IP according to either the judgment of the Investigator and/or the Sponsor.

EXAMPLE 5

Study Procedures

Visit Schedule
Screening Procedures

The medical records of each potential subject has been checked before the start of the study to determine eligibility for participation. The subjects have fasted (except for water) for 10 hours before the screening examination at SCR.

The following items/examinations have been assessed:
Age, and race
Physical examination (including cardiovascular system, chest and lungs, thyroid, abdomen, nervous system, skin and mucosae, and musculoskeletal system)
Relevant medical and surgical history (only findings relevant to the study are to be documented)
Anthropometrics: height and weight, calculation of BMI [weight in kg·(height in m)$^{-2}$]
Blood pressure and heart rate (after 5 min in supine and 3 min upright position)
Core body temperature (tympanic)
Standard 12-lead ECG
Hematology status, clinical chemistry, and urinalysis (by dipstick)
Coagulation status (INR, aPPT)
Urine drug screen
Alcohol screen (breath analyzer)
Normal metabolic control defined as fasting blood glucose ($\leq 100$ mg·dL$^{-1}$) and glycosylated hemoglobin (HbA1c$\leq 6.1\%$)
Hepatitis B/C and HIV test In case the subject is a screening failure, all data obtained at SCR including laboratory results of screening tests were available in the subject's medical record.

Description by Type of Visit
Period(s)

Each study period (P1 to P4) lasted 2 days, Day 1 and Day 2. Day 1 was the starting day of the euglycemic clamp and administration of study medication. Day 2 was day of the end of the euglycemic clamp, which lasted 30 hours after study medication administration. There was a wash-out period of 4-18 days between the study periods (P1-P4). No strenuous activity (e.g. mountain biking, heavy gardening etc.) has been allowed 2 days before each study medication administration. Consumption of alcoholic beverages, grapefruit juice, and stimulating beverages containing xanthine derivatives (tea, chocolate, coffee, Coke™-like drinks, etc.) and grapefruit has not been permitted from 24 hours before until completion of the euglycemic clamp. The subjects have fasted (except for water) for 10 hours before Day 1 of each study period (P1 to P4) and remained fasting (except for water) until end of the euglycemic clamp. The subjects had to stay in the clinic for approximately 32 hours at each clamp visit.

In the morning of Day 1 of Period 1, the 9-digit subject number has been allocated to the subject, starting with 276001001. The next subject who qualifies to enter SCR has received the subject number 276001002 etc. The first subject has received the randomization number 101. The next subject who qualifies has received the randomization number 102.

Subjects have been asked to ensure that they have had no clinically significant changes in their physical condition and have been compliant with the general and dietary restrictions as defined in the protocol since the previous periods. Violation of the study criteria has excluded subjects from participation in the study. Depending on the kind of violation the subject might have been excluded only from the particular period, allowing a re-scheduling of the study day. Any protocol violations have been discussed with the Sponsor on a case-by-case basis in advance.

Any changes in the health condition of the subjects since the last period have been reported in the subject's medical records (source) and the CRF.

The blood pressure, heart rate and core body temperature (tympanic) have been recorded in supine position after at least 5 minutes rest in the morning of Day 1, prior to and after completion of clamp procedures 30 hours after each study medication administration (Day 2). Body weight, alcohol screen and RBC, Hb, HcT (only before clamp period of P3 and P4) have been assessed only before starting the clamp in the morning of Day 1.

On Day 1 of each period, subjects have been admitted to the clinic at 6:30 am. After passing the above described examinations, subjects have been prepared with three venous lines. A dorsal hand vein or lateral wrist vein of the left arm has been cannulized in retrograde fashion and connected to a Biostator (Life Sciences instruments, Elkhart, Ind., USA) in order to continuously draw arterialized venous blood for the determination of blood glucose. To achieve arterialization the left hand has been placed in a "Hot-Box" at about 55° C. A second venous line has been placed into the antecubital vein of the left arm and have been used to collect samples for serum insulin glargine and reference blood glucose determination. A third vein has been cannulised on the contralateral forearm allowing the infusion of 20% glucose solution and 0.9% saline with the Biostator.

The Biostator determined blood glucose levels and adjusted the glucose infusion rate to maintain blood glucose levels at 5% below the individual fasting blood glucose, determined as the mean of the 3 fasting blood glucose values measured 60, 30 and 5 minutes before study medication administration. Additional blood samples of 0.3 mL for the determination of blood glucose have been taken 60, 30, and 5 minutes before administration of the study medication to check against a laboratory reference based on the glucose oxidase method.

Approximately at 09:00 am, either insulin glargine U100 (commercial formulation) or insulin glargine U300 have been injected in the periumbilical area 5 cm lateral to the umbilicus (left, right, left, right) using a standardized skin fold technique. U100 insulin syringes (manufacturer: Beckton & Dickinson) of 0.5 mL volume with a needle of 0.30 mm×8 mm (30G) have been used.

The study medication was labeled with their respective treatment kit number, subject number (to be documented on the container-box after randomization), and Period number (see Section 8.5 Packaging and Labeling).

After study medication administration, infusion of 20% glucose solution have commenced at a variable rate once blood glucose level has fallen by 5% from the individual fasting level to maintain that level. The duration of the clamp period have been 30 hours. The rate of glucose delivery have been adjusted by the Biostator in response to changes in blood glucose at 1 minute intervals using a predefined algorithm. The blood glucose values from the Biostator have been checked against a laboratory reference based on the glucose oxidase method at 30 minutes intervals for the entire clamp. If necessary the Biostator have been re-calibrated according to results of the laboratory reference method. Subjects remained in supine position during the period of clamping.

Blood samples for determination of serum insulin glargine and C-peptide concentrations have been taken 1 hour, 30 min and immediately before medication and thereafter 30 min, 1 hour, 2 hours and then bi-hourly up to 24 hours, and 30 hours after administration of study medication.

On day 2 of each study period (P1 to P4), a meal have been served after the euglycemic clamp has been completed. Blood pressure, heart rate, and core body temperature (tympanic) have been recorded, and a sample for blood glucose has been taken. The subjects have been discharged from the clinic after their safety has been ensured by the Investigator.

Injection sites have been observed during the entire clamp period. Any changes in the health condition of the subjects have been reported in the subject's medical records (source) and the CRF.

Safety Hematology

RBC, Hb and Hct at P 3 have been analyzed for incurring anemia at P 4. If positive, the interval between P 3 and P 4 have been extended to the maximum allowed 18 days and an additional RBC, Hb and Hct assessment made prior to P 4.

Discharge Procedures

Subjects have returned for an EOS visit between 4 to 14 days after P4. Subjects have fasted (apart from water) for 10 hours. Any changes in the health condition of the subjects since the last period have been reported in the subject's medical records (source) and the CRF.

The following items/examinations have been assessed:
Physical examination (including cardiovascular system, chest and lungs, thyroid, abdomen, nervous system, skin and mucosae, and musculoskeletal system)
Weight
Blood pressure and heart rate (after 5 min in supine position)
Core body temperature (tympanic)
Standard 12-lead ECG
Hematology status, clinical chemistry, and urinalysis (by dipstick)
β-HCG test in urine (only for females)

The subjects have been discharged on Day 2 of each period, after a complete review by the Investigator of the available safety data.

Collection Schedule for Biological Samples
Blood
SCR (Screening):
Hematology, Clinical Chemistry, HbA1c, Serology (Hepatitis B/C test, HIV test): approximately 20 mL of blood have been collected.

P1 to P4 (Day 1 and 2):
Blood glucose
Biostator has automatically measured blood glucose at one minute intervals for the entire clamp period, including the period prior to study medication. The volume of blood needed by the Biostator have been 2 mL·h$^{-1}$. An estimated 252 mL blood volume have been needed for glucose readings with the Biostator for the four periods. Blood samples (0.3 mL) for checking blood glucose values from Biostator have been collected 60, 30, 5 and 0 minutes prior to dosing and at 30 minute intervals after dosing until end of the clamp (30 hours). An estimated 41 mL blood volume have been collected for the four periods.

Serum insulin glargine and C-peptide concentrations
Venous blood samples (3.5 mL) have been collected 1 hour, 30 min and immediately prior to dosing, 30 min, 1 hour, 2 hours and then bi-hourly up to 24 hours, and 30 hours after dosing. An estimated 252 mL blood volume have been collected for the four periods. Determination of insulin glargine has been given priority. Spare samples only have been used for determination of C-peptide concentration.

RBC, Hb, Hct
Venous blood have been collected before commencing clamp period 3 and 4. Approximately 4 mL of blood have been collected for the two periods.

End-of-Study (EOS) Visit:
Hematology, Clinical Chemistry: approximately 12 mL of blood have been collected.
β-HCG test in urine (only for females)

Total Blood Volume SCR-EOS:
In total, approximately 585 mL blood have been collected for each subject during the entire study.

Urine
Qualitative urine drug screen have been conducted at SCR and EOS. Urine drug screen consists of amphetamines/metamphetamines, barbiturates, benzodiazepines, cannabinoids, cocaine, opiates. Qualitative safety urinalysis with dipsticks have been conducted at SCR and EOS. Safety urinalysis consists of analysis for: pH, protein, glucose, blood, erythrocytes, leukocytes, bilirubin, urobilinogen, ketone, specific gravity, and nitrite.

Measurement Schedule for Other Study Variables
Physical examination have been performed at SCR and EOS.
Core body temperature (tympanic) have been taken at SCR, P1 to P4 before and after the clamp period, and at EOS.
Blood pressure and heart rate have been measured after about 5 minutes rest in a supine position, and also after 3 minutes in an upright position at SCR and EOS. In P1 to P4 blood pressure and heart rate have been recorded in supine position after at least 5 minutes prior to start of clamp procedures in the morning of day 1, and after completion of clamp procedures 30 hours after each study medication administration (day 2).
Electrocardiograms (standard 12-lead) have been recorded at SCR and EOS.
Body weight and height have been measured at SCR. The body weight have been recorded in the morning of Day 1 of P1 to P4 (prior to administration of study medication) and at EOS. Alcohol screen (ethanol, breath analyzer) have been conducted at SCR and EOS, and in the morning of Day 1 of P1 to P4 (prior to administration of study medication).

Study Restriction(s)
From Day −1 evening (P1 to P4) and throughout the Periods (clamp days), the subjects have refrained from drinking alcohol, tea, coffee, citrus or cola beverages, smoking. Eating citrus fruits was also prohibited throughout the study. The subjects have been requested to follow a stable lifestyle throughout the duration of the trial, until the last control, with no intensive physical activity.

DEFINITION OF SOURCE DATA

All evaluations listed below that are reported in the CRF were supported by appropriately signed identified source documentation related to:
- subject identification, medical history;
- clinical examination, vital signs, body weight and height;
- laboratory assessments, ECG;
- pharmacokinetic time points;
- dates and times of visits and assessments;
- administration dates and times, and site of injection;
- AEs;
- duration of clamp (start and end times)
- Other The CRF have been considered as source documentation for other items.

EXAMPLE 6

Statistical Considerations

This example provides information for the statistical analysis plan for the study. A statistical analysis plan have been drafted prior to inclusion of subjects.

Determination of Sample Size

INS-AUC$_{(0-24h)}$ have been the primary parameter for which therefore the sample size calculation was performed.

For the purpose of this sample size calculation, several within-subject SD$_{within}$ of natural log-transformed INS-AUC$_{(0-24h)}$ between 0.125 and 0.225 were considered. A sample size calculation method for an average bioequivalence approach was used for a 4-period, 2-treatment, 2-sequence cross-over design. If the 90% CIs for the formulation ratio have been wholly contained within [0.80-1.25], then average bioequivalence have been concluded for the parameter.

Study HOE901/1022 was the basis for assumptions on variability. Based on the statistical analysis of study HOE901/1022, a value of 0.175 could be expected for the within subject standard deviation (SD$_{within}$) on the natural log-transformed scale.

The table below indicates the number of subjects required to demonstrate average bioequivalence of the ratio of adjusted geometric means (test versus reference formulation) using the bioequivalence reference interval: [0.80-1.25], assuming a true ratio between 0.85 and 1.15 with 90% power.

TABLE 2

Required total number of subjects to achieve a power of at least 90%

| Assumed true ratio | SD (within) on natural log-scale | | | | |
|---|---|---|---|---|---|
| | 0.125 N | 0.15 N | 0.175 N | 0.2 N | 0.225 N |
| 0.85 | 38 | 54 | 72 | 94 | 120 |
| 0.90 | 12 | 16 | 20 | 26 | 32 |
| 0.95 | 6 | 8 | 10 | 14 | 16 |
| 1.00 | 6 | 6 | 8 | 10 | 12 |
| 1.05 | 6 | 8 | 10 | 12 | 16 |
| 1.10 | 10 | 14 | 18 | 22 | 28 |
| 1.15 | 20 | 30 | 40 | 50 | 64 |

N = total number of subjects

With this design, 20 subjects (10 per sequence) are required to demonstrate equivalence of the two insulin glargine formulations, with 90% power, allowing true ratio of 0.9, if the true SD$_{within}$ on natural log scale is 0.175.

A number of 24 randomized subjects accounts for potential cases of withdrawals.

Subject Description

Disposition of Subjects

A detailed summary of subject accountability including count of subjects included, randomized, exposed (i.e. received any amount of study medication), completed (i.e. subjects who completed all study treatment periods), discontinued along with the main reasons for discontinuation have been generated for each sequence and for all subjects in total.

Subject disposition at the final visit have been presented in a listing including sequence group, disposition status at the end of the study with the date of last administration of study drug, date of final visit, reason for discontinuation. All withdrawals from the study, taking place on or after the start of the first study drug administration, have been fully documented in the body of the clinical study report (CSR).

Protocol Deviations

Prior to data base lock, the compliance with the protocol have been examined with regard to inclusion and exclusion criteria, treatment compliance, prohibited therapies, and timing and availability of planned assessments. Protocol deviations have been identified by the study team before database lock and listed in the Data Review Report, including missing data and IP discontinuations, and classified as minor or major deviations.

Individual deviations to inclusion and exclusion criteria as reported by the Investigator have been listed.

Other deviations have been listed by and/or described in the body of the CSR.

Analysis Population

Population to be Analyzed

Subjects excluded from any analysis population have been listed with treatment sequence, and with reason for exclusion. Any relevant information have been fully documented in the CSR.

In the event of subjects having received treatments that differed from those assigned according to the randomization schedule, analyses have been conducted according to the treatment received rather than according to the randomized treatment.

Pharmacokinetic Population

All subjects without any major deviations related to study drug administration, and for whom PK parameters are available, have been included in the pharmacokinetic population. For subjects with insufficient PK profiles in some but not all study days, parameters of the sufficient profiles have been included in the analysis.

Pharmacodynamic Population

All subjects without any major deviations related to study drug administration, and for whom PD parameters are available, have been included in the pharmacodynamic population. For subjects with insufficient GIR-profiles in some but not all study days, parameters of the sufficient profiles have been included in the analysis.

Safety Population

Safety evaluation have been based on subjects who received a dose of study drug (exposed population), regardless of the amount of treatment administered, including subjects prematurely withdrawn.

Demographic and Baseline Characteristics
Subject Demographic Characteristics, Medical History and Diagnoses The following data have been collected: sex, age at screening, height, weight, and race. Body mass index (BMI) per subject have been calculated from body weight and height data:

BMI=body weight [kg]·(height [m])$^{-2}$

All variables concerning demographic and background characteristics have been listed individually and summarized.

Deviations from inclusion criteria related to medical history and diagnoses have been listed and described individually.

Baseline Pharmacodynamic Parameters

Baseline blood glucose levels have been summarized by sequence.

Baseline Safety Parameters

For safety variables, the latest scheduled value before study drug administration within the period or within the study, whatever is applicable for the variable, have been taken as the baseline value. If the baseline pre-dosing value is rechecked before dosing, the rechecked value have been considered as the baseline value and used in statistics.

Extent of Study Treatment Exposure and Compliance

Details of study drug dosing and complementary information have been listed individually and summarized if appropriate.

Prior/Concomitant Medication/Therapy

Prior and concomitant medications/therapies (if any) have been coded according to the World Health Organization-Drug Reference List (WHO-DRL) and have been listed individually.

Analysis of Pharmacodynamic Variables
Description of Pharmacodynamic Variable(s)

In order to achieve comparability between the subjects under the body weight depending insulin dosing, all values for GIR have been divided by the subject's body weight in kg for analysis. Thus, GIR in the below always refers to the body weight standardized glucose infusion rate.

Primary PD variable has been:
Area under the body weight standardized glucose infusion rate time curve [GIR-AUC$_{(0-24h)}$ (mg·kg$^{-1}$)]

Secondary PD variable has been:
Time (h) to 50% of GIR-AUC$_{(0-24h)}$ [T$_{50}$%–GIR-AUC$_{(0-24h)}$ (h)]

The following additional PD variables have been derived:
Area under the body weight standardized glucose infusion rate time curve up to end of clamp [GIR-AUC$_{(0-end)}$ (mg·kg$^{-1}$)]

Fractional areas under the body weight standardized glucose infusion rate time curve [GIR-AUC$_{(4-20h)}$, GIR-AUC$_{(0-12h)}$, GIR-AUC$_{(12-24h)}$ (mg·kg$^{-1}$)]

Maximum body weight standardized glucose infusion rate [GIR$_{max}$ (mg·kg$^{-1}$·min$^{-1}$)]

Time to GIR$_{max}$ [GIR-t$_{max}$ (h)]

In order to provide meaningful and reliable data, the value for GIR$_{max}$ and correspondingly the time to GIR$_{max}$ have been derived from a smoothed GIR curve for each subject.

Primary Analysis

To estimate relative bioefficacy (activity) for GIR-AUC$_{(0-24h)}$ (mg·kg$^{-1}$), the untransformed parameter has been analyzed with a linear mixed effects model.

The mixed model includes fixed terms for sequence, period, formulation, and random terms for subject within sequence, with formulation specific between-subject and within-subject variances and subject-by-formulation variance. Point estimate and 90% confidence interval for the formulation ratio (T/R) have then been obtained based on Fieller's theorem [Fieller, 1954].

Equivalent bioefficacy (activity) has been concluded if the confidence interval for the formulation ratio has been placed within [0.80-1.25].

Assumptions for the distribution of the variable has been checked.

Secondary Analysis/Analysis of Secondary Variables

Individual and mean body weight standardized GIR-profiles as well as mean percentage cumulative profiles over time have been plotted.

PD parameters have been listed individually, and descriptive statistics has been generated.

Formulation ratios (T/R) with confidence limits have been derived for fractional GIR-AUCs (mg·kg$^{-1}$) and maximum standardized glucose infusion rate [GIR$_{max}$ (mg·kg$^{-1}$·min$^{-1}$)] using the corresponding linear mixed effects model as described for the primary analysis.

Time to 50%-GIR-AUC (h) and time to GIR$_{max}$ [GIR-t$_{max}$ (h)] have been analyzed non-parametrically.

Performance of Clamp

Individual profiles of blood glucose concentration have been plotted.

Analysis of Safety Data

All summaries of safety data have been based on the safety population.

The individual on-treatment phase for analysis of safety data have started with the first administration of study medication and has ended with the EOS visit.

Adverse Events

All AEs have been coded using MedDRA (version in use).

DEFINITIONS

Treatment Emergent AEs
All AEs have been classified as follows:
Treatment-emergent AEs (TEAEs): AEs that occurred during the on-treatment period for the first time or worsened during the on-treatment period, if present before;
Non-treatment-emergent AEs (NTEAEs): AEs that occurred outside the on-treatment period without worsening during the on-treatment period;

Assignment to Formulations

For analysis purposes, each MAE has been assigned to the last formulation given before onset and/or worsening of the AE. If a TEAE develops on one formulation and worsens under a later formulation, it has been considered a TEAE for both formulations.

Missing Information

In case of missing or inconsistent information, an AE has been counted as a TEAE, unless it can clearly be ruled out that it is not a TEAE (e.g. by partial dates or other information).

If the start date of an AE is incomplete or missing, it has been assumed to have occurred after the first administration of study medication except if an incomplete date indicated that the AE started prior to treatment.

Treatment-Emergent Adverse Events

All AEs have been listed individually. They have been summarized by formulation, including summary by system organ class.

Deaths, Serious and Other Significant Adverse Events

If any such cases, deaths, serious AEs, and other significant AEs have been listed individually and described in the study report in detail.

Adverse Events Leading to Treatment Discontinuation

AEs leading to treatment discontinuation have been listed individually and described in the study report in detail.

Clinical Laboratory Evaluations

Potentially clinically significant abnormalities (PCSA) and out-of-range criteria have been defined in the statistical analysis plan of this study. Definitions of potentially clinically significant abnormalities (PCSA) and out-of-range definitions have been reported by parameter.

Individual data have been listed by subject and by visit, as well as complementary information.

Subjects with values out of normal ranges and subjects with PCSAs have been analyzed by formulation, and overall for end of study evaluation. Subjects with post-baseline PCSAs have been listed.

Vital Signs

Potentially clinically significant abnormalities (PCSA) and out-of-range criteria have been defined in the statistical analysis plan of this study. Definitions of PCSA and out-of-range definitions have been reported by parameter.

Subjects with PCSAs have been analyzed by formulation, and overall for end of study evaluation. Subjects with post-baseline PCSAs have been listed.

Raw values and derived parameters have been summarized by formulation, and overall for end of study evaluation. Individual data have been listed by subject and by visit with flags for abnormalities, as well as complementary information.

ECG

Potentially clinically significant abnormalities (PCSA) and out-of-range criteria have been defined in the statistical analysis plan of this study. Definitions of PCSA and out-of-range definitions have been reported by parameter.

Subjects with PCSAs at end of study have been analyzed overall. Subjects with post-baseline PCSAs have been listed.

Raw values and derived parameters at SCR and at EOS have been summarized overall. Individual data have been listed by subject and by visit with flags for abnormalities, as well as complementary information.

Analysis of Pharmacokinetic Data

Pharmacokinetic Parameters

Actual relative times have been used to derive PK parameters.

Primary variable has been
INS-$AUC_{(0-24h)}$. ($\mu U \cdot h \cdot mL^{-1}$)

Secondary PK variable has been
Time (h) to 50% of INS-$AUC_{(0-24h)}$[$T_{50\%}$–INS-$AUC_{(0-24h)}$ (h)]

The following additional PK variables have been derived:
Fractional INS-AUCs [INS-$AUC_{(4-20h)}$, INS-$AUC_{(0-12h)}$, INS-$AUC_{(12-24h)}$ ($\mu U \cdot h \cdot mL^{-1}$)]
INS-AUC up to end of clamp [INS-$AUC_{(0-end)}$ ($\mu U \cdot h \cdot mL^{-1}$)]
Maximum serum insulin concentration [INS-$C_{max}$ ($\mu U \cdot mL^{-1}$)]
Time to INS-$C_{max}$ [INS-$T_{max}$ (h)]

Statistical Analysis

Descriptive Analyses

Descriptive statistics of concentration data have been presented by protocol times.

Individual and mean serum insulin concentration profiles have been plotted.

Serum insulin concentrations have been individually listed and descriptive statistics per time point have been generated.

Descriptive statistics of PK parameters have been generated by formulation.

Profiles of C-peptide have been plotted and characterized descriptively.

Primary Analysis

To estimate relative bioavailability for INS-$AUC_{(0-24h)}$, the log-transformed parameter has been analyzed with a linear mixed effects model.

The mixed model included fixed terms for sequence, period, formulation, and random terms for subject within sequence, with formulation specific between-subject and within-subject variances and subject-by-formulation variance.

For INS-$AUC_{(0-24h)}$, point estimate and 90% confidence intervals for the formulation ratio (T/R) have been obtained by computing estimates and 90% confidence intervals for the difference between formulation means within the mixed effects model framework, and then converting to the ratio scale by the antilog transformation.

Equivalent bioavailability has been concluded if the confidence interval for the formulation ratio has been placed within [0.80-1.25].

Analyses of Secondary and Additional PK Parameters

Time to 50%-INS-AUC (h) and time to maximum concentration [INS-$T_{max}$ (h)] have been analyzed non-parametrically.

Log-transformed fractional INS-AUCs and INS-$AUC_{(0-end)}$ ($\mu U \cdot h \cdot mL^{-1}$) and maximum serum insulin glargine concentration [INS-$C_{max}$ ($\mu U \cdot mL^{-1}$)] have been analyzed with the corresponding linear mixed effects model as described for the primary analysis. Point estimators and confidence intervals have been reported.

C-Peptide

As available, profiles of C-peptide have been plotted and characterized descriptively.

PK/PD Analysis

PK/PD analyses have been performed in an explorative manner, if appropriate.

EXAMPLE 6

Study Results

Subject Disposition

A total of 35 subjects, 11 women and 24 men, were screened of which 24 healthy eligible subjects were enrolled, randomized and received at least one dose of study medication. Of the 24 randomized subjects, 1 subject withdrew from the study on own request after the first dose treatment period. Twenty-three (23) subjects completed the study according to the protocol and were included in the pharmacodynamic (PD) and pharmacokinetic (PK) analyses. All 24 treated subjects were included in the safety evaluation.

There were no major protocol deviations.

Demographics Characteristics

The following data were collected: sex, age at screening, height, weight, and race. Body mass indexes (BMI) per subject were calculated from body weight and height data:

BMI=body weight [kg]·(height [m])$^{-2}$.

TABLE 3

Summary of Subject Characteristics - Safety Population

| | | Sex | | |
|---|---|---|---|---|
| | Statistics/ Category | Male (N = 17) | Female (N = 7) | All (N = 24) |
| Age (years) | N | 17 | 7 | 24 |
| | Mean (SD) | 34.8 (6.4) | 39.1 (5.6) | 36.1 (6.3) |
| | (Min, Max) | (25, 45) | (32, 45) | (25, 45) |

TABLE 3-continued

Summary of Subject Characteristics - Safety Population

| Statistics/<br>Category | | Sex | | All<br>(N = 24) |
|---|---|---|---|---|
| | | Male<br>(N = 17) | Female<br>(N = 7) | |
| Weight<br>(kg) | N | 17 | 7 | 24 |
| | Mean (SD) | 80.25 (10.42) | 64.17 (5.70) | 75.56 (11.82) |
| | (Min, Max) | (65.9, 101.2) | (57.6, 74.2) | (57.6, 101.2) |
| Height<br>(cm) | N | 17 | 7 | 24 |
| | Mean (SD) | 180.6 (6.0) | 166.3 (5.1) | 176.4 (8.7) |
| | (Min, Max) | (171, 189) | (158, 174) | (158, 189) |
| BMI (kg/<br>m2) | N | 17 | 7 | 24 |
| | Mean (SD) | 24.55 (2.40) | 23.19 (1.55) | 24.15 (2.24) |
| | (Min, Max) | (20.5, 28.3) | (21.4, 24.6) | (20.5, 28.3) |
| Race<br>[n (%)] | Black | 1 (5.9) | 0 (0) | 1 (4.2) |
| | Caucasian/<br>white | 16 (94.1) | 7 (100) | 23 (95.8) |

Clamp Performance

The two treatment groups, Lantus U 100 and Lantus U 300, were similar regarding the individuals' fasting baseline blood glucose concentrations, which served to define the individuals' glucose clamp level. The duration of the clamps after dosing was 30 hours and the same in all treatment periods.

Primary Endpoints

Equivalence in bio-availability (exposure) for Lantus U 100 and Lantus U 300 was not established. Equivalence in bio-efficacy (activity) for Lantus U 100 and Lantus U 300 was not established.

Primary Variables

The area under the serum insulin glargine concentration time curve from 0 to 24 hours (INS-AUC$_{(0-24h)}$) was not equivalent for Lantus U 100 and Lantus U 300. The exposure was less by about 40% with U300. The area under the GIR versus time curve from 0 to 24 hours (GIR-AUC$_{(0-24h)}$) was not equivalent for Lantus U 100 and Lantus U 300. The activity was less by about 40% with U300.

Secondary Variables

The time to 50% of INS-AUC$_{(0-24h)}$ (h) was similar for Lantus U 100 and Lantus U 300. The time to 50% of GIR-AUC$_{(0-24h)}$ (h) was greater by 0.545 (h) (0.158-1.030) for Lantus U 300, which was statistically significant.

Safety

No serious adverse events (AEs) were reported. Five (5) subjects per treatment (test and reference) reported a total 14 TEAEs, all of which were of mild to moderate intensity, and resolved without sequelae. The most frequently reported event was headache (4 subjects per treatment) followed by nausea, vomiting and pyrexia (1 subject each on U 100), and procedural pain (1 subject on U 300). Of note, headache is a common observation for clamp studies and is related to the infusion of hyper-osmolaric glucose solutions. However, a link to the investigational products cannot be excluded. No injection site reactions were reported.

Conclusions

Insulin glargine U 100 and insulin glargine U 300 are not equivalent in bio-availability (exposure) and bio-efficacy (activity). Exposure and activity after insulin glargine U300 were less by about 40% as compared to exposure and activity after administration of the same amount (0.4 U/kg) from insulin glargine U100.

Insulin glargine U300 did, however, show an even flatter PK (exposure) and PD (activity) profile than insulin glargine U100, as would be desired for a basal insulin. These surprising and unexpected differences in exposure and activity between insulin glargine U100 and insulin glargine U300 formulations after the same s.c. dose to healthy subjects are effectively shown in the figures below. Of note, at the same time blood glucose was constant.

Administration of insulin glargine U 300 was without safety and tolerability issues.

EXAMPLE 7

Study Rationale for Study Comparing the Glucodynamic Activity and Exposure of Three Different Subcutaneous Doses of Insulin Glargine U300

Results from the study in healthy subjects (see examples 1-6) showed the inequivalence in exposure and effectiveness between Lantus® U100 and insulin glargine U300. Subjects received the same dose of insulin glargine (0.4 U/kg) for U100 and U300, but delivery of the same unit-amount from U300 produced about 40% less exposure and effect than delivery from U100. Insulin glargine U300 did, however, show an even flatter pharmacodynamic profile than Lantus® U100, as would be desired for a basal insulin.

A new study described in the following examples therefore compares the glucodynamic activity and exposure of three different subcutaneous doses of insulin glargine U300 versus a standard dose of Lantus® U100 as comparator in a euglycemic clamp setting with type 1 diabetes patients. This study aims to approximate an U300 dose that is equieffective to 0.4 U/kg Lantus® U100 as assessed by parameters of blood glucose disposal provided by the clamp technique.

Insulin glargine exposure is assessed from concentration-time profiles after subcutaneous administration and activity as glucose utilization per unit insulin.

The study is designed to assess the metabolic effect and exposure of different insulin glargine U300 doses compared to a standard dose of Lantus® U100 in a euglycemic clamp setting in subjects with diabetes mellitus type 1. The study comprises 4 treatments (R, $T_1$, $T_2$ and $T_3$), 4 treatment periods (TP1-4) and 4 sequences. There is one screening visit (D-28 to D-3), 4 treatment visits (D1 to D2 in TP1 to TP4), and one end-of-study visit (between D5 to D14 in after last dosing) with final assessment of safety parameters.

Subjects are exposed to each treatment R, $T_1$, $T_2$ and $T_3$ once in a cross-over, double-blind and randomized manner according to a Latin square design. This design is considered appropriate to evaluate the pharmacological effect and exposure of different insulin glargine U300 doses compared to Lantus® U100.

The Lantus® U100 dose of 0.4 U/kg selected for the study is well characterized to provide euglycemia in type 1 diabetes patients and has been readily investigated in other clamp studies with type 1 diabetes patients.

Three different doses are tested for insulin glargine U300, 0.4, 0.6 and 0.9 U/kg. This dose range allows intrapolating an approximate dose equieffective to 0.4 U/kg Lantus® U100. The dose of 0.4 U/kg of insulin glargine U300 has already been tested in healthy volunteers (see examples 1-6) and was found to be less active than 0.4 U/kg Lantus® U100 within 30 hours, the predefined end of observation period. Bioactivity of 0.4 U/kg insulin glargine U300 as measured by the total glucose disposition was 39.4% lower than that of reference medication (0.4 U/kg Lantus® U100). A correspondingly higher dose of insulin glargine U300, e.g. 0.6 U/kg insulin glargine U300, was expected to result in an approximately equivalent glucodynamic activity compared to 0.4 U/kg Lantus® U100. Moreover, the proportional dose escalation allows exploring exposure and effect profiles for dose-proportionality.

A study in patients with type 1 diabetes avoids confounding impact of endogenous insulin and better permits assessment of exposure and duration of action. Furthermore, the lack of an assay specific for insulin glargine forces to use an assay which reads all endogenous insulin. Thus, any added source of insulin other than exogenous insulin glargine would cause falsely too high insulin concentrations.

This study has a cross over design; for practical and ethical reasons not more than 3 U300 doses will be compared to Lantus® U100. Assessment of glucodynamic activity of long acting insulin products requires a euglycemic clamp setting for up to 36 hours owed to the extended duration of action.

The active pharmaceutical ingredient, insulin glargine, is the same in both formulations, U100 and U300. The doses used in this study are within the range of regular use. Although an overall risk of hypoglycemia is not completely excluded, it is controlled by the euglycemic clamp technique.

Pharmacodynamics

The pharmacodynamic activity of insulin glargine is evaluated by the euglycemic clamp technique in type 1 diabetes patients, which is the established standard procedure to evaluate the effect of exogenous administered insulin products on blood glucose disposal.

Parameters specific for assessment of glucose disposition in a euglycemic clamp setting are the body weight standardized glucose infusion rate (GIR), total glucose disposed, GIR-$AUC_{0-36}$, and times to a given percentage of GIR-$AUC_{0-36}$ such as time to 50% of GIR-$AUC_{0-36}$.

Ancillary parameters are the maximum smoothed body weight standardized GIR, $GIR_{max}$, and Time to $GIR_{max}$, GIR-$T_{max}$.

Duration of action of insulin glargine is derived from the time between dosing and pre-specified deviations above the euglycemic (clamp) level.

Glucose monitoring is performed for 36 hours due to the long duration of action of insulin glargine after subcutaneous administration Pharmacokinetics Due to the sustained release nature of insulin glargine there is a lack of pronounced peaks in the concentration profile. Therefore, the time to 50% of INS-AUC ($T_{50}$% INS-$AUC_{0-36}$) is calculated as a measure for the time location of the insulin glargine exposure profile, and INS-$C_{max}$ and INS-$T_{max}$ will serve as additional measures.

Primary Study Objectives

The primary objective of the study is to assess the metabolic effect ratios of three different insulin glargine U300 doses versus 0.4 U/kg Lantus® U100.

Secondary Study Objectives

The secondary objectives of the study are to assess the exposure ratios of three different insulin glargine U300 doses versus 0.4 U/kg Lantus® U100, to compare the duration of action of different insulin glargine U300 doses versus 0.4 U/kg Lantus® U100, to explore the dose response and dose exposure relationship of insulin glargine U300, and to assess the safety and tolerability of insulin glargine U300 in subjects with type 1 diabetes.

EXAMPLE 8

Study Design, Description of the Protocol

Phase I, single-center, double-blind, randomized, crossover (4 treatments, 4 treatment periods and 4 sequences; Latin square), active control, with a wash-out duration between treatment periods (5-18 days, preferred 7 days) in male and female subjects with type 1 diabetes mellitus receiving single-doses of insulin glargine at
    0.4 U/kg Lantus® U100 (=Reference R)
    0.4 U/kg Insulin glargine U300 (=Test $T_1$)
    0.6 U/kg Insulin glargine U300 (=Test $T_2$)
    0.9 U/kg Insulin glargine U300 (=Test $T_3$)

The four treatments R and $T_{1-3}$ are given cross-over in four treatment periods (TP 1 to TP 4) with the four-sequences
    $R$-$T_1$-$T_2$-$T_3$
    $T_3$-$R$-$T_1$-$T_2$
    $T_2$-$T_3$-$R$-$T_1$
    $T_1$-$T_2$-$T_3$-$R$
randomly assigned to the subjects (1:1:1:1 ratio).

Duration of Study Participation
    Total study duration for one subject: about 4-11 weeks (min-max duration, depending on wash-out period, excl. screening)
    Duration of each part of the study for one subject:
    Screening: 3 to 28 days (D-28 to D-3)
    Treatment Period 1-4: 2 days (1 overnight stay)
    Washout: 5-18 days (preferentially 7 days between consecutive dosings)
    End-of-study visit: 1 day between D5 and D14 after last study drug administration

EXAMPLE 9

Selection of Subjects

Number of subjects planned: At least 24 subjects are to be enrolled to have 20 evaluable subjects.

Inclusion Criteria

Demography

I 01. Male or female subjects, between 18 and 65 years of age, inclusive, with diabetes mellitus type 1 for more than one year, as defined by the American Diabetes Association (American Diabetic Association. Report of the Expert Committee on the Diagnosis and Classification of Diabetes Mellitus. Diabetes Care 1998; 21:5-19)

I 02. Total insulin dose of <1.2 U/kg/day

I 03. Body weight between 50.0 kg and 95.0 kg inclusive if male, between 50.0 kg and 85.0 kg inclusive if female, Body Mass Index between 18.0 and 30.0 kg/m² inclusive Health Status I 04. Fasting negative serum C-peptide (<0.3 nmol/L)

I 05. Glycohemoglobin (HbA1c)≤9.0%

I 06. Stable insulin regimen for at least 2 months prior to study (with respect to safety of the subject and scientific integrity of the study)

I 07. Normal findings in medical history and physical examination (cardiovascular system, chest and lungs, thyroid, abdomen, nervous system, skin and mucosae, and musculo-skeletal system), unless the investigator considers any abnormality to be clinically irrelevant and not interfering with the conduct of the study (with respect to safety of the subject and scientific integrity of the study)

I 08. Normal vital signs after 10 minutes resting in the supine position: 95 mmHg<systolic blood pressure<140 mmHg; 45 mmHg<diastolic blood pressure<90 mmHg; 40 bpm<heart rate<100 bpm I 09. Normal standard 12-lead ECG after 10 minutes resting in the supine position; 120 ms<PQ<220 ms, QRS<120 ms, QTc≤440 ms if male, ≤450 ms if female I 10. Laboratory parameters within the normal range (or defined screening threshold for the Investigator site), unless the Investigator considers an abnormality to be clinically irrelevant for diabetes patients; however serum creatinine should be strictly below the upper laboratory norm; hepatic enzymes (AST, ALT) and bilirubin (unless the subject has documented Gilbert syndrome) should be not above 1.5 ULN Female Subjects Only I 11. Women of childbearing potential (less than two years post-menopausal or not surgically sterile for more than 3 months), must have a negative serum β-HCG pregnancy test at screening and a negative urine β-HCG pregnancy test at Day 1 on TP1 to TP4 and must use a highly effective method of birth control, which is defined as those which result in a low failure rate (i.e. less than 1% per year) according to the Note for guidance on non-clinical safety studies for the conduct of human clinical trials for pharmaceuticals (CPMP/ICH/286/95, modifications). During the entire study female subjects of child bearing potential must use two independent methods of contraception, e.g. diaphragm and spermicide-coated condom. The use of a condom and spermicidal creams is not sufficiently reliable.

For postmenopausal women with presence of less than two years post-menopausal, and not surgically sterile for more than 3 months, the hormonal status will be determined (FSH>30 IU/L, estradiol<20 pg/mL)

Exclusion Criteria

Medical History and Clinical Status

E 01. Any history or presence of clinically relevant cardiovascular, pulmonary, gastro-intestinal, hepatic, renal, metabolic (apart from diabetes mellitus type 1), hematological, neurological, psychiatric, systemic (affecting the body as a whole), ocular, gynecologic (if female), or infectious disease; any acute infectious disease or signs of acute illness E 02. More than one episode of severe hypoglycemia with seizure, coma or requiring assistance of another person during the past 6 months E 03. Frequent severe headaches and/or migraine, recurrent nausea and/or vomiting (more than twice a month)

E 04. Blood loss (>300 ml) within 3 months before inclusion

E 05. Symptomatic hypotension (whatever the decrease in blood pressure), or asymptomatic postural hypotension defined by a decrease in SBP equal to or greater than 20 mmHg within three minutes when changing from the supine to the standing position E 06. Presence or history of a drug allergy or clinically significant allergic disease according to the Investigator's judgment E 07. Likelihood of requiring treatment during the study period with drugs not permitted by the clinical study protocol E 08. Participation in a trial with any investigational drug during the past three months E 09. Symptoms of a clinically significant illness in the 3 months before the study, which, according to the investigator's opinion, could interfere with the purposes of the study E 10. Presence of drug or alcohol abuse (alcohol consumption>40 grams/day)

E 11. Smoking more than 5 cigarettes or equivalent per day, unable to refrain from smoking during the study E 12. Excessive consumption of beverages with xanthine bases (>4 cups or glasses/day)

E 13. If female, pregnancy (defined as positive β-HCG test), breast-feeding

Interfering Substance

E 14. Any medication (including St John's Wort) within 14 days before inclusion, or within 5 times the elimination half-life or pharmacodynamic half-life of that drug, whichever the longest and regular use of any medication other than insulins in the last month before study start with the exception of thyroid hormones, lipid-lowering and antihypertensive drugs, and, if female, with the exception of hormonal contraception or menopausal hormone replacement therapy; any vaccination within the last 28 days General Conditions E 15. Subject who, in the judgment of the Investigator, is likely to be non-compliant during the study, or unable to cooperate because of a language problem or poor mental development E 16. Subject in exclusion period of a previous study according to applicable regulations E 17. Subject who cannot be contacted in case of emergency E 18. Subject is the investigator or any sub-investigator, research assistant, pharmacist, study coordinator, or other staff thereof, directly involved in the conduct of the protocol Biological Status E 19. Positive reaction to any of the following tests: hepatitis B surface (HBs Ag) antigen, anti-hepatitis B core antibodies (anti-HBc Ab) if compound having possible immune activities, anti-hepatitis C virus (anti-HCV2) antibodies, anti-human immunodeficiency virus 1 and 2 antibodies (anti-HIV1 and anti HIV2 Ab)

E 20. Positive results on urine drug screen (amphetamines/methamphetamines, barbiturates, benzodiazepines, cannabinoids, cocaine, opiates)

E 21. Positive alcohol test

Specific to the Study

E 22. Known hypersensitivity to insulin glargine and excipients

E 23. Any history or presence of deep leg vein thrombosis or a frequent appearance of deep leg vein thrombosis in first degree relatives (parents, siblings or children)

EXAMPLE 10

Treatments

Investigational Product
  Insulin glargine
  Two different formulations of insulin glargine are used:
    Lantus® U100 solution for injection containing 100 U/mL insulin glargine (marketed product)
    Insulin glargine U300 solution for injection containing 300 U/mL insulin glargine
  Dose:
    Lantus® U100:0.4 U/kg (=Reference R)
    Insulin glargine U300: 0.4, 0.6 and 0.9 U/kg (=Test $T_1$-$T_3$)
  Container: 3 mL glass cartridges
  Route of application: Subcutaneously horizontally 5 cm right and left of the umbilicus
  Conditions: Fasted
  Duration of treatment: 1 day at each period, single dose
  Start: 09:00 on Day 1 (D1) in Treatment Periods 1 to 4 (TP1-4)
  Additional treatments for 100% of included subjects are provided

TABLE 4

Treatments

|  | Reference treatment<br>Lantus ® U100 | Test treatment<br>Insulin glargine U300 |
|---|---|---|
| INN | Insulin glargine (recombinant human insulin analogue) | Insulin glargine (recombinant human insulin analogue) |
| Formulation | Cartridges for 3 mL solution U100<br>1 mL contains:<br>3.637 mg 21A-Gly-30Ba-L-Arg-30Bb-L-Arg human insulin [equimolar to 100 IU human insulin]<br>30 µg zinc<br>2.7 mg m-cresol<br>20 mg glycerol 85%<br>HCl and NaOH, pH 4.0<br>specific gravity 1.004 g/mL | Cartridges for 3 mL solution U300<br>1 mL contains:<br>10.913 mg 21A-Gly-30Ba-L-Arg-30Bb-L-Arg human insulin [equimolar to 300 IU human insulin]<br>90 µg zinc<br>2.7 mg m-cresol<br>20 mg glycerol 85%<br>HCl and NaOH, pH 4.0<br>specific gravity 1.006 g/mL |
| Dose | 0.4 U/kg | 0.4 U/kg<br>0.6 U/kg<br>0.9 U/kg |
| Manufacturer | sanofi-aventis Deutschland GmbH | sanofi-aventis Recherche & Development, Montpelier, France |
| Batch number | commercial formulation, purchased through CRO | tbd |

INN = international nonproprietary name

Dosing

This is a single dose study with in total 4 administrations of study medication. Subjects are randomized to different sequences of the reference and test treatment such that each subject receives the reference treatment (R) and each of the test treatments ($T_{1-3}$) once.

Injections are given left or right of the umbilicus, with both sites being used for separate injections. A washout period of 5 to 18 days separates consecutive dosing days, the preference is 7 days (7 days between consecutive dosing). The length of the wash-out period varies individually allowing both the participant and the investigator to adjust to their needs. By experience, 5 days comprise a minimum period for recovery enabling 1 clamp per week for a participant, while 18 days represent a break of 3 weeks between dosing days, allowing subjects the freedom to fulfill non-study related obligations, if unavoidable.

IP administration is administered under fasting conditions; subject continues to fasten throughout the whole clamp period.

The blood glucose concentration is within a range of 5.5 mmol/L (100 mg/dL)±20% without any glucose infusion for the last hour prior to dosing during pre-clamp. When blood glucose has been stable for at least 1 hour without any glucose infusion, IP is administered, IF administration does not occur earlier than 09:00 clock time in the morning and not later than 14:00 clock time on Day 1 in Treatment Periods 1 to 4. If blood glucose is not stabilized before 14:00 hours, dosing does not occur. The visit is terminated and the subject is scheduled for a new dosing visit 1-7 days later.

Per subject and dosing a new cartridge is used.

IP administration is done by a person who is not otherwise involved in the study or part of the study team at the CRO. This person gets the random code to prepare IP administration in accordance to the open random list and doses subjects accordingly. The preparation and dosing is followed and checked by a second independent person. Respective documents of dose preparation and treatment sequence is kept strictly confidential and is not being disclosed to any other person.

Calculation of Dose of IP (Insulin Glargine)

To calculate the amount of insulin glargine given for each subject, the body weight (in kg) is determined to one decimal place and the amount of insulin calculated is rounded up or down to integer numbers as shown in the following examples for a dose of 0.6 U/kg insulin glargine:

a subject with a body weight of 75.3 kg receives 45 U insulin (75.3×0.6=45.18 which is rounded down to 45);

a subject with a body weight of 74.4 kg receives 45 U insulin (74.4×0.6=44.64, which is rounded up to 45).

The body weight recorded during TP1D1 is used for calculation of study medication dose for all treatment periods. The study medication dose is not to be changed if a subject's weight changes by less than or equal to 2 kg between TP1 and one of the subsequent TPs. If a subject's body weight changes by more than 2 kg between TP1 and one of the subsequent TPs, the study medication dose is re-calculated based on the weight at D1 of the respective treatment period.

Syringes and Needles

Syringes with needles attached appropriate to accurately administer small amounts of injection solution are used only (e.g. Becton Dickinson, Ref 305502, Dimensions: 1 ML 27G 3/8 0.40×10). The syringes are supplied by the investigator.

Other Products

Other products used during the clamp procedure are described in Table 5.

TABLE 5

Preparation of infusion

| Drug Code | INN | Formulation | Manufacturer | Dose/Route of administration |
|---|---|---|---|---|
| Glucose | Glucose | 20% solution for infusion | Certified, selected by PROFIL | iv infusion |

TABLE 5-continued

Preparation of infusion

| Drug Code | INN | Formulation | Manufacturer | Dose/Route of administration |
|---|---|---|---|---|
| Intramed Heparin Sodium | Heparin | Vial containing 5 mL solution (5000 IU/mL) | Certified, selected by PROFIL | iv infusion |
| 0.9% Sodium Chloride | Sodium Chloride | Solution | Certified, selected by PROFIL | iv infusion |
| Apidra ® | Insulin glulisine | 100 U/mL for injection | sanofi-aventis | iv infusion |

Glucose solution, sodium chloride solution, heparin and insulin glulisine is provided by the Investigator.

Glucose solution: 20% glucose solution is infused with the Biostator™ to keep subjects individual blood glucose at the determined target level. A second infusion pump (part of the Biostator™) delivers 0.9% sodium chloride solution to keep the line patent. In case the amount of 20% glucose solution needed exceeds the infusion capacity of the Biostator™, a second glucose infusion pump is engaged.

Heparin: A low dose heparin solution (10.000 Units heparine/100 mL saline) is infused via a double lumen catheter. The heparin solution is taken up together with blood used for the Biostator's™ blood glucose measurement in the other lumen of the catheter and is aimed to prevent blood clotting in the system.

Insulin glulisine: 15 U Apidra® [100 U/mL] is given to 49 mL of saline solution, to which 1 mL of the subject's own blood is added to prevent adhesion, producing a concentration of 0.3 U/mL, which is infused at an individual rate to achieve euglycemia.

Description of Blinding Methods

Subjects receive four different treatments (R, $T_1$, $T_2$ and $T_3$) in a randomized, blinded and crossover design.

In order to maintain the blinding, a third party un-blinded person is involved for IP dispensing and administration. This person is not otherwise involved in the study and/or part of the study team at the CRO, does not disclose any information to anyone and ensures to maintain blinding condition of the study. He/she gets the random code and doses subjects accordingly. The preparation of IP and dosing is followed and checked by a second independent person who has also access to the random code but is equally bound to confidentiality.

Method of Assigning Subjects to Treatment Group

IPs are administered according to the Clinical Study Protocol only to subjects who have given written informed consent.

Subjects who comply with all inclusion/exclusion criteria are assigned just before the Investigational Product administration on Day 1 in Treatment Period 1:

an incremental subject number according to the chronological order of inclusion on the morning of D1 in Treatment Period 1. The 9 digit subject number consists of 3 components (e.g. 276 001 001, 276 001 002, 276 001 003, etc.), of which the first 3 digits (276) are the country number, the middle 3 digits are the site number and the last 3 digits are the subject incremental number within the site. The subject number remains unchanged and allows the subject to be identified during the whole study a treatment number in a pre-planned order following the randomized list with the next eligible subject always receiving the next treatment number according to the randomization list IP administration is in accordance with the randomized treatment sequence.

Subjects withdrawn from the study retain their subject number and their treatment number, if already assigned. Replacement subjects have a different identification number (i.e., 500+the number of the subject who discontinued the study). Each subject receives the same treatment sequence as the subject, who discontinued the trial Screen Failed subjects are assigned a different number, e.g., 901, 902 (to be recorded in the CRF only in case of AE occurring during screening period after signing of informed consent).

Notes: The randomization of a subject occurs after Investigators confirmation of subject's eligibility for this study. Baseline parameters are the parameters available the closest before the dosing.

Packaging and Labeling

Insulin glargine U300 solution is provided by sanofi-aventis in regrouping boxes of 3 mL cartridges.

The respective number of IP is packaged under the responsibility of sanofi-aventis according to good manufacturing practice and local regulatory requirement and provided to CRO.

The content of the labeling is in accordance with the local regulatory specifications and requirements.

Lantus® U100 is commercially available and will be ordered by the CRO.

Storage Conditions

All IP is stored in an appropriate locked room under the responsibility of the Investigator, and must be accessible to authorized personnel only.

The IP has to be stored at +2° C. to +8° C., protected from light, and must not be frozen.

Access to the Randomization Code During the Study

In order to maintain the blinding, a third party un-blinded person is responsible for IP dispensing and administration. This person is not otherwise involved in the study and/or part of the study team at the CRO, does not disclose any information to anyone and ensures to maintain blinding condition of the study. He/she gets the random code and doses subjects accordingly. The preparation of IP and dosing is followed and checked by a second independent person who has also access to the random code but is equally bound to confidentiality.

In case of an Adverse Event, the code is not being broken except in the circumstances when knowledge of the Investigational Product is essential for treating the subject. For each subject, code-breaking material which contains the name of the treatment is supplied as envelopes. It is kept in a safe place on site throughout the Clinical Trial. The Sponsor retrieves all code-breaking material (opened or sealed) on completion of the Clinical Trial.

If the blind is broken, the Investigator documents the date of opening and reason for code breaking in the source data.

The Investigator, the clinical site pharmacist, or other personnel allowed to store and dispense IP is responsible for ensuring that the IP used in the study is securely maintained as specified by the Sponsor and in accordance with the applicable regulatory requirements.

All IP is dispensed in accordance with the Clinical Trial Protocol and it is the Investigator's responsibility to ensure that an accurate record of IP issued and returned is maintained.

Concomitant Treatment

The use of concomitant medication is not allowed during the study as specified in Exclusion Criteria No. E14, with the exception of drugs mentioned there under, and is stopped within a given time frame (see E14) before inclusion of the subject on Day 1 of Treatment Period 1.

To prevent interference of subjects' standard insulin treatment with the clamp measurement, subjects have to abstain from using basal insulins and switch to
- intermediate- or short-acting insulin products from 48 hours prior to dosing at D1 of TP1 to TP4, if on long-acting insulin products, i.e. Lantus® (insulin glargine), Levemir® (detemir) or ultralente insulins,
- short-acting insulins from 24 hours prior to dosing at D1 of TP1 to TP4 if on intermediate acting insulin products, i.e. NPH-insulin The last subcutaneous injection of short-acting insulin is no later than 9 hours before study drug administration. Subjects on pump therapy discontinues the insulin infusion in the morning of Day 1, at least 6 hours prior to each IP administration (around 03:00 clock time assuming start of IP administration at 09:00).

For symptomatic adverse events which are not jeopardizing the subjects' safety (e.g. headache) concomitant medication is reserved for adverse events of severe intensity or of moderate intensity which persist for a long duration. In particular, the use of acetaminophen/paracematol is prohibited if there is a known risk of hepatotoxicity, or as soon as abnormalities of liver enzymes occur.

However, if a specific treatment is required for any reason, an accurate record must be kept on the appropriate record form, including the name of the medication (international nonproprietary name), daily dosage and duration for such use. The Sponsor must be informed within 48 h via e-mail or fax, with the exception of treatment of headache.

Treatment of potential allergic reactions will be in compliance with the recommendations as published elsewhere (Samspon H A, Munoz-Furlong A, Campbell R L et al. Second symposium on the definition and management of anaphylaxis: summary report—Second National Institute of Allergy and Infectious Disease/Food Allergy and Anaphylaxis Network symposium. Journal of Allergy and Clinical Immunology 2006; 117(2):391-397). Dependent on the severity of the allergic reaction treatment with antihistamins, corticosteroids and epinephrine may be considered.

Treatment Accountability and Compliance
  IP compliance:
    IP is administered under direct medical supervision, and an appropriate record is completed by the person responsible for dispensing and administration of IP or his/her delegate; any information on treatment sequence or dose is not disclosed and documents are locked with no access by other persons involved in the study
    IP intake is confirmed by measurable drug assay results
  IP accountability:
    The person responsible for dispensing and administration of IP or his/her delegate counts the number of cartridges remaining in the returned packs, then fills in the Treatment Log Form
    The Investigator records the information about day and time of dosing on the appropriate page(s) of the Case Report Form (CRF)
    The Monitor Team in charge of the study then checks the CRF data by comparing them with the IP and appropriate accountability forms after data base lock (to prevent unblinding of the study)

Used cartridges are kept by the Investigator up to the fully documented reconciliation performed with the Sponsor at the end of the study after data base lock.

EXAMPLE 11

Assessment of Investigational Product

The present study is designed to assess the metabolic effect and exposure ratios of three different insulin glargine U300 doses versus 0.4 U/kg Lantus® U100, to compare the duration of action of different insulin glargine U300 doses versus 0.4 U/kg Lantus® U100, to explore the dose response and dose exposure relationship of insulin glargine U300, and to assess the safety and tolerability of insulin glargine U300 in an euglycemic clamp setting in subjects with diabetes mellitus type 1.

Pharmacodynamics

Euglycaemic Clamp

The pharmacodynamic effect of insulin glargine, mainly the total glucose disposal and duration of insulin action, is evaluated by the euglycemic clamp technique.

During the euglycemic clamp, arterialized venous blood glucose concentration, which reflects the supply for total glucose utilization of all tissues, and the glucose infusion rate (GIR) needed to keep a subject's blood glucose concentration at its target level (clamp level) is continuously measured and recorded using the Biostator™ device (continuous glucose monitoring system, Life Sciences Instruments, Elkhart, Ind., USA).

The amount of glucose required (GIR-AUC) is a measure of the glucose uptake into tissues (glucose disposal or glucose lowering activity) mediated by the exogenous insulin excess. The Biostator™ determines blood glucose levels in 1 min intervals and adjusts the glucose infusion rate in response to changes in blood glucose using a predefined algorithm.

Clamp Procedure

To prevent interference of subjects' standard insulin treatment with the clamp measurement, subjects have to abstain from using basal insulins and switch to
- intermediate- or short-acting insulin products from 48 hours prior to dosing at D1 of TP1 to TP4, if on long-acting insulin products, i.e. Lantus® (insulin glargine), Levemir® (detemir) or ultralente insulins,
- short-acting insulins from 24 hours prior to dosing at D1 of TP1 to TP4 if on intermediate acting insulin products, i.e. NPH-insulin The last subcutaneous injection of short-acting insulin is no later than 9 hours before IP administration. Subjects on pump therapy discontinue the insulin infusion in the morning of Day 1, at least 6 hours prior to each IP administration (around 03:00 clock time assuming start of IP administration at 09:00).

During Treatment Periods 1 to 4 (TP1-TP4), subjects are admitted to the clinic in the morning of D1 after an overnight fast of at least 10 hours.

In the morning of Day 1 the pre-clamp procedure starts and subjects are linked to the Biostator™. Blood glucose concentration is adjusted to 4.4-6.6 mmol/L (80-120 mg/dL) and maintained within these limits by means of iv bolus-administrations of a rapid acting insulin analog (e.g. insulin glulisine) and subsequent individual infusions of glucose as needed.

60 min before study medication administration blood glucose is then adjusted to 5.5 mmol/L (100 mg/dL)±20% (euglycemic clamp level) without any glucose infusion for the last hour prior to dosing. The insulin glulisine infusion is discontinued immediately prior to the administration of the study medication.

When blood glucose has been stable for at least 1 hour within a range of 5.5 mmol/L (100 mg/dL)±20% without any glucose infusion, IP is administered (=T0 on D1 in TP1 to TP4, around 09:00). Subjects receive reference or test medication (R, $T_{1-3}$, see Table 4) as assigned by randomization. Injections is given left or right of the umbilicus.

IP administration does not occur earlier than 09:00 clock time in the morning and not later than 14:00 clock time on Day 1 in Treatment Periods 1 to 4. If blood glucose is not stabilized during pre-clamp before 14:00 clock time, dosing does not occur. The visit is terminated and the subject is scheduled for a new dosing visit 1-7 days later.

IP administration is administered under fasting conditions; subject continues to fasten throughout the whole clamp period.

The euglycemic clamp blood glucose level is continuously maintained by means of iv infusion of glucose solution until clamp end.

The goal of any basal insulin supplementation is to add to or even to substitute endogenous insulin secretion between meals. In subjects without endogenous insulin secretion, as invited to participate in this study, exogenous insulin should provide for just the amount of insulin required to dispose hepatic glucose production. If perfectly matched, there is no need for extra glucose to compensate for excess insulin. The resulting glucose infusion rate approximates zero. Once insulin action ceases, blood glucose concentration rises. The times to onset of rise and to times blood glucose concentrations exceeding predefined thresholds are read by the Biostator™.

Selected doses of Lantus® U100 and insulin glargine U300 are above the average basal need which in turn produce some glucose demand reflected in a sizeable GIR up to 36 hours.

The corresponding parameter indicative of the clamp performance, i.e. the precision for keeping blood glucose at clamp baseline level, is the blood glucose variability over the clamp period. A measure for blood glucose variability is the coefficient of variation (CV %) per individual clamp.

A low coefficient of variation in blood glucose is a prerequisite to properly assess the insulin effect in clamp settings.

The clamp period is not to exceed 36 hours post study medication injection, the predefined clamp end.

Subjects continue fasting during the whole glucose clamp (pre-clamp and clamp) period while having access to water ad libitum.

In case blood glucose passes 11.1 mmol/L (200 mg/dL) prior to the clamp end for 30 minutes after cessation of glucose infusion and the investigator confirms that any possible errors leading to false blood glucose levels above 11.1 mmol/L (200 mg/dL) have been excluded, insulin glulisine used in the pre-IP administration time of the clamp is given to extend the observation period to 36 hours. In that case, the sponsor has to be informed.

The subjects are delinked from the clamp setting when blood glucose is well within the isoglycemic range.

Participants resume their pre-study medication on the day of discharge at TP1 to TP4, i.e. Day 2.

The effect of the IPs is to last about 24-36 hours, which is why the participants is confined to the institute for 2 days.

A washout period of 5 to 18 days separates consecutive clamp period days, the preference is 7 days (7 days between consecutive dosing). The length of the wash-out period varies individually allowing both the participant and the investigator to adjust to their needs. By experience, 5 days comprise a minimum period for recovery enabling 1 clamp per week for a participant, while 18 days represent a break of 3 weeks between dosing days, allowing subjects the freedom to fulfill non-study related obligations, if unavoidable.

Screening and D1 of TP1 is not separated by more than 28 days, while the EOS occurs no earlier than D5 or no later than D14 after last dosing, respectively.

Pharmacodynamic Sampling Times

Arterialized venous blood is continuously drawn at a rate of 2 mL/h for determination of arterial blood glucose concentration every minute during pre-clamp (prior to IP administration) and clamp period (up to 36 hours after IP administration).

Arterialized venous blood samples (0.2 mL) for concurrent Biostator™ calibration, which is a technical requirement, is collected at least in 30 minute intervals after connection to the Biostator™ up to 36 hours after medication.

Number of Pharmacodynamic Samples

Blood glucose is continuously measured during the clamp procedure. In addition, at least 74 samples per subject and treatment period will be collected for calibration of the Biostator™ after IP administration. In total 74*4*24 samples or 7104 samples are collected (see table below).

TABLE 6

Number of blood samples and aliquots per subject during clamp

| Periods | Glucose$^a$ | Glucose$^b$ |
|---|---|---|
| TP1 | Continuously | 74 |
| TP2 | Continuously | 74 |
| TP3 | Continuously | 74 |
| TP4 | Continuously | 74 |
| Total number of samples per subject | Continuously | 296 |

$^a$continuous glucose monitoring at 2 mL/h for PD
$^b$calibration

Pharmacodynamic Handling Procedure

TABLE 7

Sample Handling Procedures

| Analyte | Blood Sample Volume | Handling Procedures |
|---|---|---|
| Glucose for PD | 2 mL/h | none |
| Glucose for calibration | 200 µL | Blood to be filled into capillary and then into sample cup for immediate analysis |

Pharmacodynamic Parameters

The area under the body weight standardized GIR within 36 hours (GIR-AUC$_{0-36}$) and the time to 50% of the total GIR-AUC within 36 hours (T$_{50}$%-GIR-AUC$_{0-36}$) is calculated.

Duration of blood glucose control is taken as the time in euglycemia from dosing to deviation above clamp glucose level (100 mg/dL). Times of controlled blood glucose within predefined margins is taken from dosing to specified thresholds, e.g. blood glucose levels at 110, 130 and 150 mg/dL.

In addition, the maximum smoothed body weight corrected GIR (GIR$_{max}$) and the time to GIR$_{max}$, GIR-T$_{max}$, is assessed.

Further supplemental parameters is derived as appropriate.

Safety

Baseline Demographic Characteristics

The baseline demographic characteristics consists of:
Age (years)
Body weight (kg)
Height (cm)
Body Mass Index (BMI) (kg/m$^2$)

Safety Assessment at Baseline and During the Study
Physical examination at screening: cardiovascular system, chest and lungs, thyroid, abdomen, nervous system, skin and mucosae, and musculo-skeletal system and relevant medical and surgical history, diabetes history (diagnosis of diabetes, onset of insulin treatment, late complications); only findings relevant to the study are documented
Past and current smoking status
Physical examination at pre-dose and during the study: cardiovascular system, abdomen and lungs; only findings relevant to the study are documented
Body temperature (aural)
Vital signs: Heart rate, respiratory rate and systolic and diastolic blood pressure measured after 10 minutes in supine resting position, heart rate and systolic and diastolic blood pressure—also after 3 minutes in standing position (except for unscheduled measurements when connected to Biostator™)

Laboratory Tests (in Fasted Conditions for Blood Samples):
Hematology: Red blood cell count (RBC), hematocrit (Hct), hemoglobin (Hb), white blood cell count (WBC) with differential (neutrophils, eosinophils, basophils, monocytes and lymphocytes), platelets, INR and aPTT
Biochemistry:
Electrolytes: Sodium, potassium, bicarbonate, chloride, calcium
Liver function: AST, ALT, alkaline phosphatase, gamma-glutamyl transferase (γGT), total and conjugated bilirubin
Renal function: creatinine, BUN
Metabolism: Glucose, albumin, total proteins, total cholesterol, triglycerides, HbA1c (at screening, D1 TP1 and EOS), LDH, amylase, lipase, C-peptide (screening only)
Potential muscle toxicity: Creatinine phosphokinase (CPK)
Serology: Hepatitis B antigen (HBs Ag), anti-hepatitis B core antibodies (anti-HBc Ab), anti-hepatitis C antibodies (anti-HCV2), anti-HIV1 and anti-HIV2 antibodies
Archival blood sample: a 5 mL blood sample is collected into a dry, red topped tube, centrifuged at approximately 1500 g for 10 minutes at 4° C.; the serum is then transferred into three storage tubes, which are immediately capped and frozen in an upright position at −20° C. This sample is used if any unexpected safety issue occurs to ensure that a pre drug baseline value is available for previously non-assessed parameters (e.g., serology). If this sample is not used, the Investigator destroys it after the Sponsor's approval Urinalysis: Proteins, glucose, blood, ketone bodies, pH
Qualitative: A dipstick is performed on a freshly voided specimen for qualitative detection using a reagent strip;
Quantitative: A quantitative measurement for glucose, protein, erythrocytes and leucocytes count is required in the event that the urine sample test is positive for any of the above parameters by urine dipstick (e.g., to confirm any positive dipstick parameter by a quantitative measurement).

Urine drug screen: Amphetamines/metamphetamines, barbiturates, benzodiazepines, cannabinoids, cocaine, opiates Alcohol breath test
Pregnancy/hormone test (if female):
β-HCG in blood at screening
urine β-HCG at TP1 to TP4, Day 1
FSH/estradiol, if postmenopausal less than 2 years, at screening only Adverse Events: Spontaneously reported by the subject or observed by the Investigator
ECG telemetry (single lead)
12-lead ECG (automatic)
Anti-insulin antibodies
Blood samples for laboratory tests are taken under fasted conditions.

ECG Methodology
ECG Telemetry
ECG telemetry is continuously monitored by medical personnel. All arrhythmic events will be documented by printing and included in the subject's CRF. This documentation allows for diagnosis of the event, time of occurrence, and duration, and is signed by the Investigator or delegate. The ECG telemetry records is kept for a potential re-analyze taking account the Investigational Product exposure.

Twelve-Lead ECGs
Twelve-lead ECGs are recorded after at least 10 minutes in supine position using an electrocardiographic device (MAC 5500™). The electrodes are positioned at the same place for each ECG recording throughout the study (attachment sites of the leads are marked with an indelible pen).

ECGs is always recorded before the PK sampling (if any). PK samples are drawn as soon as possible (within 15 minutes) after ECG.

Each ECG consists of a 10 second recording of the 12 leads simultaneously, leading to:
a single 12-lead ECG (25 mm/s, 10 mm/mV) print-out with HR, PR, QRS, QT, QTc automatic correction evaluation, including date, time, initials and number of the subject, signature of the investigator, and at least 3 complexes for each lead. The Investigator medical opinion and automatic values is recorded in the CRF. This print-out is retained at the site level
a digital storage that enables eventual further reading by an ECG central lab: each digital file is identified by theoretical time (day and time DxxTxxHxx), real date and real time (recorder time), Sponsor study code, subject number (i.e., 3 digits) and site and country numbers if relevant.

The digital recording, data storage and transmission (whenever requested) comply with all the applicable regulatory requirements (i.e., FDA 21 CFR, part 11).

When vital signs, ECG, and blood samples are scheduled at the same time as an Investigational Product administration and/or a meal, they are done prior to Investigational Product administration and/or meal. Whenever measurements of vital signs, ECG, and blood samples for PK, PD, or safety coincide, the following order is respected: ECG, vital signs, PD, PK, and safety samples; in order to respect exact timing of PK samples (refer to flow-chart for time window allowance for PK samples), the other measures are done ahead of the scheduled time. The assessment schedule is adapted to the design of the study Local Tolerability at Injection Site Findings at the site of injection (such as erythema, edema, papules, induration, vesicles, blisters) are graded mainly according to a Global Irritation Score. A local injection site reaction with a score of ≥3 according to the rating scale is documented additionally as an adverse event.

The subjects are asked to report sensations at the injection site.

Pharmacokinetics

For the assessment of insulin glargine pharmacokinetics, the area under the insulin concentration curve (INS-AUC) up to 36 hours, INS-AUC$_{0-36}$ and the time to 50% of INS-AUC$_{0-36}$ is derived. In addition, the maximum insulin concentration INS-C$_{max}$, and time to C$_{max}$ (INS-T$_{max}$) is obtained.

Sampling Times

Blood is collected for the determination of insulin glargine concentrations at time points 0H, 1H, 2H, 4H, 6H, 8H, 12H, 16H, 20H, 24H, 28H, 32H and 36H after injection of study medication.

Number of Pharmacokinetic Samples

TABLE 8

Number of blood samples per subject

| Periods | Insulin (glargine) |
| --- | --- |
| Treatment Period 1 | 13 |
| Treatment Period 2 | 13 |
| Treatment Period 3 | 13 |
| Treatment Period 4 | 13 |
| Total number of samples per subject | 52 |
| Total number of samples[a] | 52 * 24 = 1248 |

[a]assuming 24 subjects completed the study

Pharmacokinetic Handling Procedure

The exact time of IP administration and sample collection must be recorded in the CRF.

Pharmacokinetic Parameters

The following pharmacokinetic parameters are calculated, using non-compartmental methods for insulin glargine concentrations after single dose. The parameters include, but are not be limited to the following.

TABLE 9

List of pharmacokinetic parameters and definitions

| Parameters | Drug/Analyte | Definition/Calculation |
| --- | --- | --- |
| C$_{max}$ | Insulin | Maximum concentration observed |
| T$_{max}$ | Insulin | First time to reach C$_{max}$ |

TABLE 9-continued

List of pharmacokinetic parameters and definitions

| Parameters | Drug/Analyte | Definition/Calculation |
| --- | --- | --- |
| AUC$_{0-36}$ | Insulin | Area under the concentration versus time curve calculated using the trapezoidal method from time zero to 36 hours post dosing |
| T$_{50\%}$-AUC | Insulin | Time to 50% of AUC$_{0-36}$ |

Sampled Blood volume

TABLE 10

Sampled Blood Volume

| Type | Volume per Sample | Sample Number | Total |
| --- | --- | --- | --- |
| Serology | 2 mL | 1 | 2 mL |
| Hematology | 2.7 mL | 5 | 13.5 mL |
| Coagulation | 2 mL | 3 | 6 mL |
| Biochemistry | 5 mL | 3 | 15 mL |
| Archival Sample | 5 mL | 1 | 5 mL |
| Insulin | 3 mL | 13 * 4 | 156 mL |
| Glucose calibration | 0.2 mL | 74 * 4 | 59.2 mL |
| Glucose continuously | 2 mL/h | 40 * 4 | 320 mL |
| β-HCG (if female)[a] | 0 mL | 1 | 0 mL |
| FSH/estradiol (if female)[a,b] | 0 mL | 1 | 0 mL |
| Anti-insulin antibodies | 3 mL | 2 | 6 mL |
| Total | | | 582.7 mL |

[a]included in serology
[b]if postmenopausal less than 2 years

Measures to Protect Blinding of the Trial

In order to maintain the blinding, a third party un-blinded person is involved for IP dispensing and administration. This person is not otherwise involved in the study and/or part of the study team at the CRO or sponsor. He/she gets the random code provided by sanofi-aventis and does not disclose the random code or any other information to any other person. For safety reason, the treatment randomization code is unblinded for reporting to the Health Authority of any Suspected Unexpected Adverse Drug Reaction (SUSAR) and reasonably associated with the use of the IP according to either the judgment of the Investigator and/or the Sponsor.

Subject Safety

The Investigator is the primary person responsible for taking all clinically relevant decisions in case of safety issues.

If judged necessary, the opinion of a specialist should be envisaged in a timely manner (e.g. acute kidney failure, convulsions, skin rashes, angioedema, cardiac arrest, electrocardiographic modifications, etc).

EXAMPLE 12

Study Procedures

Visit Schedule

Screening Procedures

Screening procedures are carried out within 28 days up to 3 days prior to inclusion to determine subject's eligibility for participation. The subject receives information on the study objectives and procedures from the Investigator. The subject signs the informed consent prior to any action related to the study. Recording of adverse events starts thereafter.

Prior to screening, subjects have fasted (apart from water) for 10 hours (excluding a small amount of carbohydrates as countermeasure for hypoglycemia, if necessary).

The screening visit includes the following investigations:
1. Demographics (age, sex, race, past and current smoking status, height, body weight, BMI)
2. Physical examination (cardiovascular system, chest and lungs, thyroid, abdomen, nervous system, skin and mucosae, and musculo-skeletal system) and relevant medical and surgical history, diabetes history (diagnosis of diabetes, onset of insulin treatment, late complications); only findings relevant to the study are documented
3. Relevant previous and all concomitant treatments, average insulin regimen in the last 2 months prior to study entry
4. ECG (standard 12 lead), vital signs measurements (pulse rate, systolic and diastolic blood pressure measured after 10 minutes in supine resting position, and after 3 minutes in standing position), and core body temperature (aural)
5. Laboratory tests with hematology, HbA1c, C-peptide, clinical chemistry, serology, urinalysis, urine drug screen, alcohol breath test, β-HCG and FSH/estradiol blood test (female only, if applicable)

One retest within a week is permitted with the result of the last test being conclusive.

Subjects who meet all the inclusion criteria, and none of the exclusion criteria, are eligible for the inclusion visit.

In case of screening failures the basic results of the screening examination are recorded in the source documents.

Inclusion Procedures (Day 1 of Treatment Period 1)

Subjects, who qualify for enrollment into the study, are admitted to the clinic in the fasted state in the morning of D1 of TP1 at approximately 07:00.

The inclusion examination is carried out on the first dosing day (D1, TP1) and includes the following investigations:

Physical examination with updated medical history (AEs), previous/concomitant medication and aural body temperature Body weight, BMI (height measured at screening)

ECG (standard 12 lead), vital signs measurements (heart rate, respiratory rate, systolic and diastolic blood pressure measured after 10 minutes in the supine resting position, and after 3 minutes in the standing position)

Laboratory tests with hematology, clinical chemistry, urinalysis, urine drug screen, alcohol breath test, β-HCG urine test (female only, if applicable).

Each subject receives an incremental identification number according to the chronological order of his/her inclusion in the study.

Randomization occurs on D1/TP1 after confirmation of subject's eligibility by the Investigator. If more than one subject is randomized at the same time, subjects are randomized consecutively according to the chronological order of inclusion on the morning of Day 1/TP1, i.e. the subject with the lowest subject number receives the next available randomization number.

Results of laboratory tests of D1/TP1 are baseline values and considered confirmatory, with the exception of the β-HCG urine test (based on sample collected during screening visit), which must be negative.

If a subject is finally enrolled, a blood sample is taken for archiving and for determination of anti-insulin antibodies (on D1/TP1 only).

Description by Type of Visit

Treatment Periods 1-4 (D1 to D2)

To prevent interference of subjects' standard insulin treatment with the clamp measurement, subjects abstain from using basal insulins and switch to
- intermediate- or short-acting insulin products from 48 hours prior to dosing at D1 of TP1 to TP4, if on long-acting insulin products, i.e. Lantus® (insulin glargine), Levemir® (detemir) or ultralente insulins,
- short-acting insulins from 24 hours prior to dosing at D1 of TP1 to TP4 if on intermediate acting insulin products, i.e. NPH-insulin The last subcutaneous injection of short-acting insulin is no later than 9 hours before IP administration. Subjects on pump therapy discontinues the insulin infusion in the morning of Day 1, at least 6 hours prior to each IP administration (around 03:00 clock time assuming start of IP administration at 09:00).

Upon arrival at the clinic, subjects are asked to ensure that they have had no clinically relevant changes in their physical condition since the previous visit, that they have been compliant with the general and dietary restrictions as defined in the protocol and that they changed their insulin treatment, if required. Violation of the study criteria excludes the subject from further participation in the study. Depending on the kind of violation, a subject may be excluded only from the particular study day, allowing a re-scheduling of the study day once, or for the entire study.

Any changes in the health condition and the concomitant medication of the subjects since the last visit are reported in the subject's medical records (source) and the CRF.

In the morning shortly before administration of study medication (D1 of each TP) body weight, vital signs, 12-lead ECG, ECG monitoring and core body temperature are recorded, an urinalysis and a urine drug and alcohol screen are performed.

The amount of insulin glargine required for injection will be calculated according to subject's body weight.

Hematology is analyzed for incurring anemia on Day 1 of Treatment Period 3. If positive, the wash-out interval between Treatment Periods 3 and 4 is extended to the maximum allowed 18 days or start of TP4 will be postponed until hematological parameters have been normalized. An additional hematological assessment is made on Day 1 of Treatment Period 4.

Subjects remains fasting (apart from water) until the end of the euglycemic clamp.

Subjects are then be prepared for the start of the pre-clamp procedure with three venous lines connected to an automatic glucose reading device (Biostator™) and remain in semi-recumbent position for the entire duration of the sampling period. At approximately 07:30 a dorsal hand vein or lateral wrist vein of the left arm is cannulated and connected to the Biostator™ in order to continuously draw arterialized venous blood for the determination of blood glucose concentration. The left hand is placed into a heated box ("Hot-Box"), which provides for an air temperature of about 55° C., allowing arterialization of venous blood. A second venous line is placed into the antecubital vein of the left arm and is used to collect samples for insulin and reference blood glucose determination. A third vein is cannulated on the contralateral forearm allowing the infusion of 0.9% saline and 20% glucose solution with a pump in the Biostator™ or insulin glulisine with an external pump.

From insertion of the vascular catheters until 60 min before study medication administration at approximately 09:00 on D1, the blood glucose level is maintained within 4.4 to 6.6 mmol/L (80-120 mg/dL, pre-clamp). Depending on the blood glucose level, additional intravenous bolus injection of insulin glulisine is given to keep the blood glucose within the target range. In the 1 hour before study medication administration no intravenous bolus injections are given until clamp end.

Additional blood samples for the determination of blood glucose are taken in at least 30 min intervals to check against a laboratory reference based on the glucose oxidase method. If necessary the Biostator™ is re-calibrated according to results of the laboratory reference method.

Insulin infusion rates are adjusted individually. While keeping blood glucose at the target level both, insulin and glucose infusion rate are minimized during the clamp run-in phase. Insulin glulisine solution is infused by means of a high precision infusion pump (Terumo Spritzenpumpe TE 311™), 20% glucose solution is be applied by a high precision infusion pump (Terumo Infusionspumpe TE 171™).

The clamp level is adjusted 60 min before study medication administration to maintain the blood glucose at about 5.5 mmol/L (100 mg/dL) until the end of the clamp period. The pre-clamp is prolonged and IP administration postponed until 14:00 clock time in case the target glucose level has not been met during the run-in phase (pre-clamp). If the target glucose level cannot be established within until 14:00 clock time, the visit is terminated and the subject may be scheduled for a new dosing visit 1-7 days later.

The insulin glulisine infusion is discontinued immediately before study medication administration. The first insulin sample for PK is taken immediately thereafter. At about 09:00 the study medication is administered (Table 4), either the Reference treatment (R, 0.4 U/kg Lantus® U100)
or the Test treatment ($T_{1-3}$) at one peri-umbilical site
according to the randomization plan, using a standardized skin-fold technique.

During the clamp 12-lead ECGs are taken 2 and 12 hours after injection of IP and at clamp end.

The study medication is administered preferably by the same person at during the whole study. The end of the injection defines time zero (T0), which defines the starting time of the subsequent clamp period and PK sampling.

Every clamp observation period lasts 36 hours and thus ends at approximately at 21:00 on D2, the predefined end-of-clamp. Thereafter the subjects are delinked from the euglycemic clamp setting when blood glucose is well within the isoglycemic range, receive a meal and their usual insulin treatment.

In case blood glucose passes 11.1 mmol/L (200 mg/dL) during the clamp period for 30 minutes after cessation of glucose infusion and the investigator confirms that any possible errors leading to false blood glucose levels above 11.1 mmol/L (200 mg/dL) have been excluded, the rapid acting insulin analog (e.g. insulin glulisine) used in the pre-IP administration time of the clamp is given to extend the clamp period to 36 hours for pharmacokinetic blood sampling. In that case, the sponsor has to be informed. Thereafter the subjects are delinked from the euglycemic clamp setting when blood glucose is well within the isoglycemic range, receive a meal and their usual insulin treatment.

The injection site reaction is assessed 15 minutes as well as one hour after injection of the study medication and documented as an AE if a score of >3 is observed according to the rating scale.

Prior to discharge, a meal ad libitum is served and the usual insulin-treatment will be resumed. Vital signs (heart rate; systolic and diastolic blood pressure measured after 10 minutes in the supine resting position, and after 3 minutes in the standing position) are repeated and blood glucose is measured (the blood glucose reading must be above 80 mg/dL). Subjects are discharged on D2 of TP1 to TP4 after their well-being is ensured by the investigator.

End-of-Study Visit

Subjects return for an end-of-study (EOS) visit between D5 and D14 after last dosing in TP4. Subjects have fasted (apart from water) for 10 hours. The EOS includes the following investigations:

Physical examination (weight, body temperature) with updated medical history
ECG, vital signs measurement
Laboratory tests with hematology, HbA1c, biochemistry, urinalysis, and if female a β-HCG blood test
Any AE occurred or concomitant medication taken since TP4
Blood sample for anti-insulin antibody determination.

The Investigator ensures that based on all available clinical results, the subject can be safely released from the study.

Study Restriction(s)

Subjects ceases their usual insulin treatment on Days −2 to −1, depending on the type of insulin used (long acting, NPH, intermediate). Thereafter, the blood glucose levels are controlled solely by multiple subcutaneous injections of the usual short-acting insulin.

The usual insulin treatment is resumed after discharge on Day 2 in TP1 to TP4.

The subjects do not take any concomitant medication, which will interfere with the metabolic control or the insulin sensitivity of subjects throughout the study and in the two weeks before the study.

Consumption of alcoholic beverages, grapefruit juice, and stimulating beverages containing xanthine derivatives (tea, coffee, Coca Cola-like drinks, chocolate) is not permitted 24 hours before administration of each study medication until the end of the clamp.

Orange juice or similar carbohydrates are given as corrective measures for hypoglycemia during clamp if not adequately counteracted by intravenous glucose infusion when connected to the Biostator™.

No strenuous physical activity is allowed within 2 days before each study medication administration.

Subjects who smoke 5 or less cigarettes per day are included in the study and subjects may smoke during the study, except on D1 and D2 of TP1 to TP4.

On the screening day, subjects come to the unit after an overnight fast of at least 10 hours (excluding a small amount of carbohydrates as countermeasure for hypoglycemia, if necessary).

In the morning of Day 1 in TP1 to TP4, subjects are admitted to the clinic after an overnight fast of at least 10 hours and remain fasting until end of clamp period in Day 2. A meal ad libitum is served after the end of the clamp.

Fluid supply is at least 2500 mL for each 36-hour period.

DEFINITION OF SOURCE DATA

All evaluations listed below that are reported in the CRF are supported by appropriately signed identified source documentation related to:

subject identification
medical history (in case of allergic reaction)
clinical examination, vital signs, body weight and height, body temperature;
laboratory assessments, ECG
pharmacokinetic time points
dates and times of visits and assessments
adverse events
IP administration
previous/concomitant medication
start/end of clamp procedure, clamp data

EXAMPLE 13

Statistical Considerations

Determination of Sample Size

The primary objective of the study is to assess the relative metabolic effect for insulin glargine given as one dose of U100 (R) and three different doses of U300 ($T_1$ to $T_3$).

Based on the data of study PKD10086, a value of approximately 0.375 can be expected for the $SD_{within}$ of GIR-$AUC_{end\ of\ clamp}$ on the natural log-transformed scale.

For the purpose of the sample size calculation within-subject SDs between 0.325 and 0.425 were used.

Table 11 shows the maximum imprecision (in terms of the 90% confidence interval) for a pairwise treatment ratio of adjusted geometric means that will be obtained with 90% assurance, for total number of subject N between 16 and 24, assuming a true within-subject SD of values between 0.325 and 0.425 for log $GIR-AUC_{0-36}$.

TABLE 11

Maximum imprecision for any pairwise ratio

Confidence level: 90%
Assurance: 90%

| Within-subject SD on log scale | Total number of subjects | Maximum imprecision (%) | Maximum width 90% CI for an observed ratio equal to | | |
|---|---|---|---|---|---|
| | | | 0.6 | 0.8 | 1 |
| 0.325 | 16 | 19.7 | (0.48; 0.75) | (0.64; 1.00) | (0.80; 1.25) |
| | 20 | 17.5 | (0.49; 0.73) | (0.66; 0.97) | (0.82; 1.21) |
| | 24 | 15.9 | (0.50; 0.71) | (0.67; 0.95) | (0.84; 1.19) |
| 0.350 | 16 | 21.0 | (0.47; 0.76) | (0.63; 1.01) | (0.79; 1.27) |
| | 20 | 18.7 | (0.49; 0.74) | (0.65; 0.98) | (0.81; 1.23) |
| | 24 | 17.0 | (0.50; 0.72) | (0.66; 0.96) | (0.83; 1.21) |
| 0.375 | 16 | 22.4 | (0.47; 0.77) | (0.62; 1.03) | (0.78; 1.29) |
| | 20 | 19.9 | (0.48; 0.75) | (0.64; 1.00) | (0.80; 1.25) |
| | 24 | 18.1 | (0.49; 0.73) | (0.65; 0.98) | (0.82; 1.22) |
| 0.400 | 16 | 23.7 | (0.46; 0.79) | (0.61; 1.05) | (0.76; 1.31) |
| | 20 | 21.1 | (0.47; 0.76) | (0.63; 1.01) | (0.79; 1.27) |
| | 24 | 19.2 | (0.48; 0.74) | (0.65; 0.99) | (0.81; 1.24) |
| 0.425 | 16 | 24.9 | (0.45; 0.80) | (0.60; 1.07) | (0.75; 1.33) |
| | 20 | 22.3 | (0.47; 0.77) | (0.62; 1.03) | (0.78; 1.29) |
| | 24 | 20.3 | (0.48; 0.75) | (0.64; 1.00) | (0.80; 1.25) |

With 20 subjects, if the true within-subject SD of $GIR-AUC_{0-36}$ is as much as 0.375, the treatment ratio will be estimated with a maximum imprecision of 19.9% (i.e. the 90% CI will be 0.80 and 1/0.80=1.25 times the observed ratio), with 90% assurance.

24 subjects will be included in order to have 20 completed subjects

Subject Description

Disposition of Subjects

A detailed summary of subject accountability including count of subjects included, randomized, exposed (i.e. received any amount of study medication), completed (i.e. subjects who completed all study treatment periods), discontinued along with the main reasons for discontinuation is generated.

Subject disposition at the final visit is presented in a listing including sequence group, disposition status at the end of the study with the date of last administration of study drug, date of final visit, reason for discontinuation. All withdrawals from the study, taking place on or after the start of the first study drug administration, are fully documented in the body of the clinical study report (CSR).

Protocol Deviations

Prior to data lock of the study, Clinical Trial Protocol deviations are examined relative to criteria defined for definition of populations and other study criteria including:

Inclusion and exclusion criteria;
Treatment compliance;
Compliance with the Clinical Trial Protocol with regard to prohibited therapies;
Compliance with the Clinical Trial Protocol with regard to intervals between visits and total treatment duration; and
Whether planned activity and safety evaluation were performed, etc.

Deviations covered include but not be limited to:

Subjects without any evaluation (of any variables) after randomization;
Subjects not exposed;
Subject without any evaluation of the primary variable (if relevant);
Subjects who entered the study even though they did not satisfy the inclusion criteria;
Subjects who developed withdrawal criteria during the study but were not withdrawn;
Subjects who received the wrong treatment or incorrect dose;
Subjects who received a prohibited concomitant medication.

Major deviations are listed and summarized.

Analysis Population

All exclusions from any analysis populations (pharmacodynamic, pharmacokinetic and/or safety) are fully documented in the CSR.

Subjects excluded from any analysis population are listed with treatment sequence, and with reason for exclusion. Any relevant information is fully documented in the CSR. Frequencies of subjects, overall and per treatment, for the analysis populations are tabulated.

For the event of subjects having received treatments that differed from those assigned according to the randomization schedule, analyses are conducted according to the treatment received rather than according to the randomized treatment.

Pharmacodynamic Population

All subjects without any major deviations related to study drug administration, and for whom PD parameters are available, are included in the pharmacodynamic population. For subjects with insufficient PD profiles in one but not both treatment periods, parameters of the sufficient profiles are included in the analysis.

For subjects, who receive (for safety reasons) insulin glulisine within the observation period of 36 hours after dosing of IP, pharmacodynamic data are only taken into account up to the time of administration of insulin glulisine.

Exclusions from Pharmacodynamic Analysis

All exclusions form the pharmacodynamic analysis are listed together with the reason. Exclusions are decided and documented based on the review of the data prior to database lock and unblinding.

Safety Population

All subjects who were exposed to any comparative study treatment, regardless of the amount of treatment administered, are included in the safety population.

Pharmacokinetic Populations

All subjects without any major deviations related to study drug administration, and for whom insulin PK parameters are available, are included in the pharmacokinetic population. For subjects with insufficient insulin PK profiles at one but not all treatment periods, parameters of the sufficient profiles are included in the analysis.

The bioanalytical assay for insulin glargine is interfered by other insulins like insulin glulisine. Therefore, the pharmacokinetic data for insulin glargine of those subjects are excluded from evaluation, who have received (for safety reasons) insulin glulisine within the clamp observation period of 36 hours after IP administration.

Demographic and Baseline Characteristics

Subject Demographic Characteristics, Medical History and Diagnoses

The following data are collected: sex, age, height, weight, and race. Baseline body mass index (BMI) per subject is calculated from pre-dose body weight and height data:

BMI=body weight [kg]/(height [m])$^2$

All variables concerning demographic and background characteristics are listed individually and summarized for the safety population.

Deviations from inclusion criteria related to medical history and diagnoses are listed and described individually.

Baseline Safety Parameters

For safety variables, the latest scheduled value before study drug administration within the period or within the study, whatever is applicable for the variable, is taken as the baseline value. If the baseline pre-dosing value is rechecked before dosing, the rechecked value is considered as the baseline and used in statistics.

Extent of Study Treatment Exposure and Compliance

Details of study drug dosing and complementary information are listed individually and summarized if appropriate.

Individual total doses of insulin glargine are summarized by treatment.

Prior/Concomitant Medication/Therapy

Prior and concomitant medications/therapies (if any) are coded according to the World Health Organization-Drug Reference List (WHO-DRL, latest version in use at time of database lock) and are listed individually.

Concomitant insulin medication (subcutaneous) is listed separately.

Insulin infusion or bolus given at any time during the clamp procedure is listed or plotted over time on an individual basis.

Insulin infusion or bolus given after dosing during the clamp procedure is listed on an individual basis.

Analysis of Pharmacodynamic Variables

All pharmacodynamic analyses encompass data of the pharmacodynamic population. No adjustment of the alpha-level is made for multiple analyses.

For pharmacodynamics of insulin glargine, the blood glucose concentration and glucose infusion rate (GIR) is continuously recorded during the clamp procedure.

Statistical analyses compare test treatments ($T_1$ to $T_3$) with the reference treatment (R)

Description of Pharmacodynamic Variables

In order to achieve comparability between the subjects body weight adjusted insulin dosing, all values for GIR are divided by the subject's body weight in kg for analysis. Thus in the below, if not stated otherwise, GIR always refers to the body weight standardized glucose infusion rate.

Primary PD Variable

The following PD variable is considered primary.

Area under the body weight standardized glucose infusion rate time curve [GIR-AUC$_{0-36}$ (mg/kg)]

GIR-AUC$_{0-36}$ is calculated according to the rectangular rule for the stepwise constant function with timescale in minutes.

Secondary PD Variables

The following PD variables are derived and considered secondary:

Time (h) to 50% of GIR-AUC$_{0-36}$ [$T_{50}$%-GIR-AUC$_{0-36}$ (h)]

Maximum smoothed body weight standardized glucose infusion rate [GIR$_{max}$ (mg*min/kg)]

First time after dosing to reach GIR$_{max}$ [GIR-T$_{ma}$ (h)]

Duration of euglycemia (time to elevation of smoothed blood glucose profile above clamp level) is calculated as the time from dosing to the last value of the smoothed blood glucose concentration curve at or below 105 mg/dL Durations of controlled blood glucose within predefined margins are defined as the time from dosing to the last value of the smoothed blood glucose concentration curve at or below 110 mg/dL 130 mg/dL 150 mg/dL Smoothing The maximum of the raw body weight standardized GIR is subject to the noise in the GIR adjustment. Thus, the derivation of GIR$_{max}$ and the time to GIR$_{max}$, is based upon a LOESS (locally weighted regression in smoothing scatterplots) smoothing technique for the raw body weight standardized GIR data. Due to the expected morphology of the GIR-profiles as known under Lantus®, a smoothing factor of 6% is used (SAS®, PROC LOESS, factor 0.06).

Blood glucose levels are well be subject to noise. Therefore, the duration of euglycemia and the duration of blood glucose control are based upon a LOESS (locally weighted regression in smoothing scatterplots) smoothing technique for the raw blood glucose levels. Due to the expected morphology, a smoothing factor of 6% is used (SAS®, PROC LOESS, factor 0.06).

In case of inadequate smoothing a different smoothing factor is used for an additional analysis.

Additional PD Variables

Further parameters are derived, as:

Time to end of glucose infusion, as the latest time after dosing with GIR above zero Additional PD variables are derived if deemed necessary for interpretation of results.

Primary PD Analysis

Prior to the analysis described below, GIR-AUC$_{0-36}$ is log-transformed (natural log).

Log-transformed GIR-AUC$_{0-36}$ is analyzed with a linear mixed effects model with fixed terms for sequence, period and treatment log(parameter)=sequence+period+treatment+error and with an unstructured R matrix of treatment (i, i) variances and covariances for subject within sequence blocks, using SAS PROC MIXED.

90% confidence interval (CI) for the ratio of treatments geometric means (T$_1$/R, T$_2$/R, T$_3$/R) is obtained by computing estimate and 90% CI for the difference between treatment means within the linear mixed effects model framework, and then converting to ratio of geometric means by the antilog transformation. Equivalence is concluded if the 90% CI for the ratio is entirely within the 0.80 to 1.25 equivalence reference interval.

Listings of individual ratios (test treatments versus reference treatment) are provided with the corresponding descriptive statistics.

Secondary Analysis/Analysis of Secondary Variables

Descriptive Presentations for GIR Profiles

Individual body weight standardized GIR (mg*min/kg) is plotted for raw, smoothed and cumulative raw values.

Mean and median body weight standardized GIR-profiles as well as median percentage cumulative profiles over time are plotted by treatment.

Cumulative plots cover the time between dosing to end of clamp.

Descriptive Presentations for Derived PD Parameters

PD parameters are listed individually, and descriptive statistics are generated by treatment.

Treatment Ratios for Secondary PD Parameters

Treatment ratios (T$_1$/R, T$_2$/R, T$_3$/R) with confidence limits are derived for maximum standardized glucose infusion rate [GIR$_{max}$ (mg*min/kg)] using the corresponding linear mixed effects model as described above for the primary analysis. Exploratory comparisons between treatments are based on conventional bioequivalence criteria (90% confidence limits 0.80 to 1.25).

The distribution of GIR-T$_{max}$ values is represented by histogram plots for each treatment. In addition, a histogram of differences in GIR-T$_{max}$ between test treatments and reference is provided.

Treatment Differences for Secondary PD Parameters

T$_{50}$%-GIR-AUC$_{0-36}$ (h) is analyzed non-parametrically based on Hodges-Lehmann method for paired treatment comparisons. CIs for pair-wise treatment differences (T1-R, T2-R, T3-R) in medians are derived. The distribution of T$_{50\%}$-GIR-AUC$_{0-36}$ values is represented by histogram plots for each treatment. In addition, a histogram of differences in T$_{50}$%-GIR-AUC$_{0-36}$ between treatments (T1-R, T2-R, T3-R) is provided.

The distribution of GIR-T$_{max}$ values is represented by histogram plots for each treatment. In addition, a histogram of differences in GIR-T$_{ma}$, between test treatments and reference is provided.

Duration of euglycemia and of blood glucose control are presented by histogram plots. Treatment comparisons are performed non-parametrically.

Performance of Clamp

Individual profiles of blood glucose concentration are plotted.

Duration of clamp is derived per clamp as the time between dosing and end of clamp in hours.

Individual variability of blood glucose per clamp is derived as the coefficient of variation (CV %) of blood glucose values between individual start and individual end of clamp (or first administration of insulin glulisine during clamp). Individual average blood glucose level per clamp is derived as the arithmetic mean of blood glucose values between individual start and individual end of clamp (or first administration of insulin glulisine during clamp).

Parameters are listed individually and summarized descriptively within treatment.

Analysis of Safety Data

The safety evaluation is based upon the review of the individual values (potentially clinically significant abnormalities), descriptive statistics (summary tables, graphics) and if needed on statistical analysis (appropriate estimations, confidence intervals). "Potentially Clinically Significant Abnormalities" (PCSA) criteria are used according to standard criteria of sanofi-aventis. Criteria are documented in the statistical analysis plan of this study. The safety analysis is conducted according to the sanofi-aventis standards related to analysis and reporting of safety data from clinical trials.

All safety analyses encompass data of the safety population.

For all safety data, the observation period is divided into segments of three different types:
  the pre-treatment period is defined as the time between when the subject gives informed consent and the first administration of study medication.
  the on-treatment period is defined as the time from (first) study medication administration up to 72 hours later.
  the post-treatment period is defined as the time after on-treatment period to either the (first) administration of study medication in the next period or the end of the follow-up period.

Adverse Events

All AEs are coded using MedDRA (latest version in use at time of database lock).

The following listings are provided for all adverse events:
Listing of all adverse events (by subject)
Listing of comments related to adverse events

DEFINITIONS

For safety data, the observation period is divided into segments of three different types:
  the pre-treatment period is defined as the time between when the subject gives informed consent and the first administration of comparative study medication.
  the on-treatment period per period is defined as the time from (first) study medication administration up to 72 hours later.
  the post-treatment period is defined as the time after on-treatment period to either the (first) administration of study medication in the next period or the end of the follow-up period.

Treatment Emergent Adverse Events

All AEs are classified as follows:
  Treatment-emergent adverse events (TEAEs) are any AEs with an onset (incl. worsening) during an on-treatment period
  Non-treatment-emergent adverse events (NTEAEs) are any AEs not classified as TEAE:
    Pre-treatment AEs, defined as AEs that developed (or worsened) during the pre-treatment period before the first dose of study medication Post-treatment AEs, defined as AEs that developed during a post-treatment period without worsening during an on-treatment phase.

Assignment to Treatments

For analysis purposes, each TEAE is assigned to the last treatment given before onset (or worsening) of the AE. If a TEAE develops on one treatment and worsens under a later treatment, it is considered treatment emergent for both treatments.

Missing Information

In case of missing or inconsistent information, an AE is counted as a TEAE, unless it can clearly be ruled out that it is not a TEAE (e.g. by partial dates or other information).

If the start date of an AE is incomplete or missing, it is assumed to have occurred after the first administration of study medication except if an incomplete date indicates that the AE started prior to treatment.

Treatment-Emergent Adverse Events

Treatment emergent adverse events are listed and summarized by treatment:
- Overview of TEAEs (number and percentage of subjects with at least one TEAE, severe TEAE, TEAE leading to discontinuations, death (if any))
- Summary of all treatment-emergent adverse events by primary system organ class and preferred term (number and percentage of subjects with at least one TEAE) ("in-text table")
    - Table without number of events (for body of the clinical study report)
    - Table with number of events (for appendix of the clinical study report)
    - Table with number of subjects per formulation (U100, U300) and of subjects overall (for appendix of the clinical study report)
- Listing of subjects presenting treatment emergent adverse events by treatment, system organ class and preferred term Deaths, Serious and Other Significant Adverse Events In case of any occurrences, deaths, serious AEs, and other significant AEs are listed individually and described in the study report in detail.

Adverse Events Leading to Treatment Discontinuation

In case of any occurrences, individual subject listings are generated for all adverse events leading to treatment discontinuation.

Clinical Laboratory Evaluations

Hematology and Biochemistry Data

Laboratory safety parameters are measured on D1 of treatment period 1 and at EOS. Per schedule, these safety parameters are assessed during the on-treatment period (except hematology at TP3 and TP4).

The values to be used as baseline (hematology and biochemistry) are the values collected on D1 predose in the first treatment period. If any of the scheduled baseline tests are repeated for any subject, the last rechecked values are considered as baselines, provided they were done before the first IP administration.

The following tables and listings are provided:
- Descriptive statistics for raw data and changes from baseline (including % change for creatinine)
- A specific listing of individual data from subjects with post-baseline PCSAs will be provided, sorted by function and time of measurement
- All individual data, including rechecked values, for planned hematology and biochemistry, are listed by biological function and time of measurement. If any, data from unscheduled laboratory tests are included in this listing. In these listings, individual data are flagged when lower or higher than the lower or upper laboratory limits and/or when reaching the absolute limit of PCSA criteria, when defined
- A listing of liver function data for subjects, who experienced at least one of the following:
    at least one occurrence of ALT>3ULN and at least one occurrence of total bilirubin
    >2 ULN during the study with at least one of them being post first dose
    conjugated bilirubin>35% total bilirubin and total bilirubin>1.5 ULN will be provided on the same sample post first dose, irrespective of the definition for the on-treatment phase.
- A listing related to increase in ALT≥2 ULN is provided, including notably the information on drug intake, medical and surgical history, alcohol habits, trigger factors, event details with ALT values, associated signs and symptoms.
- A listing of out-of-range definitions is provided.

In the listings of subjects with PCSAs, liver function data, CPK, and eosinophils are expressed as multiple of the corresponding ULN.

Urinalysis Data

All qualitative urinary test results (dipstick), including rechecked values, are listed.

Vital Signs

Blood Pressure and Heart Rate

Heart rate and systolic and diastolic blood pressure (SBP and DBP) are measured after 10 minutes in supine resting position and also after 3 minutes in standing position, except when connected to the Biostator™.

The values to be used as the baselines are the D1 pre-dose assessment value of each treatment period. If any of the scheduled baseline tests are repeated for any subject, the last rechecked values are considered as baselines, provided they were done before the IP administration.

For heart rate and blood pressures, orthostatic differences are calculated as the change from supine to standing position.

For all parameters, an "On-Treatment" analysis will be performed including all unplanned values and rechecked values.

The following tables and listings are provided:
- Summary tables of counts of subjects with PCSAs are provided as incidence tables of post-baseline PCSAs, regardless of the normal or abnormal status of the baseline
- For heart rate and blood pressures (supine and standing positions), raw data and changes from baseline (supine position only) are summarized in descriptive statistics, for type of measurement (position) each parameter and time point, based on planned pre-dose measurements and the baseline defined
- All individual data, including unplanned and rechecked values, are listed (supine, standing, orthostatic difference). In the listings, values are flagged when reaching the limits of the PCSA criteria when defined
- A data listing of individual post-baseline PCSAs is provided
- Comments related to vital sign evaluations are also listed in the Appendix, if any.

Body Weight, Body Mass Index, and Body Temperature

The values to be used as baselines for body weight and BMI are the values collected on D1 of TP1.

The values to be used as baselines for body temperature are the values collected on D1 of each TP.

Individual data are listed including flags (weight only) for values when reaching the limits of the PCSA criteria.

ECG

Heart rate, PQ-, QRS-, and QT-intervals and corrected QT (QTc) from automatic reading are analyzed as raw parameter value and change from baseline.

The values to be used as the baseline are the Day 1 predose value of each period. If any of the scheduled baseline tests are repeated for any subject, the rechecked values are considered as baselines, provided they were done before the drug administration of the period.

For all parameters, an on-treatment analysis is performed using all post-baseline assessments done during the on-treatment period, including rechecked values. Counts of subjects with postbaseline PCSAs are provided in summary tables regardless of the normal or abnormal status of the baseline, by treatment group.

Raw data for all parameters and change from baseline are summarized in descriptive statistics by parameter, treatment, and time of measurement.

Individual data, including rechecked values, are listed, sorted by treatment, subject, visit and time of measurement. In the listings, values reaching the limits of the PCSA criteria are flagged.

A listing of individual data from subjects with post-baseline PCSAs is provided, sorted by type of measurement and sorted by subject, period, and time of measurement.

Additionally, a separate listing of the cardiac profile for subjects with prolonged QTc (>450 ms for Males and >470 ms for Females) or changes from baseline in QTc>60 ms (for males and females) and a listing of subjects with at least one abnormality in qualitative assessment (i.e., abnormal ECG) after the 1st dosing are also provided.

Other Related Safety Parameters

Physical Examination

Listing of comments related to physical examination is provided, if any.

Local Tolerability at Injection Site

Frequency distributions by treatment are provided for levels of local tolerability at injection site. Individual data are listed. Within each criterion and treatment, a subject is counted with their most severe result.

Allergic Reactions

Listings for Allergic Reactions

Any cases of allergic reaction are documented as adverse events with detailed complementary information. All cases are described in detail in the clinical study report.

Individual cases and all complementary data are listed.

Allergic Medical History and Family Medical History

Allergic medical history and family medical history is documented for subjects with any occurrence of potential allergic reaction. All details of allergic medical history and of allergic family medical history are listed on an individual basis.

Anti-Insulin Antibodies

A summary table is provided with the number of subjects for the anti-insulin antibodies results during the study and from the post study investigations. Individual subject listing is provided.

Analysis of Pharmacokinetic Data

Pharmacokinetic Parameters

The list of PK parameters is shown above. In addition, $T_{50\%}$-$AUC_{0-36}$ for insulin is derived in the context of the statistical analysis.

Statistical Analysis

Pharmacokinetic parameters of insulin glargine are listed and summarized using at least arithmetic and geometric means, standard deviation (SD), standard error of the mean (SEM), coefficient of variation (CV %), minimum, median and maximum for each treatment.

All pharmacokinetic analyses encompass data of the corresponding pharmacokinetic populations as defined above. No adjustment of the alpha-level is made for multiple analyses.

Statistical analyses compare test treatments ($T_1$ to $T_3$) versus reference treatment (R).

Analysis of Treatment Ratios

The analysis is performed for $AUC_{0-36}$ for insulin glargine. Prior to all analysis described below, $AUC_{0-36}$ values are log-transformed (natural log).

Log-transformed parameters are analyzed with a linear mixed effects model with fixed terms for sequence, period and treatment $$\log(\text{parameter}) = \text{sequence} + \text{period} + \text{treatment} + \text{error},$$

and with an unstructured R matrix of treatment (i, i) variances and covariances for subject within sequence blocks, using SAS PROC MIXED.

Estimate and 90% confidence interval (CI) for the ratio of treatments geometric means ($T_1$/R, $T_2$/R, $T_3$/R) are obtained by computing estimate and 90% CI for the difference between treatment means within the linear mixed effects model framework, and then converting to ratio of geometric means by the antilog transformation. Bioequivalence is concluded if the 90% CI for the ratio is entirely within the 0.80 to 1.25 equivalence reference interval.

Listings of individual treatment ratios ($T_1$/R, $T_2$/R, $T_3$/R) are provided with the corresponding descriptive statistics.

$T_{50\%}$-$AUC_{0-36}$ for Insulin

The distribution of $T_{50\%}$-$AUC_{0-36}$ values for insulin is represented by histogram plots for each treatment. In addition, a histogram of differences in $T_{50\%}$-$AUC_{0-36}$ between treatments ($T_1$-R, $T_2$-R, $T_3$-R) is provided.

$T_{50\%}$-$AUC_{0-36}$ (h) is analyzed non-parametrically.

Dose exposure relationship for insulin glargine U300

Descriptive analyses of dose exposure relationship

Dose exposure relationship for insuline glargine U300 is described graphically by
  plots per subject of exposure over total dose per subject
  plots per subject of exposure over dose per kg bodyweight
  plots per subject of dose normalized exposure over dose per kg bodyweight (dose normalization on 0.6 U/kg)

If deemed necessary for interpretation of results, additional descriptive analyses are added.

Statistical Analysis of Dose Exposure Relationship

For AUC of insulin glargine calculated for the test treatments $T_1$-$T_3$, dose exposure relationship is assessed using the empirical power model (PK-parameter=$a^*\text{dose}^b$), along with an "estimation" interpretation, according to the recommendations in Gough et al. (Gough K, Hutchison M, Keene O et al. Assessment of dose proportionality: report from the pharmaceutical industry. Drug Information Journal 1995; 29:1039-1048).

The empirical power model provides a readily and interpretable measure of the degree of non-proportionality, which can be used both to confirm proportionality and to assess the pharmacokinetic and clinical significance of any departures. The analysis of dose proportionality studies, however, requires estimation rather than significance testing in order that the pharmacokinetic and clinical significance of any non-proportionality can be assessed.

The power model is fit on the log-transformed scale using a random coefficients power model for dose (in U/kg body weight):

$$\log(\text{parameter}) = (\log(\text{alpha}) + \text{alpha}[i]) + (\text{beta} + \text{beta}[i]) * \log(\text{dose})$$

where log(alpha) and beta are the population intercept and slope, respectively, and alpha[i] and beta[i] are the random deviations from alpha and beta, respectively, for the i-th subject.

Estimates for beta with 90% confidence intervals are obtained via estimated generalized least squares in the SAS®/PROC MIXED procedure, with restricted maximum likelihood (REML) estimates of covariance parameters. Estimates and 90% confidence intervals for beta are further used to obtain estimates and 90% confidence intervals for the PK parameter increase associated with an r-fold increase in dose (r=1.5 and r=2.25 [i.e. high dose/low dose]), by exponentiating r to the powers of the beta estimate and confidence limits If there is evidence of model lack-of-fit, the mixed effect model (as used for analysis of treatment ratios) is used for the analysis. Estimates with 90% CIs for the parameter increases associated with pairwise dose increases are obtained by first computing estimates with CIs for pairwise differences between doses in the mixed effects model framework, and then converting to ratios using the antilog transformation.

PK/PD Analysis

If appropriate, graphical displays (scatter plots) are generated to explore PK/PD relationship.

EXAMPLE 14

Study Results

Subject Disposition

A total of 24 subjects with Type 1 diabetes mellitus were enrolled, randomized and received at least one dose of study medication. Of the 24 randomized subjects, 2 subject withdrew from the study on own request. Twenty-two (22) subjects completed the study according to the protocol and were included in the pharmacodynamic (PD) and pharmacokinetic (PK) analyses. All 24 treated subjects were included in the safety evaluation.

There were no major protocol deviations.

Demographics Characteristics

The following data (Table 12) were collected: sex, age at screening, height, weight, and race. Body mass indexes (BMI) per subject were calculated from body weight and height data:

$$\text{BMI} = \text{body weight [kg]} \cdot (\text{height [m]})^{-2}.$$

TABLE 12

Demographics

| Sex | BMI (kg/m$^2$) | Weight (kg) | Age (years) | Race (n) [%] | N |
|---|---|---|---|---|---|
| 5 F, 19 M | 25.55 | 79.38 | 42.6 | Caucasian/ | N |
|  | 1.99 (SD) | 9.67 (SD) | 10.0 (SD) | white 24 | 24 |
|  | min | min | min 19:max | [100] |  |
|  | 20.5:max | 57.3:max | 60 |  |  |
|  | 28.3 | 94.3 |  |  |  |

Clamp Performance

At the four treatment periods for each subject, R (Lantus U100), T1 (0.4 U/kg HOE901-U 300), T2 (0.6 U/kg HOE901-U 300) and T3 (0.9 U/kg HOE901-U 300), the individuals' baseline blood glucose concentrations prior to insulin medication were similar, defining the clamp level at 100 mg/dL. The duration of the observation period of the clamps after dosing was 36 hours and the same in all treatment periods.

Primary Endpoints

Equivalence in bio-availability (exposure) and bio-efficacy (activity) for R and T was not established.

Primary Variables

The area under the serum insulin glargine concentration time curve from 0 to 36 hours (INS-AUC$_{(0-36h)}$) was not equivalent for R and T1 and T2 and about equivalent with T3. The exposure was estimated to be less by about 37% with T1, less by about 43% with T2 and similar with T3, compared to R.

The area under the GIR versus time curve from 0 to 36 hours (GIR-AUC$_{(0-36h)}$) was not equivalent for R and T1 and T2 and about equivalent with T3. The exogenous glucose consumption required to preserve blood glucose control was estimated to be less by about 88% with T1, 67% with T2 while about similar with T3.

Secondary Variables

The time to 50% of INS-AUC$_{(0-36h)}$ (h) with R was about 14 h and thus shorter as compared to about 16 h, 16 h and 19 h with T1, T2 and T3, respectively.

The time to 50% of GIR-AUC$_{(0-36h)}$ (h) with R was about 12 h and thus shorter as compared to about 17 h, 18 h and 20 h with T1, T2 and T3, respectively.

Safety

No serious adverse events (AEs) or withdrawals due to AEs were reported. Two subjects on R, 2 on T1 and 4 on T3 reported a total 8 TEAEs, all of which were of mild to moderate intensity, and resolved without sequelae. The most frequently reported event was headache. Of note, headache is a common observation for clamp studies and is related to the infusion of hyper-osmolaric glucose solutions. However, a link to the investigational products cannot be excluded. No injection site reactions were reported with T1, T2 and T3 while 2 subjects on R developed hardly perceptible erythema at the injection site.

Conclusions

Same doses of R and T U 300 are not equivalent in bio-availability (exposure) and bio-efficacy (activity) after single dose administration. Exposure and activity after T1 (0.4 U/kg) and T2 (0.6 U/kg) were less as compared to exposure and activity after administration of R (0.4 U/kg). R and T3 were virtually equivalent as to exposure and exogenous glucose consumption.

T1, T2 and T3 did, however, show yet flatter PK (exposure) and PD (activity) profiles with even less fluctuation around the averages than R, i.e., a profile as it would be desired for basal insulin supply. This is particularly evident when comparing R and T3 which provide nominal equivalent total exposure and total glucose consumption though of different profiles.

These surprising and unexpected differences in exposure and activity between R (Lantus U100) and T (HOE901-U300) formulations in subjects with type 1 diabetes mellitus are effectively shown in the figures below.

Over and above, administration of T (HOE901-U300) was without safety and tolerability issues.

EXAMPLE 15

Study Rationale for Comparing the Glucodynamic Activity and Exposure of Two Different Subcutaneous Doses of (HOE901-U300) to Lantus U100 in Patients with Type 1 Diabetes Mellitus Results from the study in healthy subjects and in subjects with Type 1 diabetes mellitus (see foregoing examples)

showed exposure and effectiveness not to be equivalent between Lantus® U100 and insulin glargine U300. Subjects received the same dose of insulin glargine (0.4 U/kg) for U100 and U300, but delivery of the same unit-amount from U300 produced less exposure at less exogenous glucose consumption to preserve blood glucose control than delivery from U100. Though Lantus U100 shows exposure and pharmacodynamic profiles without pronounced fluctuation around the averages, HOE901-U300 did, however, show even less fluctuation in exposure and pharmacodynamic profiles, as it would be desired for basal insulin supply, with a yet even longer duration of action.

In order to assess the pharmacokinetic and pharmacodynamic profile under steady state conditions, a new study described in the following examples therefore compares two different subcutaneous doses of insulin glargine U300 versus a standard dose of Lantus® U100 as comparator with a final euglycemic clamp setting in patients with type 1 diabetes mellitus. This study aims to estimate an U300 dose that is equieffective to 0.4 U/kg Lantus® U100 as assessed by parameters of blood glucose control and blood glucose disposal provided by the clamp technique.

Insulin glargine exposure is assessed from concentration-time profiles after repeated subcutaneous administration at steady state, and activity as glucose utilization per unit insulin at steady state.

The study comprises two cross-over treatments (R and T1, and R and T2) in 2 parallel groups, with 2 treatment periods (TP1, TP2) and 2 sequences, each. There are one screening visit (D-21 to D-3), treatment visits (D1 to D10 in TP1 and TP2 with evening dosing), with in-house periods (D1 to D4 morning and D8 morning to D10 evening for clamp assessments) and one end-of-study visit (between D7 to D10 after last dosing) with final assessment of safety parameters.

The Lantus® U100 dose of 0.4 U/kg selected for the study is well characterized to provide euglycaemic blood glucose control in type 1 diabetes patients and has been readily investigated in other clamp studies with type 1 diabetes patients.

Two different doses are tested for insulin glargine U300, 0.4 and 0.6 U/kg. This dose range allows intrapolating an approximate dose equieffective to 0.4 U/kg Lantus® U100. The dose of 0.4 U/kg of insulin glargine U300 has already been tested in healthy volunteers and subjects with type diabetes mellitus (see foregoing examples) and was found to be less active than 0.4 U/kg Lantus® U100 within 30 and 36 hours, respectively, the predefined ends of the observation periods. Blood glucose control with 0.4 U/kg insulin glargine U300 required less total glucose disposition than that of reference medication (0.4 U/kg Lantus® U100). A correspondingly higher dose of insulin glargine U300, e.g. 0.6 U/kg insulin glargine U300, is expected to result in even tighter blood glucose control at less total glucose disposition. Moreover, the proportional dose escalation allows exploring exposure and effect profiles for dose-proportionality.

A study in patients with type 1 diabetes avoids confounding impact of endogenous insulin and better permits assessment of exposure and duration of action.

This study has a cross over design; based on the outcome of previous studies not more than two HOE901-U300 doses will be compared to Lantus® U100. Assessment of glucodynamic activity of long acting insulin products requires a euglycemic clamp setting beyond 24 hours, the predefined injection interval, owed to the extended duration of action.

The active pharmaceutical ingredient, insulin glargine, is the same in both formulations, U100 and U300. The doses used in this study are within the range of regular use. Although an overall risk of hypoglycemia is not completely excluded, it is controlled by the euglycemic clamp technique.

Pharmacodynamics

The pharmacodynamic activity of insulin glargine is evaluated by the euglycemic clamp technique in type 1 diabetes patients, which is the established standard procedure to evaluate the effect of exogenous administered insulin products on blood glucose disposal.

Parameters specific for assessment of glucose disposition in a euglycemic clamp setting are the body weight standardized glucose infusion rate (GIR), total glucose disposed within 24 and 36 hours, respectively, $GIR\text{-}AUC_{0\text{-}24}$ and $GIR\text{-}AUC_{0\text{-}36}$, and times to a given percentage of $GIR\text{-}AUC_{0\text{-}24}$ and $GIR\text{-}AUC_{0\text{-}36}$ such as time to 50% of $GIR\text{-}AUC_{0\text{-}36}$.

Ancillary parameters are the maximum smoothed body weight standardized GIR, $GIR_{max}$, and Time to $GIR_{max}$, $GIR\text{-}T_{max}$.

Duration of action of insulin glargine is derived from the time between dosing and pre-specified deviations above the euglycemic (clamp) level.

Glucose monitoring is performed for 36 hours due to the long duration of action of insulin glargine after subcutaneous administration Pharmacokinetics Due to the sustained release nature of insulin glargine there is a lack of pronounced peaks in the concentration profile. Therefore, the time to 50% of INS-AUC (e.g. $T_{50}$% INS-$AUC_{0\text{-}36}$) is calculated as a measure for the time location of the insulin glargine exposure profile, and $INS\text{-}C_{max}$ and $INS\text{-}T_{max}$ will serve as additional measures.

Primary Study Objectives

The primary objective of the study is to assess the blood glucose control and the required exogenous glucose consumption of two different insulin glargine U300 doses versus 0.4 U/kg Lantus® U100 in steady state.

Secondary Study Objectives

The secondary objectives of the study are to assess in steady state, the exposure ratios of two different insulin glargine U300 doses versus 0.4 U/kg Lantus® U100, to compare the duration of action of two different insulin glargine U300 doses versus 0.4 U/kg Lantus® U100, to explore the dose response and dose exposure relationship of insulin glargine U300, and to assess the safety and tolerability of insulin glargine U300 in subjects with type 1 diabetes.

EXAMPLE 16

Change of Dissolution Properties of Acidic Formulations of Long-Acting Insulins at Higher Concentrations The influence of the higher concentrations of insulin glargine formulations with regard to dissolution properties are investigated by using an in-vitro test system. To do so, precipitation studies are performed using a phosphate buffer with a pH of 7.4, simulating the in-vivo conditions.

The supernatant of the precipitated insulin is investigated using HPLC technique to determine the insulin glargine content.

Detailed Description of the Studies:

Preparation of the Precipitation Buffer Solution:

19.32 mg sodium dihydrogen phosphat monohydrat (M: 137.98 g/mol) are dissolved per mL water. 0.1M sodium hydroxide or 0.1M hydrochloric acid is used for adjustment of the pH to 7.4.

Performance of the Precipitation Studies:

Solutions of insulin glargine drug product having concentrations of up to 1000 U/mL and comprising the same total amount of insulin glargine and the buffer are placed in plastic tubes and are slightly shaken. After precipitation of the insulin glargine the dispersions are centrifuged at slow rotations for a pre-defined time period. A defined volume of the dissolution medium is taken out and replaced with fresh buffer medium.

Determination of the Insulin Content:

The content of insulin glargine in the samples from the supernatant is quantified against the respective insulin reference standard by reverse-phase-HPLC using a two mobile phase system, containing a sodium dihydrogenphosphate buffer in water, sodium chloride (NaCl) and different amounts of acetonitrile.

As stationary phase an octadodecyl-column is used, detection wavelength is 215 nm.

The release profile of insulin glargine from the higher concentrated solutions (e.g. U500 and U1000) is flatter and prolonged compared to Lantus U100.

EXAMPLE 17

Microscopic Investigation of Precipitates

The precipitates of insulin glargine formulations having concentrations of 100 U/mL, 300 U/mL, 500 U/mL 700 U/mL and 1000 U/mL have been investigated by microscopy. Said formulations (with an identical amount of 60 U of insulin glargine) have been precipitated in 200 µL of a phosphate buffer, pH 7.4 and were investigated by transmitted light optical microscope (Olympus Model BX61) with the magnitudes 100×, the pictures are shown in the following also presenting the maximum diameters. These investigations revealed differences in the precipitations characteristics, leading to remarkable bigger particles with increasing concentrations. The results are shown in FIGS. 8A-8E.

EXAMPLE 18

Blood Glucose Lowering Effect of Insulin Glargine in Dogs

The blood glucose lowering effect of insulin glargine was evaluated in healthy, normoglycemic Beagle dogs. The dogs received single subcutaneous injections of 0.3 IU/kg. Venous blood glucose was determined before the first injection and subsequently up to 24 h.

Animals were taken from cohort of ~30 healthy, normoglycemic male Beagle dogs, originally obtained from Harlan. The dogs were maintained in kennel groups under standardized conditions. The day before study start the dogs were randomly distributed to study cages. They were fasted 18 hours prior to start and throughout the experiment with free access to tap water. Body weight of the dogs in the present study was between 13 and 27 kg. After each experiment the dogs were allowed to recover for at least two weeks.

The animals were randomized to groups of n=6. At time point zero the animals were treated with single doses of the test compound. Insulin glargine was administered as a single subcutaneous injection a dose of 0.3 IU/kg.

Blood sampling was performed consecutively via puncture of the forearm vein (Vena cephalica) before drug administration (0 h) and thereafter up to 24 hours. Blood glucose was determined enzymatically (Gluco-Quant® Glucose/HK kit on Roche/Hitachi 912).

The effect on blood glucose following subcutaneous injection of differently concentrated preparations of insulin glargine, 100 and 300 units/mL, was tested in healthy, normoglycemic Beagle Dogs With increasing insulin glargine concentration the mean time of action increased from 6.8 h (U100) to 7.69 h (U300), respectively.

By increasing the glargine concentration from 100 to 300 U/mL the blood glucose decreasing time-action profile was changed towards a flatter and prolonged activity in the dog The current data in dogs is consistent with data in humans showing that higher drug concentrations of insulin glargine are positively correlated with profile and longer duration of action.

LIST OF ABBREVIATIONS

° C. Degrees Celsius
ABE Average Bioequivalence
AE Adverse Event
ALT Alanine Aminotransferase
aPPT activated Partial Thromboplastin Time
ARF Acute Renal Failure
AST Aspartate Aminotransferase
β-HCG Beta-Human Choriongonadotropine
bpm beats per minute
cm centimeter
CPK Creatinine Phosphokinase
CRF Case Report Form
DRF Discrepancy Resolution Form
ECG Electrocardiogram
EOS End-of-study (visit)
GCP Good Clinical Practice
GGT Gamma-glutamyl transferase
Hb Hemoglobin
HbA1c Glycocylated hemoglobin
HBs Hepatitis B surface
Hct Hematocrit
HCV Hepatitis C Virus
HIV Human Immunodeficiency Virus
HR Heart Rate
INN International Nonproprietary Name
INR International Normalized Ratio (prothrombin time)
IP Investigational Product
IRB/IEC Institutional Review Board/Independent Ethics Committee
Kg Kilogram
LOQ Limit of quantification
PT Prothrombin Time
QTc QT interval automatically corrected by the ECG machine
QTcB QT interval corrected by Bazett formula
QTcF QT interval corrected by Fridericia formula
QtcN QT interval corrected by a population approach
QtcNi QT interval corrected by individual population approach
RBC Red Blood Cell count
SBP Systolic Blood Pressure
SCR Screening (visit)
UDS Urine Drug Screen
ULN Upper Limit of Normal range
WBC White Blood Cell count

The invention claimed is:

1. An aqueous pharmaceutical formulation comprising 300 U/mL of insulin glargine [equimolar to 300 IU human insulin].

2. The aqueous pharmaceutical formulation of claim 1 further comprising at least one excipient selected from the group consisting of zinc, m-cresol, glycerol, and polysorbate 20.

3. The aqueous pharmaceutical formulation of claim 2 further comprising 90 μg/mL zinc, 2.7 mg/mL m-cresol, and 20 mg/mL glycerol 85%.

4. The aqueous pharmaceutical formulation of claim 3, wherein the zinc is present in the form of zinc chloride.

5. The aqueous pharmaceutical formulation of claim 2 further comprising 90 μg/mL zinc, 2.7 mg/mL m-cresol, 20 μg/mL polysorbate 20, and 20 mg/mL glycerol 85%.

6. The aqueous pharmaceutical formulation of claim 5, wherein the zinc is present in the form of zinc chloride.

7. The aqueous pharmaceutical formulation of claim 1, wherein the pH of the aqueous pharmaceutical formulation is between 3.4 and 4.6.

8. The aqueous pharmaceutical formulation of claim 7, wherein the pH of the aqueous pharmaceutical formulation is 4.0.

9. An aqueous pharmaceutical formulation comprising 300 U/mL of insulin glargine [equimolar to 300 IU human insulin] wherein the pH of the aqueous pharmaceutical formulation is between 3.4 and 4.6.

10. The aqueous pharmaceutical formulation of claim 9, wherein the pH of the aqueous pharmaceutical formulation is 4.0.

11. The aqueous pharmaceutical formulation of claim 9 further comprising at least one excipient selected from the group consisting of zinc, m-cresol, glycerol, and polysorbate 20.

12. The aqueous pharmaceutical formulation of claim 11 further comprising 90 μg/mL zinc, 2.7 mg/mL m-cresol, and 20 mg/mL glycerol 85%.

13. The aqueous pharmaceutical formulation of claim 12, wherein the zinc is present in the form of zinc chloride.

14. The aqueous pharmaceutical formulation of claim 11 further comprising 90 μg/mL zinc, 2.7 mg/mL m-cresol, 20 μg/mL polysorbate 20, and 20 mg/mL glycerol 85%.

15. The aqueous pharmaceutical formulation of claim 14, wherein the zinc is present in the form of zinc chloride.

16. An aqueous pharmaceutical formulation comprising 300 U/mL of insulin glargine [equimolar to 300 IU human insulin], 90 μg/mL zinc chloride, 2.7 mg/mL m-cresol, and 20 mg/mL glycerol 85%, wherein the pH of the aqueous pharmaceutical formulation is 4.0.

17. An aqueous pharmaceutical formulation comprising 300 U/mL of insulin glargine [equimolar to 300 IU human insulin], 90 μg/mL zinc chloride, 2.7 mg/mL m-cresol, 20 μg/mL polysorbate 20, and 20 mg/mL glycerol 85%, wherein the pH of the aqueous pharmaceutical formulation is 4.0.

18. An aqueous pharmaceutical formulation comprising 300 U/mL of insulin glargine [equimolar to 300 IU human insulin], wherein the pharmacokinetic profile and the pharmacodynamic profile of the 300 U/mL aqueous pharmaceutical formulation are flatter than the pharmacokinetic profile and the pharmacodynamic profile of an aqueous pharmaceutical formulation comprising 100 U/mL of insulin glargine, and wherein the pH of the 300 U/mL aqueous pharmaceutical formulation is between 3.4 and 4.6.

19. The aqueous pharmaceutical formulation of claim 18, wherein the pH of the aqueous pharmaceutical formulation is 4.0.

20. The aqueous pharmaceutical formulation of claim 18 further comprising at least one excipient selected from the group consisting of zinc, m-cresol, glycerol, and polysorbate 20.

21. The aqueous pharmaceutical formulation of claim 20 further comprising 90 μg/mL zinc, 2.7 mg/mL m-cresol, and 20 mg/mL glycerol 85%.

22. The aqueous pharmaceutical formulation of claim 21, wherein the zinc is present in the form of zinc chloride.

23. The aqueous pharmaceutical formulation of claim 20 further comprising 90 μg/mL zinc, 2.7 mg/mL m-cresol, 20 μg/mL polysorbate 20, and 20 mg/mL glycerol 85%.

24. The aqueous pharmaceutical formulation of claim 23, wherein the zinc is present in the form of zinc chloride.

25. An aqueous pharmaceutical formulation comprising 300 U/mL of insulin glargine [equimolar to 300 IU human insulin] providing a peakless long acting basal insulin, wherein the pH of the aqueous pharmaceutical formulation is between 3.4 and 4.6.

26. An aqueous pharmaceutical formulation comprising 300 U/mL of insulin glargine [equimolar to 300 IU human insulin] exhibiting an extended duration of exposure of insulin glargine than an aqueous pharmaceutical formulation comprising 100 U/mL insulin glargine, wherein the pH of the U300 U/mL aqueous formulation is between 3.4 and 4.6.

27. The aqueous pharmaceutical formulation of claim 1 further comprising an analogue of exendin-4.

28. The aqueous pharmaceutical formulation of claim 27, wherein the analogue of exendin-4 is selected from the group consisting of lixisenatide, exenatide, and liraglutide.

29. The aqueous pharmaceutical formulation of claim 28 comprising 0.1 μg to 10 μg lixisenatide per Unit insulin glargine.

30. The aqueous pharmaceutical formulation of claim 29 comprising 0.2 to 1 μg lixisenatide per Unit insulin glargine.

31. The aqueous pharmaceutical formulation of claim 30 comprising 0.25 μg to 0.7 μg lixisenatide per Unit insulin glargine.

32. A method of treating Type I or Type II Diabetes Mellitus in a patient in need thereof comprising subcutaneously administering to the patient an aqueous pharmaceutical formulation comprising 300 U/mL of insulin glargine [equimolar to 300 IU human insulin].

33. The method of claim 32, wherein the aqueous pharmaceutical formulation further comprises at least one excipient selected from the group consisting of zinc, m-cresol, glycerol, and polysorbate 20.

34. A method of extending the duration of exposure of a long acting insulin in the treatment of Type I or Type II Diabetes Mellitus in a patient in need thereof comprising subcutaneously administering to the patient an aqueous pharmaceutical formulation comprising 300 U/mL insulin glargine [equimolar to 300 IU human insulin].

35. The method of claim 34, wherein the aqueous pharmaceutical formulation further comprises at least one excipient selected from the group consisting of zinc, m-cresol, glycerol, and polysorbate 20.

36. A method of reducing the incidence of hypoglycaemia in the treatment of Type I or Type II Diabetes Mellitus in a patient in need thereof comprising subcutaneously administering to the patient an aqueous pharmaceutical formulation comprising 300 U/mL insulin glargine [equimolar to 300 IU human insulin].

37. The method of claim 36, wherein the aqueous pharmaceutical formulation further comprises at least one excipient selected from the group consisting of zinc, m-cresol, glycerol, and polysorbate 20.

38. A method of providing a peakless long acting basal insulin in the treatment of Type I or Type II Diabetes Mellitus in a patient in need thereof comprising subcutaneously administering to the patient an aqueous pharmaceutical formulation comprising 300 U/mL insulin glargine [equimolar to 300 IU human insulin].

39. The method of claim 38, wherein the aqueous pharmaceutical formulation further comprises at least one excipient selected from the group consisting of zinc, m-cresol, glycerol, and polysorbate 20.

40. The method of any one of claim 32, 34, 36, or 38, wherein the aqueous pharmaceutical formulation is administered once daily.

41. The method of any one of claim 33, 35, 37, or 39, wherein the aqueous pharmaceutical formulation further comprises 90 µg/mL zinc, 2.7 mg/mL m-cresol, and 20 mg/mL glycerol 85%.

42. The method of any one of claim 33, 35, 37, or 39, wherein the aqueous pharmaceutical formulation further comprises 90 µg/mL zinc, 2.7 mg/mL m-cresol, 20 µg/mL polysorbate 20, and 20 mg/mL glycerol 85%.

43. The method of any one of claim 33, 35, 37, or 39, wherein the zinc in the aqueous pharmaceutical formulation is present in the form of zinc chloride.

44. The method of any one of claim 32, 34, 36, or 38, wherein the pH of aqueous pharmaceutical formulation is between 3.4 and 4.6.

45. The method of claim 44, wherein the pH of the aqueous pharmaceutical formulation is 4.0.

46. The method of any one of claim 33, 35, 37, or 39, wherein the aqueous pharmaceutical formulation further comprises 90 µg/mL zinc chloride, 2.7 mg/mL m-cresol, and 20 mg/mL glycerol 85%, and wherein the pH of the aqueous pharmaceutical formulation is 4.0.

47. The method of any one of claim 32, 34, 36, or 38, wherein the pharmacokinetic profile and pharmacodynamic profile of the 300 U/mL aqueous pharmaceutical formulation are flatter than the pharmacokinetic profile and pharmacodynamic profile of an aqueous pharmaceutical formulation comprising 100 U/mL of insulin glargine, and wherein the pH of the 300 U/mL aqueous pharmaceutical formulation is between 3.4 and 4.6.

48. A method of treating Type I or Type II Diabetes Mellitus in a patient in need thereof comprising subcutaneously administering to the patient an aqueous pharmaceutical formulation comprising 300 U/mL of insulin glargine [equimolar to 300 IU human insulin], wherein the pH of the aqueous pharmaceutical formulation is between 3.4 and 4.6.

49. The method of claim 48, wherein the pH of the aqueous pharmaceutical formulation is 4.0.

50. The method of claim 48, wherein the aqueous pharmaceutical formulation further comprises at least one excipient selected from the group consisting of zinc, m-cresol, glycerol, and polysorbate 20.

51. The method of claim 50, wherein the aqueous pharmaceutical formulation further comprises 90 µg/mL zinc, 2.7 mg/mL m-cresol, and 20 mg/mL glycerol 85%.

52. The method of claim 51, wherein the zinc is present in the form of zinc chloride.

53. The method of claim 50, wherein the aqueous pharmaceutical formulation further comprises 90 µg/mL zinc, 2.7 mg/mL m-cresol, 20 µg/mL polysorbate 20, and 20 mg/mL glycerol 85%.

54. The method of claim 53, wherein the zinc is present in the form of zinc chloride.

55. The method of any one of claim 32, 34, 36, 38, or 48, wherein the aqueous pharmaceutical formulation further comprises an analogue of exendin-4.

56. The method of claim 55, wherein the analogue of exendin-4 is selected from the group consisting of lixisenatide, exenatide and liraglutide.

57. The method of claim 56, wherein the aqueous formulation comprises 0.1 µg to 10 µg lixisenatide per Unit insulin glargine.

58. The method of claim 57, wherein the aqueous formulation comprises 0.2 to 1 µg lixisenatide per Unit insulin glargine.

59. The method of claim 58, wherein the aqueous formulation comprises 0.25 µg to 0.7 µg lixisenatide per Unit insulin glargine.

\* \* \* \* \*